(12) United States Patent
Röhrig et al.

(10) Patent No.: US 10,138,236 B2
(45) Date of Patent: Nov. 27, 2018

(54) FACTOR XIA-INHIBITING PYRIDOBENZAZEPINE AND PYRIDOBENZAZOCINE DERIVATIVES

(71) Applicant: BAYER PHARMA AKTIENGESELLSCHAFT, Berlin (DE)

(72) Inventors: Susanne Röhrig, Hilden (DE); Alexander Hillisch, Solingen (DE); Stefan Heitmeier, Wülfrath (DE); Martina Victoria Schmidt, Köln (DE); Karl-Heinz Schlemmer, Wuppertal (DE); Adrian Tersteegen, Wuppertal (DE); Martina Schäfer, Berlin (DE); Henrik Teller, Schwann (DE); Eloisa Jimènez Nùnez, Wuppertal (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/514,276

(22) PCT Filed: Sep. 22, 2015

(86) PCT No.: PCT/EP2015/071645
§ 371 (c)(1),
(2) Date: Mar. 24, 2017

(87) PCT Pub. No.: WO2016/046157
PCT Pub. Date: Mar. 31, 2016

(65) Prior Publication Data
US 2017/0275282 A1  Sep. 28, 2017

(30) Foreign Application Priority Data
Sep. 24, 2014 (EP) .................. 14186080

(51) Int. Cl.
*C07D 471/04* (2006.01)
(52) U.S. Cl.
CPC .................. *C07D 471/04* (2013.01)
(58) Field of Classification Search
CPC .................. C07D 471/04
See application file for complete search history.

(56) References Cited

FOREIGN PATENT DOCUMENTS

| GB | 2 497 806 | 6/2013 |
|----|-----------|--------|
| GB | 2497806 A | 6/2013 |
| WO | 2000/06568 | 2/2000 |
| WO | 2000/06569 | 2/2000 |
| WO | 2001/19355 | 3/2001 |
| WO | 2001/19776 | 3/2001 |
| WO | 2001/19778 | 3/2001 |
| WO | 2001/19780 | 3/2001 |
| WO | 2002/42301 | 5/2002 |
| WO | 2002/070462 | 9/2002 |
| WO | 2002/070510 | 9/2002 |
| WO | 2003/095451 | 11/2003 |
| WO | 2005/063754 | 7/2005 |
| WO | 2005/105779 | 11/2005 |
| WO | WO 2006/030032 A1 | 3/2006 |
| WO | 2008/079787 | 7/2008 |
| WO | WO 2008/079787 A2 | 7/2008 |
| WO | 2010/105770 | 9/2010 |
| WO | 2011/104322 | 9/2011 |
| WO | 2011/147809 | 12/2011 |
| WO | 2012/004258 | 1/2012 |
| WO | 2012/028647 | 3/2012 |
| WO | 2012/059549 | 5/2012 |
| WO | WO 2014/154794 A1 | 10/2014 |
| WO | WO 2014/160592 A2 | 10/2014 |
| WO | WO 2015/011087 A1 | 1/2015 |
| WO | WO 2015/063093 A1 | 5/2015 |
| WO | 2016/071212 | 5/2016 |

OTHER PUBLICATIONS

International Search Report for PCT/EP2015/071645, five pages, dated Nov. 10, 2015.
Written Opinion of the ISA for PCT/EP2015/071645, five pages, dated Nov. 10, 2015.
Artursson et al. "Correlation between oral drug absorption in humans and app arent drug permeability coefficients in human intestinal epithelial (CACO-2) cells" Biochem. Biophys. Res. Comm. 175:880-885 (1991).
Berge et al. "Pharmaceutical salts" J. Pharmaceut. Sci. 66:1-19 (1977).
Cheng et al. "Relationship between the inhibition constant (K1) and the concentration of inhibitor which causes 50 per cent inhibition ($I_{50}$) of an enzymatic reaction" Biochem. Pharmacol. 22:3099-3108 (1973).
Corey et al. "Useful procedures for the oxidation of alcohols involving pyridinium dichromate in aprotic media" Tetrahedron Lett. 5:399-402 (1979).
Dess et al. "Readily accessible 12-1-51 oxidant for the conversion of primary and secondary alcohols to aldehydes and ketones" J. Org. Chem. 48:4155-4156 (1983).
Illarionov et al. "Sequence of the cDNA encoding the $Ca^{2+}$-activated photoprotein obelin from the hydroid polyp *Obelia longissima*" Gene 153:273-274 (1995).
Li et al. "Controlled and cardiac-restricted overexpression of the arginine vasopressin V1A receptor causes reversible left ventricular dysfunction through $G\alpha_q$-mediated cell signaling" Circulation 124:572-581 (2011).

(Continued)

*Primary Examiner* — Bruck Kifle
(74) *Attorney, Agent, or Firm* — Nixon & Vanderhye P.C.

(57) ABSTRACT

The invention relates to substituted pyridobenzazepine and pyridobenzazocine derivatives and to processes for preparation thereof, and also to the use thereof for production of medicaments for treatment and/or prophylaxis of diseases, especially of cardiovascular disorders, preferably thrombotic or thromboembolic disorders, and oedemas, and also ophthalmic disorders.

15 Claims, No Drawings

(56) References Cited

OTHER PUBLICATIONS

Milligan et al. "$G_{16}$ as a universal G protein adapter: Implications for agonist screening strategies" Trends Pharmacol. Sci. 17:235-237 (1996).
Noble et al. "The effect of pressure on some sterically hindered solvolysis reactions" J. Org. Chem. 35:3588-3589 (1970).
Omura et al. "Oxidation of alcohols by 'activated' dimethyl sulfoxide. A preparative, steric and mechanistic study" Tetrahedron 34:1651-1660 (1978).
Rizzuto et al. "Rapid changes of mitochondrial $Ca^{2+}$ revealed by specifically targeted recombinant aequorin" Nature 358:325-327 (1992).
Santillan et al. "Vasopressin in preeclampsia a novel very early human pregnancy biomarker and clinically relevant mouse model" Hypertension 64:852-859 (2014).
Taveau et al. "Vasopressin and hydration play a major role in the development of glucose intolerance and hepatic steatosis in obese rats" Diabetologia 58:1081-1090 (2015).
Thibonnier et al. "Characterization of human platelet vasopressin receptors" J. Clin. Invest 76:1857-1864 (1985).
Ward et al. "Synthesis of (−)-bactobolin from D-glucose and from (+)-actinobol" Tetrahedron Lett. 35:3485-3488 (1994).
Wasilewski et al. "Arginine vasopressin receptor signaling and functional outcomes in heart failure" Cell. Signalling 28:224-233 (2016).
An International Search Report dated Nov. 10, 2015, in a corresponding International Application No. PCT/EP2015/071645 (9 pages), and an English Translation thereof (5 pages).

FACTOR XIA-INHIBITING PYRIDOBENZAZEPINE AND PYRIDOBENZAZOCINE DERIVATIVES

This application is the U.S. national phase of International Application No. PCT/EP2015/071645, filed 22 Sep. 2015, which designated the U.S. and claims priority to Patent Application No. EP 14186080.9, filed 24 Sep. 2014; the entire contents of each of which are hereby incorporated by reference.

The invention relates to substituted pyridobenzazepine and pyridobenzazocine derivatives and to processes for preparation thereof, and also to the use thereof for production of medicaments for treatment and/or prophylaxis of diseases, especially of cardiovascular disorders, preferably thrombotic or thromboembolic disorders, and oedemas, and also ophthalmic disorders.

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a final joint reaction path, are distinguished. Here, factors Xa and IIa (thrombin) play key roles: Factor Xa bundles the signals of the two coagulation paths since it is formed both via factor VIIa/tissue factor (extrinsic path) and via the tenase complex (intrinsic path) by conversion of factor X. The activated serine protease Xa cleaves prothrombin to thrombin which, via a series of reactions, transduces the impulses from the cascade to the coagulation state of the blood.

In the more recent past, the traditional theory of two separate regions of the coagulation cascade (extrinsic and intrinsic path) has been modified owing to new findings: In these models, coagulation is initiated by binding of activated factor VIIa to tissue factor (TF). The resulting complex activates factor X, which in turn leads to generation of thrombin with subsequent production of fibrin and platelet activation (via PAR-1) as injury-sealing end products of haemostasis. Compared to the subsequent amplification/propagation phase, the thrombin production rate in this first phase is low and as a result of the occurrence of TFPI as inhibitor of the TF-FVIIa-FX complex is limited in time.

A central component of the transition from initiation to amplification and propagation of coagulation is factor XIa: in positive feedback loops, thrombin activates, in addition to factor V and factor VIII, also factor XI to factor XIa, whereby factor IX is converted into factor IXa, and, via the factor IXa/factor VIIIa complex generated in this manner, the factor X is activated and thrombin formation is in turn therefore highly stimulated leading to strong thrombus growth and stabilizing the thrombus.

In addition, it becomes the focus that, in addition to the stimulation via tissue factor, the coagulation system can be activated particularly on negatively charged surfaces, which include not only surface structures of foreign cells (e.g. bacteria) but also artificial surfaces such as vascular prostheses, stents and extracoporeal circulation. On the surface, initially factor XII (FXII) is activated to factor XIIa which subsequently activates factor XI, attached to cell surfaces, to factor XIa. This leads to further activation of the coagulation cascade as described above. In addition, factor XIIa also activates bound plasma prokallikrein to plasma kallikrein (PK) which, in a potentiation loop, firstly leads to further factor XII activation, overall resulting in amplification of the initiation of the coagulation cascade. In addition, PK is an important bradykinin-releasing protease which, inter alia, thus leads to increased endothelial permeability. Further substrates that have been described are prorenin and prourokinase, whose activation may influence the regulatory processes of the renin-angiotensin system and fibrinolysis. The activation of PK is therefore an important link between coagulative and inflammatory processes.

Uncontrolled activation of the coagulation system or defective inhibition of the activation processes may lead to the formation of local thromboses or embolisms in vessels (arteries, veins, lymph vessels) or cardiac cavities. In addition, systemic hypercoagulability may lead to system-wide formation of thrombi and finally to consumption coagulopathy in the context of a disseminated intravasal coagulation. Thromboembolic complications may also occur in extracorporeal circulatory systems such as during haemodialysis and also in vascular prostheses or prosthetic heart valves and stents.

In the course of many cardiovascular and metabolic disorders, there is an increased tendency for coagulation and platelet activation owing to systemic factors such as hyperlipidaemia, diabetes or smoking, owing to changes in blood flow with stasis, for example in atrial fibrillation, or owing to pathological changes in vessel walls, for example endothelial dysfunctions or atherosclerosis. This unwanted and excessive activation of coagulation may, by formation of fibrin- and platelet-rich thrombi, lead to thromboembolic disorders and thrombotic complications with life-threatening conditions. Inflammable processes may also be involved here. Accordingly, thromboembolic disorders are still one of the most frequent causes of morbidity and mortality in most industrialized countries.

The anticoagulants known from the prior art, that is to say substances for inhibiting or preventing blood coagulation, have various disadvantages. Accordingly, in practice, efficient treatment methods or the prophylaxis of thrombotic/thromboembolic disorders is found to be very difficult and unsatisfactory.

In the therapy and prophylaxis of thromboembolic disorders, use is made, firstly, of heparin which is administered parenterally or subcutaneously. Because of more favourable pharmacokinetic properties, preference is these days increasingly given to low-molecular-weight heparin; however, the known disadvantages described hereinbelow encountered in heparin therapy cannot be avoided either in this manner. Thus, heparin is orally ineffective and has only a comparatively short half-life. In addition, there is a high risk of bleeding, there may in particular be cerebral haemorrhages and bleeding in the gastrointestinal tract, and there may be thrombopaenia, alopecia medicamentosa or osteoporosis. Low-molecular-weight heparins do have a lower probability of leading to the development of heparin-induced thrombocytopaenia; however, they can also only be administered subcutaneously. This also applies to fondaparinux, a synthetically produced selective factor Xa inhibitor having a long half-life.

A second class of anticoagulants are the vitamin K antagonists. These include, for example, 1,3-indanediones and in particular compounds such as warfarin, phenprocoumon, dicumarol and other coumarin derivatives which nonselectively inhibit the synthesis of various products of certain vitamin K-dependent coagulation factors in the liver. Owing to the mechanism of action, the onset of action is only very slow (latency to the onset of action 36 to 48 hours). The compounds can be administered orally; however, owing to the high risk of bleeding and the narrow therapeutic index complicated individual adjustment and monitoring of the patient are required. In addition, other side-effects such as gastrointestinal problems, hair loss and skin necroses have been described.

More recent approaches for oral anticoagulants are in various phases of clinical evaluation or in clinical use, and have demonstrated their effectiveness in various studies. However, taking these medicaments can also lead to bleeding complications, particularly in predisposed patients. Thus, for antithrombotic medicaments, the therapeutic window is of central importance: The interval between the therapeutically active dose for coagulation inhibition and the dose where bleeding may occur should be as large as possible so that maximum therapeutic activity is achieved at a minimum risk profile.

In various in vitro and in vivo models with, for example, antibodies as factor XIa inhibitors, but also in factor XIa knock-out models, the antithrombotic effect with small/no prolongation of bleeding time or extension of blood volume was confirmed. In clinical studies, elevated factor XIa concentrations were associated with an increased event rate. In contrast, factor XI deficiency (haemophilia C) did not lead to spontaneous bleeding and was apparent only in the course of surgical operations and traumata, but did show protection with respect to certain thromboembolic events.

In addition, plasma kallikrein (PK) is associated with other disorders, which are associated with increased vascular permeability or chronic inflammatory disorders such as is the case in diabetic retinopathy, macular oedema and hereditary angiooedema or chronic inflammatory intestinal disorders. Diabetic retinopathy is primarily caused by microvascular deficiency, which leads to basal membrane thickening of the vessels and loss of vascularized pericytes followed by vascular occlusion and retinal ischaemia which, owing to the retinal hypoxia thus caused, may lead to enhanced vessel permeability with subsequent formation of a macular oedema and, due to all of the processes present, to the patient going blind. In hereditary angiooedema (HAE), reduced formation of the physiological kallikrein inhibitor C1-esterase inhibitor causes uncontrolled plasma kallikrein activation and hence inflammations with fulminant oedema formation and severe pain. From experimental animal models, there are indications that inhibition of plasma kallikrein inhibits increased vascular permeability and may therefore prevent formation of a macular oedema and/or diabetic retinopathy or may improve the acute symptoms of HAE. Oral plasma kallikrein inhibitors could also be used for prophylaxis of HAE.

The kinins generated by means of plasma kallikrein especially have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

Furthermore, for many disorders the combination of antithrombotic and antiinflammatory principles may also be particularly attractive to prevent the mutual enhancement of coagulation and inflammation.

It is therefore an object of the present invention to provide novel compounds for the treatment of cardiovascular disorders, in particular of thrombotic or thromboembolic disorders, and/or oedematous disorders, and/or ophthalmic disorders, in particular diabetic retinopathy and/or macular oedema, in humans and animals, which compounds have a wide therapeutic bandwidth.

WO 2006/030032 describes inter alia substituted pyridinones as allosteric modulators of the mGluR2 receptor, and WO 2008/079787 describes substituted pyridin-2-ones and their use as glucokinase activators. WO 2014/154794, WO 2014/160592, WO 2015/011087 and WO 2015/063093 describe substituted pyridin-2-ones and their use as factor XIa inhibitors.

The invention provides compounds of the formula

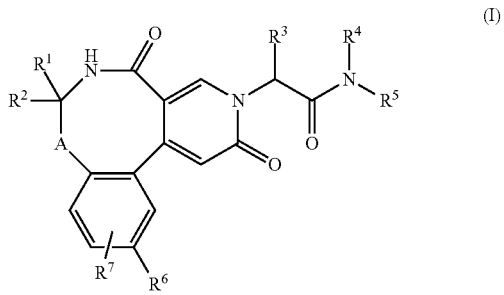

in which
A is a bond or —CH$_2$—,
R$^1$ is hydrogen or methyl,
  where methyl may be substituted by a fluorine substituent,
R$^2$ is hydrogen or methyl,
or
R$^1$ and R$^2$ together with the carbon atom to which they are bonded form a cyclopropyl ring,
R$^3$ is hydrogen, C$_1$-C$_5$-alkyl, C$_1$-C$_4$-alkoxy, difluoromethyl, trifluoromethyl, 1,1-difluoroethyl, 3,3,3-trifluoro-2-hydroxyprop-1-yl, 3,3,3-trifluoro-2-methoxyprop-1-yl, 3,3,3-trifluoro-2-ethoxyprop-1-yl, prop-2-yn-1-yl, cyclopropyloxy or cyclobutyloxy,
  where alkyl may be substituted by a substituent selected from the group consisting of fluorine, cyano, hydroxyl, difluoromethyl, trifluoromethyl, methoxy, ethoxy, difluoromethoxy, trifluoromethoxy, C$_3$-C$_6$-cycloalkyl, 4- to 6-membered oxoheterocyclyl, 1,4-dioxanyl, oxazolyl, phenyl and pyridyl,
    in which cycloalkyl may be substituted by 1 to 2 substituents selected independently from the group consisting of fluorine, hydroxyl, methyl, ethyl, methoxy, ethoxy, difluoromethyl, trifluoromethyl, difluoromethoxy and trifluoromethoxy,
R$^4$ is hydrogen,
R$^5$ is a group of the formula

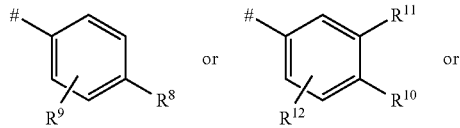

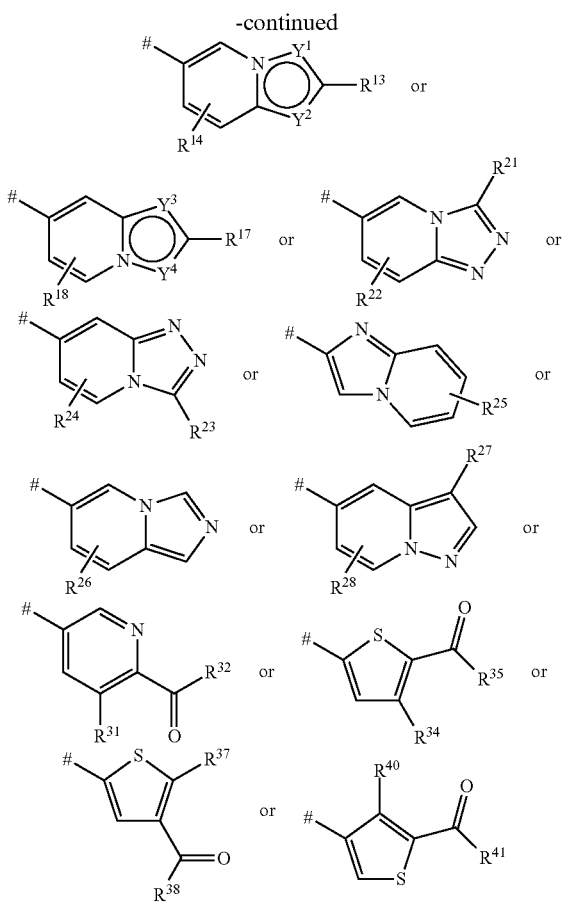

where # is the attachment point to the nitrogen atom,
R$^8$ is hydroxycarbonyl, aminocarbonyl or 5-membered heterocyclyl,
where heterocyclyl may be substituted by 1 to 2 substituents selected independently from the group consisting of oxo, hydroxyl, thioxo, sulphanyl, methyl, difluoromethyl, trifluoromethyl, 2-hydroxycarbonyl-1,1,2,2-tetrafluoroethyl and 2-methoxycarbonyl-1,1,2,2-tetrafluoroethyl,
in which methyl may be substituted by a methoxy substituent,
R$^9$ is hydrogen, chlorine, fluorine or methyl,
R$^{10}$ and R$^{11}$ together with the carbon atoms to which they are bonded form a 5-membered heterocycle,
where the heterocycle may be substituted by 1 to 2 substituents selected independently from the group consisting of oxo, chlorine, hydroxyl, hydroxycarbonyl, methyl, difluoromethyl, trifluoromethyl, 1,1,2,2,2-pentafluoroethyl, 2-hydroxycarbonyl-1,1,2,2-tetrafluoroethyl and 2-methoxycarbonyl-1,1,2,2-tetrafluoroethyl,
R$^{12}$ is hydrogen, chlorine, fluorine, methyl or methoxy,
Y$^1$ is a nitrogen atom or C—R$^{15}$
in which
R$^{15}$ is hydrogen, chlorine, hydroxyl, methoxy or C$_1$-C$_3$-alkoxycarbonyl,
Y$^2$ is a nitrogen atom or C—R$^{16}$
in which
R$^{16}$ is hydrogen, chlorine, hydroxyl or methoxy,
R$^{13}$ is hydrogen, hydroxycarbonyl, hydroxycarbonylmethyl or phenyl, where phenyl may be substituted by 1 to 2 fluorine substituents,
R$^{14}$ is hydrogen, chlorine, fluorine or methyl,
Y$^3$ is a nitrogen atom or C—R$^{19}$
in which
R$^{19}$ is hydrogen, chlorine, hydroxyl or methoxy,
Y$^4$ is a nitrogen atom or C—R$^{20}$
in which
R$^{20}$ is hydrogen, chlorine, hydroxyl or methoxy,
R$^{17}$ is hydrogen, hydroxycarbonyl, hydroxycarbonylmethyl, C$_1$-C$_3$-alkoxycarbonyl or aminocarbonyl,
R$^{18}$ is hydrogen, chlorine, fluorine or methyl,
R$^{21}$ is hydrogen, chlorine, hydroxyl, C$_1$-C$_4$-alkyl, methoxy, C$_1$-C$_3$-alkylaminomethyl or morpholinylmethyl,
R$^{22}$ is hydrogen, chlorine, fluorine or methyl,
R$^{23}$ is hydrogen, chlorine, hydroxyl or methoxy,
R$^{24}$ is hydrogen, chlorine, fluorine or methyl,
R$^{25}$ is hydrogen, hydroxycarbonyl or hydroxycarbonylmethyl,
R$^{26}$ is hydrogen, chlorine, fluorine or methyl,
R$^{27}$ is hydroxycarbonyl, aminocarbonyl, C$_1$-C$_3$-alkoxycarbonyl or C$_1$-C$_3$-alkylaminocarbonyl,
where alkylaminocarbonyl may be substituted by a substituent selected from the group consisting of hydroxyl, trifluoromethyl, methoxy and trifluoromethoxy,
R$^{28}$ is hydrogen, chlorine, fluorine or methyl,
R$^{31}$ is hydrogen or fluorine,
R$^{32}$ is hydroxyl or —NHR$^{33}$,
in which
R$^{33}$ is hydrogen, methyl or ethyl,
R$^{34}$ is hydrogen or fluorine,
R$^{35}$ is hydroxyl or —NHR$^{36}$,
in which
R$^{36}$ is hydrogen, methyl or ethyl,
R$^{37}$ is hydrogen or fluorine,
R$^{38}$ is hydroxyl or —NHR$^{39}$,
in which
R$^{39}$ is hydrogen, methyl or ethyl,
R$^{40}$ is hydrogen or fluorine,
R$^{41}$ is hydroxyl or —NHR$^{42}$,
in which
R$^{42}$ is hydrogen, methyl or ethyl,
R$^6$ is bromine, chlorine, fluorine, methyl, difluoromethyl, trifluoromethyl, methoxy, difluoromethoxy or trifluoromethoxy,
R$^7$ is hydrogen, chlorine or fluorine,
and the salts thereof, the solvates thereof and the solvates of the salts thereof.

Compounds of the invention are the compounds of the formula (I) and the salts, solvates and solvates of the salts thereof, and also the compounds encompassed by formula (I) and specified hereinafter as working example(s), and the salts, solvates and solvates of the salts thereof, to the extent that the compounds encompassed by formula (I) and specified hereinafter are not already salts, solvates and solvates of the salts.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, especially HPLC chromatography on an achiral or chiral phase.

If the compounds according to the invention can occur in tautomeric forms, the present invention encompasses all the tautomeric forms.

The present invention also encompasses all suitable isotopic variants of the compounds according to the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labeled with $^{3}H$ or $^{14}C$ isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described further down and the procedures described in the working examples, by using corresponding isotopic modifications of the respective reagents and/or starting compounds.

Preferred salt in the context of the present invention are physiologically acceptable salts of the compounds according to the invention. However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates in the context of the invention are described as those forms of the compounds according to the invention which form a complex in the solid or liquid state by coordination with solvent molecules. Hydrates are a specific form of the solvates in which the coordination is with water.

The present invention additionally also encompasses prodrugs of the compounds according to the invention. The term "prodrugs" encompasses compounds which for their part may be biologically active or inactive but are converted during their residence time in the body to compounds according to the invention (for example by metabolism or hydrolysis).

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, unless specified otherwise, the substituents are defined as follows:

Alkyl is a straight-chain or branched alkyl radical having 1 to 5 carbon atoms, preferably 1 to 3 carbon atoms, by way of example and with preference methyl, ethyl, n-propyl, isopropyl, 2-methylprop-1-yl, n-butyl, tert-butyl and 2,2-dimethylprop-1-yl.

Alkoxy is a straight-chain or branched alkoxy radical having 1 to 4 carbon atoms, preferably 1 to 3 carbon atoms, by way of example and with preference methoxy, ethoxy, n-propoxy, isopropoxy, 2-methylprop-1-oxy, n-butoxy and tert-butoxy.

Alkoxycarbonyl is a straight-chain or branched alkoxy radical attached via a carbonyl group and having 1 to 3 carbon atoms, preferably 1 to 2 carbon atoms, for example and with preference methoxycarbonyl, ethoxycarbonyl, n-propoxycarbonyl and isopropoxycarbonyl.

Alkylaminocarbonyl is an amino group having one or two independently selected, identical or different, straight-chain or branched alkyl substituents each having 1 to 3 carbon atoms, bonded via a carbonyl group, for example and with preference methylaminocarbonyl, ethylaminocarbonyl, n-propylaminocarbonyl, isopropylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl and N,N-diisopropylaminocarbonyl. $C_1$-$C_3$-Alkylaminocarbonyl is, for example, a monoalkylaminocarbonyl radical having 1 to 3 carbon atoms or a dialkylaminocarbonyl radical having 1 to 3 carbon atoms in each alkyl substituent.

Alkylaminomethyl is an amino group having one or two independently selected, identical or different, straight-chain or branched alkyl substituents each having 1 to 3 carbon atoms, bonded via a methyl group, for example and with preference methylaminomethyl, ethylaminomethyl, n-propylaminomethyl, isopropylaminomethyl, N,N-dimethylaminomethyl, N,N-diethylaminomethyl, N-ethyl-N-methylaminomethyl, N-methyl-N-n-propylaminomethyl, N-isopropyl-N-n-propylaminomethyl and N,N-diisopropylaminomethyl. $C_1$-$C_3$-Alkylaminomethyl is, for example, a monoalkylaminomethyl radical having 1 to 3 carbon atoms or a dialkylaminomethyl radical having in each case 1 to 3 carbon atoms in each alkyl substituent.

Cycloalkyl is a monocyclic cycloalkyl group having 3 to 6 carbon atoms; illustrative and preferred examples of cycloalkyl include cyclopropyl, cyclobutyl, cyclopentyl and cyclohexyl.

5-Membered heterocyclyl in the definition of the $R^8$ radical is a saturated, partly unsaturated or aromatic monocyclic radical having 5 ring atoms and up to 4 heteroatoms from the group of S, O and N, where a nitrogen atom may also form an N-oxide, by way of example and with preference thienyl, furyl, pyrrolyl, thiazolyl, oxazolyl, isoxazolyl, oxadiazolyl, thiadiazolyl, pyrazolyl, imidazolyl, triazolyl, tetrazolyl, dihydrooxazolyl and dihydroimidazolyl.

5-Membered heterocycle in the definition of the $R^{10}$ and $R^{11}$ radicals is a saturated, partly unsaturated or aromatic monocyclic radical having 5 ring atoms and up to 2 heteroatoms from the group consisting of S, O and N, where a nitrogen atom may also form an N-oxide. This 5-membered heterocycle together with the phenyl ring to which it is bonded is, by way of example and with preference, 2,3-dihydro-1-benzothiophen-5-yl, 1,3-dihydro-2-benzothiophen-5-yl, 2,3-dihydro-1-benzofuran-5-yl, 1,3-dihydro-2-benzofuran-5-yl, indolin-5-yl, isoindolin-5-yl, 2,3-dihydro-1H-indazol-5-yl, 2,3-dihydro-1H-benzimidazol-5-yl, 1,3-dihydro-2,1-benzoxazol-5-yl, 2,3-dihydro-1,3-benzoxazol-5-yl, 1,3-dihydro-2,1-benzothiazol-5-yl, 2,3-dihydro-1,3-benzothiazol-5-yl, 1H-benzimidazol-5-yl, 1H-indazol-5-yl, 1,2-benzoxazol-5-yl, indol-5-yl, isoindol-5-yl, benzofuran-5-yl, benzothiophen-5-yl, 2,3-dihydro-1-benzothiophen-6-yl, 1,3-dihydro-2-benzothiophen-6-yl, 2,3-dihydro-1-benzofuran-6-yl, 1,3-dihydro-2-benzofuran-6-yl, indolin-6-yl, isoindolin-6-yl, 2,3-dihydro-1H-indazol-6-yl, 2,3-dihydro-1H-benzimidazol-6-yl, 1,3-dihydro-2,1-benzoxazol-6-yl, 2,3-dihydro-1,3-benzoxazol-6-yl, 1,3-dihydro-2,1-benzothiazol-6-yl, 2,3-dihydro-1,3-benzothiazol-6-yl, 1H-benzimidazol-6-yl, 1H-indazol-6-yl, 1,2-benzoxazol-6-yl, indol-6-yl, isoindol-6-yl, benzofuran-6-yl and benzothiophen-6-yl.

4- to 6-membered oxoheterocyclyl in the definition of the $R^3$ radical is a saturated monocyclic radical having 4 to 6 ring atoms in which one ring atom is an oxygen atom, by way of example and with preference oxetanyl, tetrahydrofuranyl and tetrahydro-2H-pyranyl.

In the formulae of the group that $R^5$ can represent, the end point of the line marked by # in each case is not a carbon atom or a $CH_2$ group, but is part of the bond to the atom to which $R^5$ is attached.

Preference is given to compounds of the formula (I) in which
A is a bond or —$CH_2$—,
$R^1$ is hydrogen or methyl,
$R^2$ is hydrogen or methyl,
or
$R^1$ and $R^2$ together with the carbon atom to which they are bonded form a cyclopropyl ring,
$R^3$ is hydrogen, C1-$C_5$-alkyl, $C_1$-$C_4$-alkoxy, difluoromethyl, trifluoromethyl, 1,1-difluoroethyl, 3,3,3-trifluoro-2-hydroxyprop-1-yl, 3,3,3-trifluoro-2-methoxyprop-1-yl, 3,3,3-trifluoro-2-ethoxyprop-1-yl, prop-2-yn-1-yl, cyclopropyloxy or cyclobutyloxy, where alkyl may be substituted by a substituent selected from the group consisting of fluorine, cyano, hydroxyl, difluoromethyl, trifluoromethyl, methoxy, ethoxy, difluoromethoxy, trifluoromethoxy, $C_3$-$C_6$-cycloalkyl, 4- to 6-membered oxoheterocyclyl, 1,4-dioxanyl, oxazolyl, phenyl and pyridyl,
   in which cycloalkyl may be substituted by 1 to 2 substituents selected independently from the group consisting of fluorine, hydroxyl, methyl, ethyl, methoxy, ethoxy, difluoromethyl, trifluoromethyl, difluoromethoxy and trifluoromethoxy,
$R^4$ is hydrogen,
$R^5$ is a group of the formula

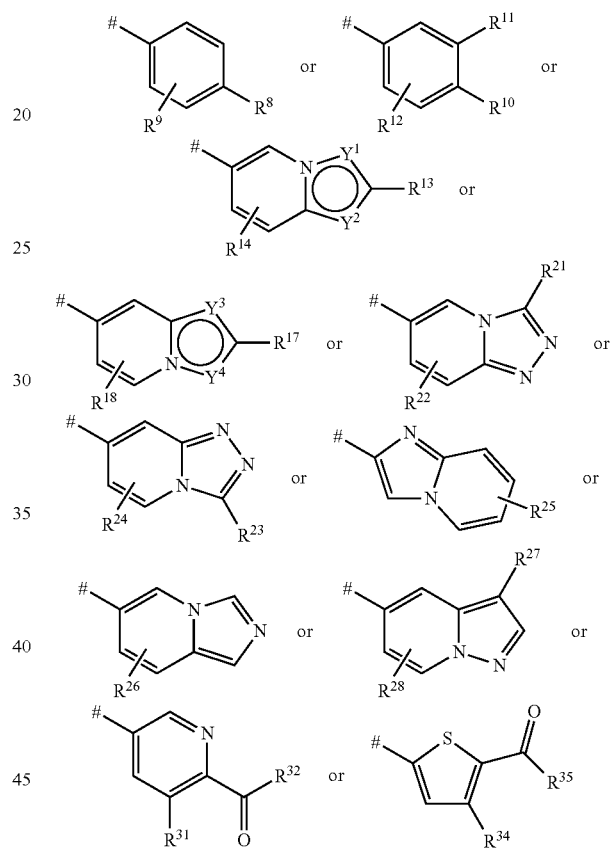

where # is the attachment point to the nitrogen atom,
$R^8$ is hydroxycarbonyl, aminocarbonyl or 5-membered heterocyclyl,
   where heterocyclyl may be substituted by 1 to 2 substituents selected independently from the group consisting of oxo, hydroxyl, thioxo, sulphanyl, methyl, difluoromethyl, trifluoromethyl, 2-hydroxycarbonyl-1,1,2,2-tetrafluoroethyl and 2-methoxycarbonyl-1,1,2,2-tetrafluoroethyl,
   in which methyl may be substituted by a methoxy substituent,
$R^9$ is hydrogen, chlorine, fluorine or methyl,
$R^{10}$ and $R^{11}$ together with the carbon atoms to which they are bonded form a 5-membered heterocycle,
   where the heterocycle may be substituted by 1 to 2 substituents selected independently from the group consisting of oxo, chlorine, hydroxyl, hydroxycarbonyl, methyl, difluoromethyl, trifluoromethyl, 1,1, 2,2,2-pentafluoroethyl, 2-hydroxycarbonyl-1,1,2,2-tetrafluoroethyl and 2-methoxycarbonyl-1,1,2,2-tetrafluoroethyl, $R^{12}$ is hydrogen, chlorine, fluorine, methyl or methoxy, $Y^1$ is a nitrogen atom or C—$R^{15}$
in which
$R^{15}$ is hydrogen, chlorine, hydroxyl, methoxy or $C_1$-$C_3$-alkoxycarbonyl, $Y^2$ is a nitrogen atom or C—$R^{16}$
in which
$R^{16}$ is hydrogen, chlorine, hydroxyl or methoxy, $R^{13}$ is hydrogen, hydroxycarbonyl, hydroxycarbonylmethyl or phenyl,
where phenyl may be substituted by 1 to 2 fluorine substituents, $R^{14}$ is hydrogen, chlorine, fluorine or methyl, $Y^3$ is a nitrogen atom or C—$R^{19}$
in which
$R^{19}$ is hydrogen, chlorine, hydroxyl or methoxy, $Y^4$ is a nitrogen atom or C—$R^{20}$
in which
$R^{20}$ is hydrogen, chlorine, hydroxyl or methoxy, $R^{17}$ is hydrogen, hydroxycarbonyl, hydroxycarbonylmethyl, $C_1$-$C_3$-alkoxycarbonyl or aminocarbonyl, $R^{18}$ is hydrogen, chlorine, fluorine or methyl, $R^{21}$ is hydrogen, chlorine, hydroxyl, $C_1$-$C_4$-alkyl, methoxy, $C_1$-$C_3$-alkylaminomethyl or morpholinylmethyl, $R^{22}$ is hydrogen, chlorine, fluorine or methyl, $R^{23}$ is hydrogen, chlorine, hydroxyl or methoxy, $R^{24}$ is hydrogen, chlorine, fluorine or methyl, $R^{25}$ is hydrogen, hydroxycarbonyl or hydroxycarbonylmethyl, $R^{26}$ is hydrogen, chlorine, fluorine or methyl, $R^{27}$ is hydroxycarbonyl, aminocarbonyl, $C_1$-$C_3$-alkoxycarbonyl or $C_1$-$C_3$-alkylaminocarbonyl,
where alkylaminocarbonyl may be substituted by a substituent selected from the group consisting of hydroxyl, trifluoromethyl, methoxy and trifluoromethoxy, $R^{28}$ is hydrogen, chlorine, fluorine or methyl, $R^{31}$ is hydrogen or fluorine, $R^{32}$ is hydroxyl or —NHR$^{33}$,
in which
$R^{33}$ is hydrogen, methyl or ethyl, $R^{34}$ is hydrogen or fluorine, $R^{35}$ is hydroxyl or —NHR$^{36}$,
in which
$R^{36}$ is hydrogen, methyl or ethyl, $R^6$ is bromine, chlorine, fluorine, methyl, difluoromethyl, trifluoromethyl, methoxy, difluoromethoxy or trifluoromethoxy, $R^7$ is hydrogen, chlorine or fluorine, and the salts thereof, the solvates thereof and the solvates of the salts thereof.

Preferred compounds of the formula (I) are also those in which

A is a bond or —CH$_2$—, $R^1$ is hydrogen or methyl, $R^2$ is hydrogen or methyl,
or
$R^1$ and $R^2$ together with the carbon atom to which they are bonded form a cyclopropyl ring, $R^3$ is hydrogen, methyl, ethyl, n-propyl, 2-methylprop-1-yl, n-butyl or ethoxy,
where methyl may be substituted by a substituent selected from the group consisting of difluoromethyl, trifluoromethyl, cyclopropyl, cyclobutyl, cyclohexyl, oxetanyl, tetrahydrofuranyl, tetrahydro-2H-pyranyl and 1,4-dioxanyl,
where cyclopropyl, cyclobutyl, cyclohexyl and oxetanyl may be substituted by 1 to 2 substituents selected independently from the group consisting of fluorine, hydroxyl, methyl, ethyl and methoxy,
and
where ethyl, n-propyl and n-butyl may be substituted by a substituent selected from the group consisting of fluorine, methoxy and trifluoromethoxy, $R^4$ is hydrogen, $R^5$ is a group of the formula

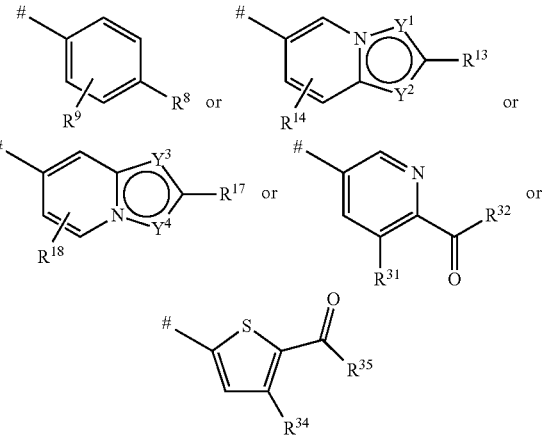

where # is the attachment point to the nitrogen atom, $R^8$ is hydroxycarbonyl, aminocarbonyl, oxazolyl, oxadiazolyl, thiadiazolyl, pyrazolyl, imidazolyl, triazolyl, tetrazolyl or dihydrooxazolyl,
where oxazolyl, oxadiazolyl, thiadiazolyl, pyrazolyl, imidazolyl, triazolyl and dihydrooxazolyl may be substituted by 1 to 2 substituents selected independently from the group consisting of oxo, hydroxyl, thioxo, sulphanyl, methyl, trifluoromethyl and 2-hydroxycarbonyl-1,1,2,2-tetrafluoroethyl,
in which methyl may be substituted by a methoxy substituent, $R^9$ is hydrogen, chlorine, fluorine or methyl, $Y^1$ is a nitrogen atom or C—$R^{15}$
in which
$R^{15}$ is hydrogen, chlorine, hydroxyl or methoxy, $Y^2$ is a nitrogen atom or C—$R^{16}$
in which
$R^{16}$ is hydrogen, chlorine, hydroxyl or methoxy, $R^{13}$ is hydrogen or hydroxycarbonyl, $R^{14}$ is hydrogen or fluorine, $Y^3$ is a nitrogen atom or C—$R^{19}$
in which
$R^{19}$ is hydrogen, chlorine, hydroxyl or methoxy, $Y^4$ is a nitrogen atom or C—$R^{20}$
in which
$R^{20}$ is hydrogen, chlorine, hydroxyl or methoxy, $R^{17}$ is hydrogen or hydroxycarbonyl, $R^{18}$ is hydrogen or fluorine, $R^{31}$ is hydrogen, $R^{32}$ is hydroxyl or —NHR$^{33}$, in which
R³³ is hydrogen,
R³⁴ is hydrogen,
R³⁵ is hydroxyl,
or
R⁵ is 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl, 1H-indazol-5-yl or 2H-indazol-5-yl,
   where the 5-membered heterocycle in 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl, 1H-indazol-5-yl and 2H-indazol-5-yl may be substituted by 1 to 2 substituents independently selected from the group consisting of oxo, chlorine, hydroxycarbonyl, methyl and trifluoromethyl,
   and
   where the benzyl ring in 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl and 1H-indazol-5-yl may be substituted by a substituent selected from the group consisting of fluorine and methoxy.
R⁶ is chlorine,
R⁷ is hydrogen,
and the salts thereof, the solvates thereof and the solvates of the salts thereof.

Preferred compounds of the formula (I) are also those in which
A is a bond or —CH₂—,
R¹ is hydrogen,
R² is hydrogen,
or
R¹ and R² together with the carbon atom to which they are bonded form a cyclopropyl ring,
R³ is hydrogen, ethyl or 2-methylprop-1-yl,
   where ethyl may be substituted by a methoxy substituent,
R⁴ is hydrogen,
R⁵ is a group of the formula

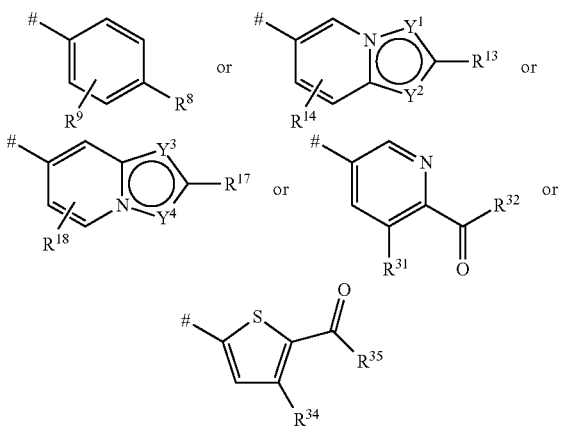

where # is the attachment point to the nitrogen atom,
R⁸ is hydroxycarbonyl, aminocarbonyl or oxadiazolyl,
   where oxadiazolyl may be substituted by an oxo substituent,
R⁹ is hydrogen or fluorine,
Y¹ is C—R¹⁵,
   in which
      R¹⁵ is hydrogen,
Y² is a nitrogen atom,
R¹³ is hydrogen,
R¹⁴ is hydrogen,
Y³ is C—R¹⁹,
   in which
      R¹⁹ is hydrogen,
Y⁴ is a nitrogen atom,
R¹⁷ is hydrogen,
R¹⁸ is hydrogen,
R³¹ is hydrogen,
R³² is hydroxyl or —NHR³³,
   in which
      R³³ is hydrogen,
R³⁴ is hydrogen,
R³⁵ is hydroxyl,
or
R⁵ is 2,3-dihydro-1H-indazol-6-yl, 2,3-dihydro-1H-benzimidazol-5-yl, 1H-indazol-5-yl or 2H-indazol-5-yl,
   where the 5-membered heterocycle in 2,3-dihydro-1H-indazol-6-yl, 2,3-dihydro-1H-benzimidazol-5-yl, 1H-indazol-5-yl and 2H-indazol-5-yl may be substituted by 1 to 2 substituents selected independently from the group consisting of oxo and methyl.
R⁶ is chlorine,
R⁷ is hydrogen,
and the salts thereof, the solvates thereof and the solvates of the salts thereof.

Preference is also given to compounds of the formula (I) in which R¹ and R² are hydrogen.

Preference is also given to compounds of the formula in which R¹ and R² together with the carbon atom to which they are bonded form a cyclopropyl ring.

Preferred compounds of the formula (I) are also those in which
R³ is hydrogen, ethyl or 2-methylprop-1-yl,
   where ethyl may be substituted by a methoxy substituent.

Preferred compounds of the formula (I) are also those in which
R⁵ is a group of the formula

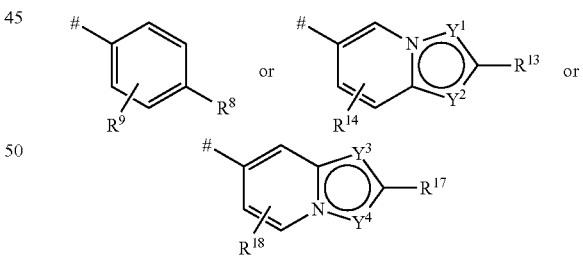

where # is the attachment point to the nitrogen atom,
R⁸ is hydroxycarbonyl, aminocarbonyl or oxadiazolyl,
   where oxadiazolyl may be substituted by an oxo substituent,
R⁹ is hydrogen or fluorine,
Y¹ is C—R¹⁵,
   in which
      R¹⁵ is hydrogen,
Y² is a nitrogen atom,
R¹³ is hydrogen,
R¹⁴ is hydrogen,
Y³ is C—R¹⁹, in which $R^{19}$ is hydrogen, $Y^4$ is a nitrogen atom, $R^{17}$ is hydrogen, $R^{18}$ is hydrogen.

Preferred compounds of the formula (I) are also those in which $R^5$ is a group of the formula

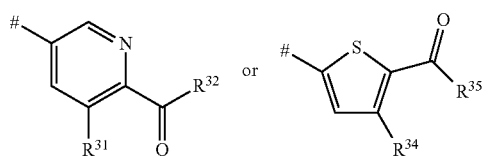

where # is the attachment point to the nitrogen atom, $R^{31}$ is hydrogen, $R^{32}$ is hydroxyl or —NHR$^{33}$, in which $R^{33}$ is hydrogen, $R^{34}$ is hydrogen, $R^{35}$ is hydroxyl.

Preferred compounds of the formula (I) are also those in which $R^5$ is 2,3-dihydro-1H-indazol-6-yl, 2,3-dihydro-1H-benzimidazol-5-yl, 1H-indazol-5-yl or 2H-indazol-5-yl, where the 5-membered heterocycle in 2,3-dihydro-1H-indazol-6-yl, 2,3-dihydro-1H-benzimidazol-5-yl, 1H-indazol-5-yl and 2H-indazol-5-yl may be substituted by 1 to 2 substituents selected independently from the group consisting of oxo and methyl.

Preference is also given to compounds of the formula (I) in which $R^6$ is chlorine.

Preference is also given to compounds of the formula (I) in which $R^7$ is hydrogen.

Preference is also given to compounds of the formula (Ia)

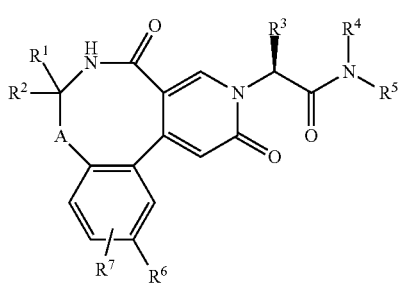

in which A, $R^1$, $R^2$, $R^3$, $R^4$, $R^5$, $R^6$ and $R^7$ are as defined above.

The invention further provides a process for preparing the compounds of the formula (I), or the salts thereof, solvates thereof or the solvates of the salts thereof, wherein

[A] the compounds of the formula

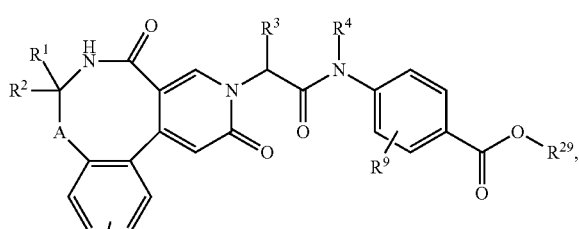

in which

A, $R^1$, $R^2$, $R^3$, $R^4$, $R^6$, $R^7$ and $R^9$ have the definition given above, and $R^{29}$ is tert-butyl are reacted with an acid to give compounds of the formula

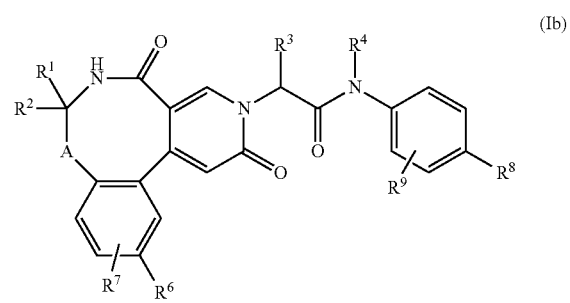

in which

A, $R^1$, $R^2$, $R^3$, $R^4$, $R^6$, $R^7$ and $R^9$ have the definition given above, and $R^8$ is hydroxycarbonyl, or

[B] the compounds of the formula

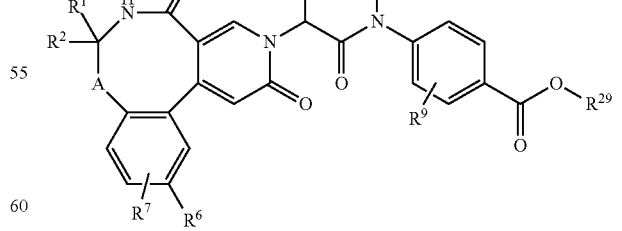

in which

A, $R^1$, $R^2$, $R^3$, $R^4$, $R^6$, $R^7$ and $R^9$ have the definition given above, and $R^{29}$ is methyl or ethyl are reacted with a base to give compounds of the formula

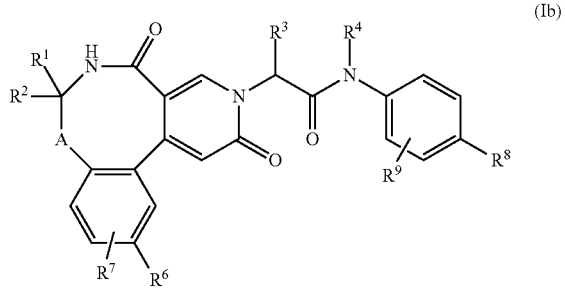

(Ib)

in which
A, $R^1$, $R^2$, $R^3$, $R^4$, $R^6$, $R^7$ and $R^9$ have the definition given above, and
$R^8$ is hydroxycarbonyl,
or
[C] the compounds of the formula

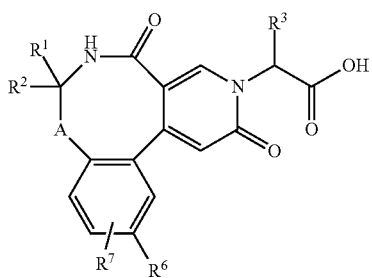

(III)

in which
A, $R^1$, $R^2$, $R^3$, $R^6$ and $R^7$ have the definition given above
are reacted with compounds of the formula

(IV)

in which
$R^4$ and $R^5$ have the definition given above,
in the presence of a dehydrating reagent to give compounds of the formula (I).

The compounds of the formula (Ib) are a subset of the compounds of the formula (I).

The compounds of the formulae (IIa) and (IIb) together form the group of the compounds of the formula (II).

The reaction according to process [A] is generally carried out in inert solvents, preferably in a temperature range from room temperature to 60° C. at atmospheric pressure.

Inert solvents are, for example, halogenated hydrocarbons such as dichloromethane, trichloromethane, carbon tetrachloride or 1,2-dichloroethane, or ethers such as tetrahydrofuran or dioxane, preference being given to dichloromethane.

Acids are, for example, trifluoroacetic acid or hydrogen chloride in dioxane, preference being given to trifluoroacetic acid.

The reaction according to process [B] is generally carried out in inert solvents, preferably in a temperature range from room temperature up to reflux of the solvents at atmospheric pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to a mixture of tetrahydrofuran and water, a mixture of methanol and water or a mixture of ethanol and water.

Bases are, for example, alkali metal hydroxides such as sodium hydroxide, lithium hydroxide or potassium hydroxide, or alkali metal carbonates such as caesium carbonate, sodium carbonate or potassium carbonate, or alkoxides such as potassium tert-butoxide or sodium tert-butoxide, preference being given to lithium hydroxide or caesium carbonate.

The reaction according to process [C] is generally carried out in inert solvents, if appropriate in the presence of a base, preferably in a temperature range from 0° C. to room temperature at atmospheric pressure.

Examples of suitable dehydrating reagents here include carbodiimides, for example N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide), or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), (benzotriazol-1-yloxy)bisdimethyl-aminomethylium fluoroborate (TBTU) or O-(7-azabenzotriazol-1-yl)-N,N,N,N'-tetramethyluronium hexafluorophosphate (HATU), or 1-hydroxybenzotriazole (HOBt), or benzotriazol-1-yloxytris(dimethylamino)phosphonium hexafluorophosphate (BOP), or ethyl hydroxyiminocyanoacetate (Oxyma), or (1-cyano-2-ethoxy-2-oxoethylideneaminooxy)dimethylaminomorpholinocarbenium hexafluorophosphate (COMU), or N-[(dimethylamino)(3H-[1,2,3]triazolo[4,5-b]pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, with bases. The condensation is preferably conducted with HATU or with T3P.

Bases are, for example, alkali metal carbonates such as sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or diisopropylethylamine, or pyridine. The condensation is preferably conducted with diisopropylethylamine or pyridine.

Inert solvents are, for example, halogenated hydrocarbons such as dichloromethane or trichloromethane, hydrocarbons such as benzene, or other solvents such as nitromethane, dioxane, dimethylformamide, dimethyl sulphoxide or acetonitrile. It is also possible to use mixtures of the solvents. Particular preference is given to dimethylformamide.

The compounds of the formula (IV) are known, can be synthesized from the corresponding starting compounds by known processes or can be prepared analogously to the processes described in the Examples section.

The compounds of the formula (II) are known or can be prepared by reacting compounds of the formula

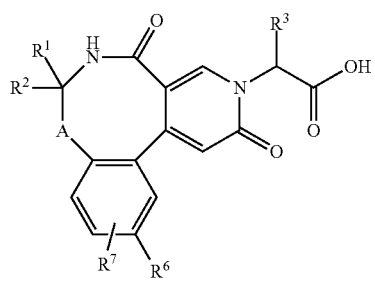

(III)

in which
A, $R^1$, $R^2$, $R^3$, $R^6$ and $R^7$ have the definition given above
with compounds of the formula

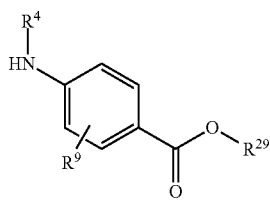

(V)

in which
$R^4$ and $R^9$ have the definition given above, and
$R^{29}$ is methyl, ethyl or tert-butyl,
in the presence of a dehydrating reagent.

The reaction is carried out as described for process [C].

The compounds of the formula (V) are known, can be synthesized from the corresponding starting compounds by known processes or can be prepared analogously to the processes described in the Examples section.

The compounds of the formula (III) are known or can be prepared by reacting compounds of the formula

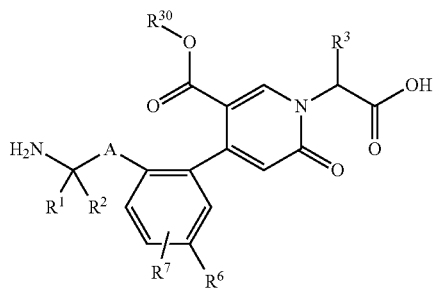

(VI)

in which
A, $R^1$, $R^2$, $R^3$, $R^6$ and $R^7$ have the definition given above, and
$R^{30}$ is methyl or ethyl,
with a base.

The reaction is generally effected in inert solvents, if appropriate in the presence of molecular sieve, preferably in a temperature range from room temperature to 50° C. at standard pressure.

Inert solvents are, for example alcohols such as methanol or ethanol, ethers such as dioxane or tetrahydrofuran, or mixtures of solvents, preference being given to tetrahydrofuran.

Bases are, for example, sodium hydride or alkoxides such as potassium ethoxide or sodium ethoxide or potassium methoxide or sodium methoxide, preference being given to sodium ethoxide.

The compounds of the formula (VI) are known or can be prepared by reacting compounds of the formula

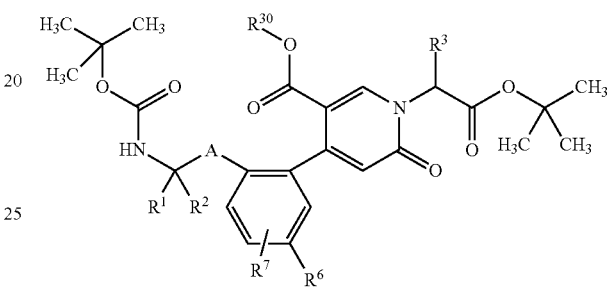

(VII)

in which
A, $R^1$, $R^2$, $R^3$, $R^6$ and $R^7$ have the definition given above, and
$R^{30}$ is methyl or ethyl,
with an acid.

The reaction is effected as described for process [A].

The compounds of the formula (VII) are known or can be prepared by reacting compounds of the formula

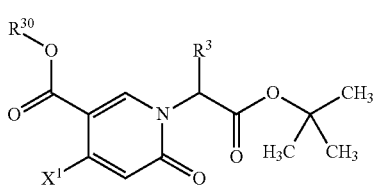

(VIII)

in which
$R^3$ has the definition given above,
$R^{30}$ is methyl or ethyl, and
$X^1$ is chlorine, bromine, iodine or trifluoromethanesulphonyloxy
with compounds of the formula

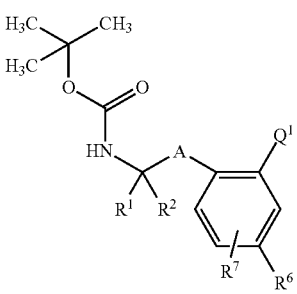

(IX)

in which

A, $R^1$, $R^2$, $R^6$ and $R^7$ are as defined above, and $Q^1$ is —B(OH)$_2$, a boronic ester, preferably pinacol boronate, or —BF$_3^-$K$^+$, under Suzuki coupling conditions to give compounds of the formula (VII).

The reaction is generally effected in inert solvents, in the presence of a catalyst, optionally in the presence of an additional reagent, optionally in a microwave, preferably within a temperature range from room temperature to 150° C. at standard pressure to 3 bar.

Catalysts are, for example, palladium catalysts customary for Suzuki reaction conditions, preference being given to catalysts such as dichlorobis(triphenylphosphine)palladium, tetrakistriphenylphosphinepalladium(0), palladium(II) acetate/triscyclohexylphosphine, tris(dibenzylideneacetone)dipalladium, bis(diphenylphosphaneferrocenyl)palladium (II) chloride, 1,3-bis(2,6-diisopropylphenyl)imidazol-2-ylidene(1,4-naphthoquinone)palladium dimer, allyl(chloro)(1,3-dimesityl-1,3-dihydro-2H-imidazol-2-ylidene) palladium, palladium(II) acetate/dicyclohexyl(2',4',6'-triisopropylbiphenyl-2-yl)phosphine, [1,1-bis(diphenylphosphino)ferrocene]palladium(II) chloride monodichloromethane adduct or XPhos precatalyst [(2'-aminobiphenyl-2-yl)(chloro)palladium dicyclohexyl(2',4',6'-triisopropylbiphenyl-2-yl)phosphane (1:1)], preference being given to tetrakistriphenylphosphinepalladium(0), [1,1-bis-(diphenylphosphino)ferrocene]palladium(II) chloride monodichloromethane adduct or XPhos precatalyst [(2'-aminobiphenyl-2-yl)(chloro)palladium dicyclohexyl(2', 4',6'-triisopropylbiphenyl-2-yl)phosphane (1:1)].

Additional reagents are, for example, potassium acetate, caesium carbonate, potassium carbonate or sodium carbonate, potassium tert-butoxide, caesium fluoride or potassium phosphate, where these may be present in aqueous solution; preferred are additional reagents such as potassium carbonate or aqueous potassium phosphate solution.

Inert solvents are, for example, ethers such as dioxane, tetrahydrofuran or 1,2-dimethoxyethane, hydrocarbons such as benzene, xylene or toluene, or carboxamides such as dimethylformamide or dimethylacetamide, alkyl sulphoxides such as dimethyl sulphoxide, or N-methylpyrrolidone or acetonitrile, or mixtures of the solvents with alcohols such as methanol or ethanol and/or water; preference is given to tetrahydrofuran, dioxane or acetonitrile.

The compounds of the formulae (VIII) and (IX) are known, can be synthesized from the corresponding starting compounds by known processes or can be prepared analogously to the processes described in the Examples section.

The preparation of the starting compounds and of the compounds of the formula (I) can be illustrated by the synthesis scheme below.

Scheme 1:

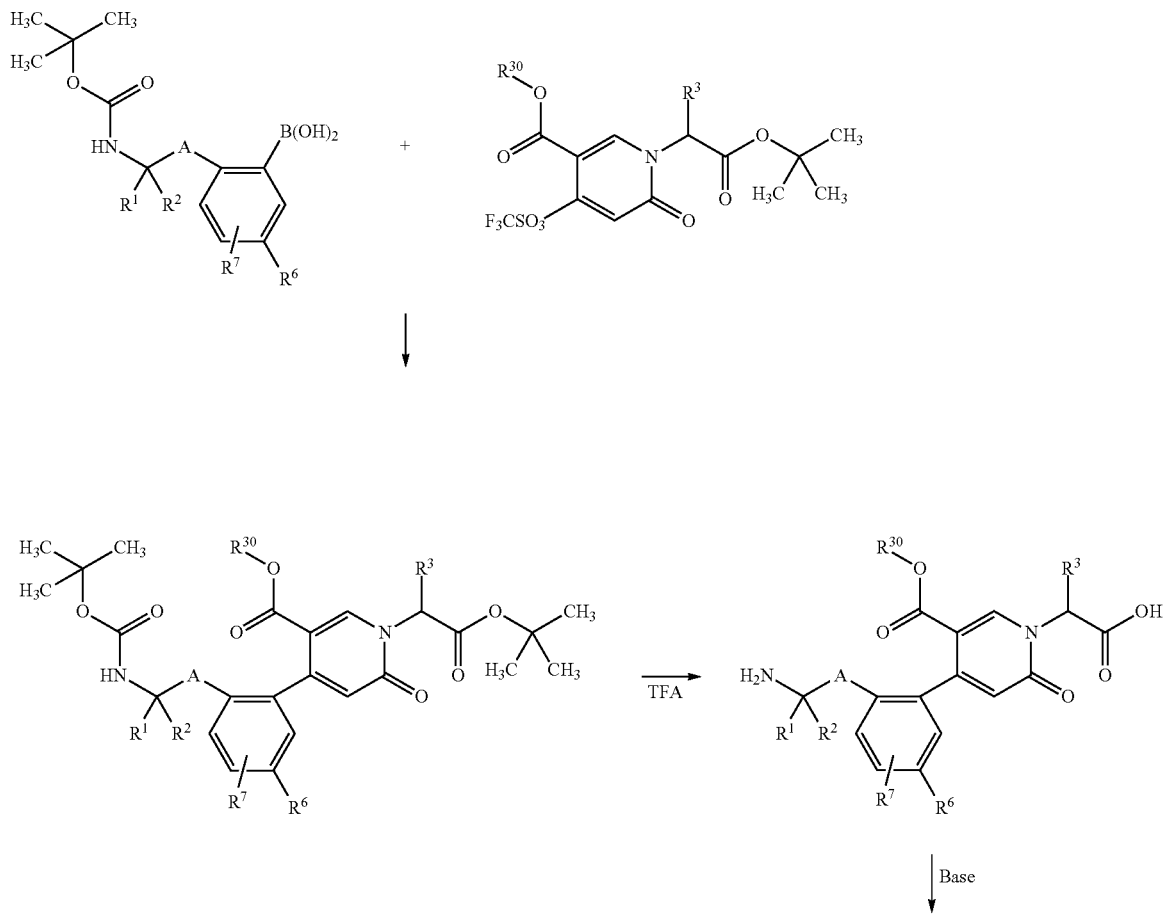

-continued

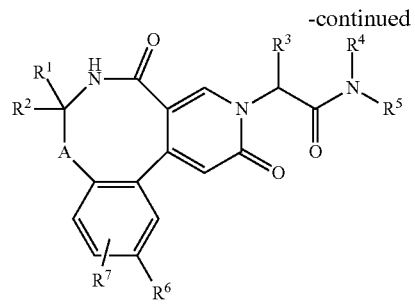 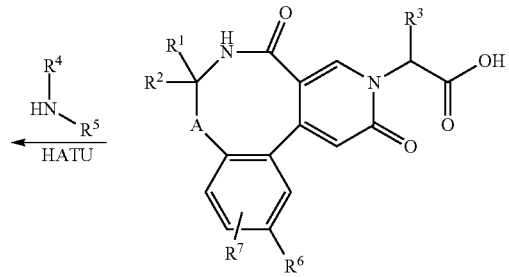

The compounds according to the invention have an unforeseeable useful pharmacological activity spectrum and good pharmacokinetic characteristics. They are compounds that influence the proteolytic activity of the serine protease factor XIa (FXIa) and/or the serine protease plasma kallikrein (PK). The compounds according to the invention inhibit the enzymatic cleavage of substrates, catalysed by FXIa and/or PK, which have essential roles in the activation of blood coagulation, in the aggregation of blood platelets via reduction of the thrombin necessary for the PAR-1 activation of the platelets, and in inflammatory processes, which particularly involve an increase in vascular permeability.

They are therefore suitable for use as medicaments for the treatment and/or prophylaxis of diseases in humans and animals.

The present invention further provides for the use of the compounds according to the invention for the treatment and/or prophylaxis of disorders, in particular cardiovascular disorders, preferably thrombotic or thromboembolic disorders and/or thrombotic or thromboembolic complications, and/or ophthalmic disorders, in particular of diabetic retinopathy or macular oedema, and/or inflammatory disorders, in particular those associated with excess plasma kallikrein activity, such as hereditary angiooedema (HAE) or chronic inflammatory disorders, particularly of the intestine such as Crohn's disease.

Factor XIa (FXIa) is an important enzyme in the context of coagulation, which can be activated both by thrombin and factor XIIa (FXIIa), and is therefore involved in two essential processes of coagulation: It is a central component of the transition from initiation to amplification and propagation of coagulation: in positive feedback loops, thrombin activates, in addition to factor V and factor VIII, also factor XI to factor XIa, whereby factor IX is converted into factor IXa, and, via the factor IXa/factor VIIIa complex generated in this manner, the factor X is activated and thrombin formation is in turn therefore highly stimulated, leading to strong thrombus growth and stabilizing the thrombus.

Moreover, factor XIa is an important component for the intrinsic initiation of coagulation: In addition to the stimulation via tissue factor (TF), the coagulation system can be activated also particularly on negatively charged surfaces, which include not only surface structures of foreign cells (e.g. bacteria) but also artificial surfaces such as vascular prostheses, stents and extracorporeal circulation. On the surface, initially factor XII (FXII) is activated to factor XIIa (FXIIA) which subsequently activates FXI, attached to cell surfaces, to FXIa. This leads to further activation of the coagulation cascade as described above.

In contrast, thrombin generation in the initiation phase remains uninfluenced via TF/factor VIIa and factor X activation and finally thrombin formation, the physiological reaction on vascular injuries. This could explain why no prolongations of bleeding times were found in FXIa knockout mice, as in rabbits and other species, with administration of FXIa inhibitor. This low bleeding tendency caused by the substance is of great advantage for use in humans, particularly in patients with increased risk of bleeding.

In addition, factor XIIa also activates plasma prokallikrein to plasma kallikrein (PK) in the context of the intrinsic activation which, inter alia, in a potentiation loop, leads to further factor XII activation, overall resulting in amplification of the initiation of the coagulation cascade on surfaces. A PK-inhibiting activity of a compound according to the invention thus reduces coagulation via surface activation and thus has an anticoagulatory effect. An advantage could be in the combination of factor XIa inhibitory activity and PK inhibitory activity allowing a balanced antithrombotic effect.

Accordingly, the compounds according to the invention are suitable for the treatment and/or prophylaxis of disorders or complications which may arise from the formation of clots.

For the purpose of the present invention, the "thrombotic or thromboembolic disorders" include disorders which occur both in the arterial and in the venous vasculature and which can be treated with the compounds according to the invention, in particular disorders in the coronary arteries of the heart, such as acute coronary syndrome (ACS), myocardial infarction with ST segment elevation (STEMI) and without ST segment elevation (non-STEMI), stable angina pectoris, unstable angina pectoris, reocclusions and restenoses after coronary interventions such as angioplasty, stent implantation or aortocoronary bypass, but also thrombotic or thromboembolic disorders in further vessels leading to peripheral arterial occlusive disorders, pulmonary embolisms, venous thromboembolisms, venous thromboses, in particular in deep leg veins and kidney veins, transitory ischaemic attacks and also thrombotic stroke and thromboembolic stroke.

Stimulation of the coagulation system may occur by various causes or associated disorders. In the context of surgical interventions, immobility, confinement to bed, infections, inflammation or cancer or cancer therapy, inter alia, the coagulation system can be highly activated, and there may be thrombotic complications, in particular venous thromboses. The compounds according to the invention are therefore suitable for the prophylaxis of thromboses in the context of surgical interventions in patients suffering from cancer. The compounds according to the invention are therefore also suitable for the prophylaxis of thromboses in patients having an activated coagulation system, for example in the stimulation situations described.

The inventive compounds are therefore also suitable for the prevention and treatment of cardiogenic thromboembolisms, for example brain ischaemias, stroke and systemic thromboembolisms and ischaemias, in patients with acute, intermittent or persistent cardiac arrhythmias, for example atrial fibrillation, and in patients undergoing cardioversion, and also in patients with heart valve disorders or with artificial heart valves.

In addition, the inventive compounds are suitable for the treatment and prevention of disseminated intravascular coagulation (DIC) which may occur in connection with sepsis inter alia, but also owing to surgical interventions, neoplastic disorders, burns or other injuries and may lead to severe organ damage through microthromboses.

Thromboembolic complications furthermore occur in microangiopathic haemolytical anaemias and by the blood coming into contact with foreign surfaces in the context of extracorporeal circulation, for example haemodialysis, ECMO ("extracorporeal membrane oxygenation"), LVAD ("left ventricular assist device") and similar methods, AV fistulas, vascular and heart valve prostheses.

Moreover, the compounds according to the invention are suitable for the treatment and/or prophylaxis of disorders involving microclot formation or fibrin deposits in cerebral blood vessels which may lead to dementia disorders such as vascular dementia or Alzheimer's disease. Here, the clot may contribute to the disorder both via occlusions and by binding further disease-relevant factors.

Moreover, the compounds according to the invention are suitable in particular for the treatment and/or prophylaxis of disorders where, in addition to the pro-coagulant component, the pro-inflammatory component also plays an essential role. Mutual enhancement of coagulation and inflammation in particular can be prevented by the compounds according to the invention, thus decisively lowering the probability of thrombotic complications. In this case, both the factor XIa-inhibitory component (via inhibition of thrombin production) and the PK-inhibitory component can contribute to the anticoagulant and antiinflammatory effect (e.g. via bradykinin). Therefore, the treatment and/or prophylaxis in the context of atherosclerotic vascular disorders, inflammations in the context of rheumatic disorders of the locomotor system, inflammatory disorders of the lung, such as pulmonary fibroses, inflammatory disorders of the kidney, such as glomerulonephritides, inflammatory disorders of the intestine, such as Crohn's disease or ulcerative colitis, or disorders which may be present in the context of a diabetic underlying disease, such as diabetic retinopathy or nephropathy, may be considered, inter alia.

Kinins generated by means of plasma kallikrein, inter alia, have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

Moreover, the compounds according to the invention can be used for inhibiting tumour growth and the formation of metastases, and also for the prophylaxis and/or treatment of thromboembolic complications, for example venous thromboembolisms, for tumour patients, in particular those undergoing major surgical interventions or chemo- or radiotherapy.

In addition, the inventive compounds are also suitable for the prophylaxis and/or treatment of pulmonary hypertension.

In the context of the present invention, the term "pulmonary hypertension" includes pulmonary arterial hypertension, pulmonary hypertension associated with disorders of the left heart, pulmonary hypertension associated with pulmonary disorders and/or hypoxia and pulmonary hypertension owing to chronic thromboembolisms (CTEPH).

"Pulmonary arterial hypertension" includes idiopathic pulmonary arterial hypertension (IPAH, formerly also referred to as primary pulmonary hypertension), familial pulmonary arterial hypertension (FPAH) and associated pulmonary arterial hypertension (APAH), which is associated with collagenoses, congenital systemic-pulmonary shunt vitia, portal hypertension, HIV infections, the ingestion of certain drugs and medicaments, with other disorders (thyroid disorders, glycogen storage disorders, Morbus Gaucher, hereditary teleangiectasia, haemoglobinopathies, myeloproliferative disorders, splenectomy), with disorders having a significant venous/capillary contribution, such as pulmonary-venoocclusive disorder and pulmonary-capillary haemangiomatosis, and also persisting pulmonary hypertension of neonatants.

Pulmonary hypertension associated with disorders of the left heart includes a diseased left atrium or ventricle and mitral or aorta valve defects.

Pulmonary hypertension associated with pulmonary disorders and/or hypoxia includes chronic obstructive pulmonary disorders, interstitial pulmonary disorder, sleep apnoea syndrome, alveolar hypoventilation, chronic high-altitude sickness and inherent defects.

Pulmonary hypertension owing to chronic thromboembolisms (CTEPH) comprises the thromboembolic occlusion of proximal pulmonary arteries, the thromboembolic occlusion of distal pulmonary arteries and non-thrombotic pulmonary embolisms (tumour, parasites, foreign bodies).

The present invention further provides for the use of the inventive compounds for production of medicaments for the treatment and/or prophylaxis of pulmonary hypertension associated with sarcoidosis, histiocytosis X and lymphangiomatosis.

In addition, the substances according to the invention are also useful for the treatment of pulmonary and hepatic fibroses.

In addition, the compounds according to the invention are also suitable for the treatment and/or prophylaxis of disseminated intravascular coagulation in the context of an infectious disease, and/or of systemic inflammatory syndrome (SIRS), septic organ dysfunction, septic organ failure and multiorgan failure, acute respiratory distress syndrome (ARDS), acute lung injury (ALI), septic shock and/or septic organ failure.

In the course of an infection, there may be a generalized activation of the coagulation system (disseminated intravascular coagulation or consumption coagulopathy, hereinbelow referred to as "DIC") with microthrombosis in various organs and secondary haemorrhagic complications. Moreover, there may be endothelial damage with increased permeability of the vessels and diffusion of fluid and proteins into the extravasal space. As the infection progresses, there may be failure of an organ (for example kidney failure, liver failure, respiratory failure, central-nervous deficits and cardiovascular failure) or multiorgan failure.

In the case of DIC, there is a massive activation of the coagulation system at the surface of damaged endothelial cells, the surfaces of foreign bodies or crosslinked extravascular tissue. As a consequence, there is coagulation in small vessels of various organs with hypoxia and subsequent organ dysfunction. A secondary effect is the consumption of coagulation factors (for example factor X, prothrombin and fibrinogen) and platelets, which reduces the coagulability of the blood and may result in heavy bleeding.

Compounds according to the invention which inhibit plasma kallikrein alone or in combination with factor XIa, are also useful for the treatment and/or prophylaxis of disorders in the course of which plasma kallikrein is involved. In addition to the anticoagulant activity, plasma kallikrein is an important bradikinin-releasing protease which, inter alia, thus leads to increased endothelial permeability. The compounds can therefore be used for the treatment and/or prophylaxis of disorders involving oedema formations such as ophthalmic disorders, in particular, diabetic retinopathy or macular oedema or hereditary angiooedema.

"Ophthalmic disorders" in the context of the present invention include in particular disorders such as diabetic retinopathy, diabetic macular oedema (DME), macular oedema, macular oedema associated with retinal vein occlusion, age-related macular degeneration (AMD), choroidal neovascularization (CNV), choroidal neovascular membranes (CNVM), cystoid macular oedema (CME), epiretinal membranes (ERM) and macular perforations, myopia-associated choroidal neovascularization, angioid streaks, vascular streaks, retina detachment, atrophic changes of the retinal pigment epithelium, hypertrophic changes of the retinal pigment epithelium, retinal vein occlusion, choroidal retinal vein occlusion, retinitis pigmentosa, Stargardt's disease, retinopathy of prematurity, glaucoma, inflammatory eye disorders such as uveitis, scleritis or endophthalmitis, cataract, refraction anomalies such as myopia, hyperopia or astigmatism and keratoconus, disorders of the anterior eye such as corneal angiogenesis as sequela of, for example, keratitis, cornea transplantation or keratoplasty, corneal angiogenesis as sequela of hypoxia (for example by excessive use of contact lenses), pterygium conjunctivae, subcorneal oedema and intracorneal oedema.

The compounds according to the invention are also suitable for the primary prophylaxis of thrombotic or thromboembolic disorders and/or inflammatory disorders and/or disorders with increased vascular permeability in patients in which gene mutations lead to enhanced activity of the enzymes, or increased levels of the zymogens and these are established by relevant tests/measurements of the enzyme activity or zymogen concentrations.

The present invention further provides for the use of the compounds according to the invention for the treatment and/or prophylaxis of disorders, especially the disorders mentioned above.

The present invention further provides for the use of the compounds according to the invention for production of a medicament for the treatment and/or prophylaxis of disorders, especially the disorders mentioned above.

The present invention further provides a method for the treatment and/or prophylaxis of disorders, especially the disorders mentioned above, using a therapeutically effective amount of a compound according to the invention.

The present invention further provides the compounds according to the invention for use in a method for the treatment and/or prophylaxis of disorders, especially the disorders mentioned above, using a therapeutically effective amount of a compound according to the invention.

The present invention further provides medicaments comprising a compound according to the invention and one or more further active ingredients.

In addition, the compounds according to the invention can also be used for preventing coagulation ex vivo, for example for the protection of organs to be transplanted against organ damage caused by formation of clots and for protecting the organ recipient against thromboemboli from the transplanted organ, for preserving blood and plasma products, for cleaning/pretreating catheters and other medical auxiliaries and instruments, for coating synthetic surfaces of medical auxiliaries and instruments used in vivo or ex vivo or for biological samples which may comprise factor XIa or plasma kallikrein.

The present invention furthermore provides a method for preventing the coagulation of blood in vitro, in particular in banked blood or biological samples which may comprise factor XIa or plasma kallikrein or both enzymes, which method is characterized in that an anticoagulatory effective amount of the compound according to the invention is added.

The present invention further provides medicaments comprising a compound according to the invention and one or more further active ingredients, in particular for the treatment and/or prophylaxis of the disorders mentioned above. Preferred examples of active ingredients suitable for combinations include:

lipid-lowering substances, especially HMG-CoA (3-hydroxy-3-methylglutaryl-coenzyme A) reductase inhibitors, for example lovastatin (Mevacor), simvastatin (Zocor), pravastatin (Pravachol), fluvastatin (Lescol) and atorvastatin (Lipitor);

coronary therapeutics/vasodilatators, especially ACE (angiotensin converting enzyme) inhibitors, for example captopril, lisinopril, enalapril, ramipril, cilazapril, benazepril, fosinopril, quinapril and perindopril, or AII (angiotensin II) receptor antagonists, for example embusartan, losartan, valsartan, irbesartan, candesartan, eprosartan and temisartan, or β-adrenoceptor antagonists, for example carvedilol, alprenolol, bisoprolol, acebutolol, atenolol, betaxolol, carteolol, metoprolol, nadolol, penbutolol, pindolol, propanolol and timolol, or alpha-1-adrenoceptor antagonists, for example prazosine, bunazosine, doxazosine and terazosine, or diuretics, for example hydrochlorothiazide, furosemide, bumetanide, piretanide, torasemide, amiloride and dihydralazine, or calcium channel blockers, for example verapamil and diltiazem, or dihydropyridine derivatives, for example nifedipin (Adalat) and nitrendipine (Bayotensin), or nitro preparations, for example isosorbide 5-mononitrate, isosorbide dinitrate and glycerol trinitrate, or substances causing an increase in cyclic guanosine monophosphate (cGMP), for example stimulators of soluble guanylate cyclase, for example riociguat;

plasminogen activators (thrombolytics/fibrinolytics) and compounds which promote thrombolysis/fibrinolysis such as inhibitors of the plasminogen activator inhibitor (PAI inhibitors) or inhibitors of the thrombin-activated fibrinolysis inhibitor (TAFI inhibitors), for example tissue plasminogen activator (t-PA, for example Actilyse®), streptokinase, reteplase and urokinase or plasminogen-modulating substances causing increased formation of plasmin;

anticoagulatory substances (anticoagulants), for example heparin (UFH), low-molecular-weight heparins (LMW), for example tinzaparin, certoparin, pamaparin, nadroparin, ardeparin, enoxaparin, reviparin, dalteparin, danaparoid, semuloparin (AVE 5026), adomiparin (M118) and EP-42675/ORG42675;

direct thrombin inhibitors (DTI), for example Pradaxa (dabigatran), atecegatran (AZD-0837), DP-4088, SSR-182289A, argatroban, bivalirudin and tanogitran (BIBT-986 and prodrug BIBT-1011), hirudin;

direct factor Xa inhibitors, for example rivaroxaban, apixaban, edoxaban (DU-176b), betrixaban (PRT-54021), R-1663, darexaban (YM-150), otamixaban (FXV-673/RPR-130673), letaxaban (TAK-442), razaxaban (DPC-906), DX-9065a, LY-517717, tanogitran (BIBT-986, prodrug: BIBT-1011), idraparinux and fondaparinux, substances which inhibit the aggregation of platelets (platelet aggregation inhibitors, thrombocyte aggregation inhibitors), for example acetylsalicylic acid (for example aspirin), P2Y12 antagonists, for example ticlopidine (Ticlid), clopidogrel (Plavix), prasugrel, ticagrelor, cangrelor, elinogrel, PAR-1 antagonists, for example vorapaxar, PAR-4 antagonists, EP3 antagonists, for example DG041;

platelet adhesion inhibitors such as GPVI and/or GPIb antagonists, for example Revacept or caplacizumab;

fibrinogen receptor antagonists (glycoprotein-IIb/IIIa antagonists), for example abciximab, eptifibatide, tirofiban, lamifiban, lefradafiban and fradafiban;

recombinant human activated protein C, for example Xigris or recombinant thrombomodulin;

and also antiarrhythmics;

inhibitors of VEGF and/or PDGF signal paths, for example aflibercept, ranibizumab, bevacizumab, KH-902, pegaptanib, ramucirumab, squalamin or bevasiranib, apatinib, axitinib, brivanib, cediranib, dovitinib, lenvatinib, linifanib, motesanib, pazopanib, regorafenib, sorafenib, sunitinib, tivozanib, vandetanib, vatalanib, Vargatef and E-10030;

inhibitors of angiopoietin-Tie signal paths, for example AMG386;

inhibitors of Tie2 receptor tyrosine kinase;

inhibitors of the integrin signal paths, for example volociximab, cilengitide and ALG1001;

inhibitors of the PI3K-Akt-mTor signal paths, for example XL-147, perifosine, MK2206, sirolimus, temsirolimus and everolimus;

corticosteroids, for example anecortave, betamethasone, dexamethasone, triamcinolone, fluocinolone and fluocinolone acetonide;

inhibitors of the ALK1-Smad1/5 signal path, for example ACE041;

cyclooxygenase inhibitors, for example bromfenac and nepafenac;

inhibitors of the kallikrein-kinin system, for example safotibant and ecallantide;

inhibitors of the sphingosine 1-phosphate signal paths, for example sonepcizumab;

inhibitors of the complement-C5a receptor, for example eculizumab;

inhibitors of the 5HT1a receptor, for example tandospirone;

inhibitors of the Ras-Raf-Mek-Erk signal path; inhibitors of the MAPK signal paths; inhibitors of the FGF signal paths; inhibitors of endothelial cell proliferation; apoptosis-inducing active ingredients;

photodynamic therapy consisting of an active ingredient and the action of light, the active ingredient being, for example, verteporfin.

"Combinations" for the purpose of the invention mean not only dosage forms which contain all the components (so-called fixed combinations) and combination packs which contain the components separate from one another, but also components which are administered simultaneously or sequentially, provided that they are used for the prophylaxis and/or treatment of the same disease. It is likewise possible to combine two or more active ingredients with one another, meaning that they are thus each in two-component or multicomponent combinations.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

Suitable administration forms for extraocular (topic) administration are those which operate in accordance with the prior art, which release the active ingredient rapidly and/or in a modified or controlled manner and which contain the active ingredient in crystalline and/or amorphized and/or dissolved form, for example eye drops, sprays and lotions (e.g. solutions, suspensions, vesicular/colloidal systems, emulsions, aerosols), powders for eye drops, sprays and lotions (e.g. ground active ingredient, mixtures, lyophilisates, precipitated active ingredient), semisolid eye preparations (e.g. hydrogels, in-situ hydrogels, creams and ointments), eye inserts (solid and semisolid preparations, e.g. bioadhesives, films/wafers, tablets, contact lenses).

Intraocular administration includes, for example, intravitreal, subretinal, subscleral, intrachoroidal, subconjunctival, retrobulbar and subtenon administration. Suitable administration forms for intraocular administration are those which operate in accordance with the prior art, which release the active ingredient rapidly and/or in a modified or controlled manner and which contain the active ingredient in crystalline and/or amorphized and/or dissolved form, for example preparations for injection and concentrates for preparations for injection (e.g. solutions, suspensions, vesicular/colloidal systems, emulsions), powders for preparations for injection (e.g. ground active ingredient, mixtures, lyophilisates, precipitated active ingredient), gels for preparations for injection (semisolid preparations, e.g. hydrogels, in-situ hydrogels) and implants (solid preparations, e.g. biodegradable and nonbiodegradable implants, implantable pumps).

Preference is given to oral administration or, in the case of ophthalmologic disorders, extraocular and intraocular administration.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds according to the invention can be converted to the administration forms mentioned. This can be accomplished in a manner known per se by mixing with inert, non-toxic, pharmaceutically suitable excipients. These auxiliaries include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctants.

The present invention further provides medicaments comprising at least one inventive compound, preferably together with one or more inert non-toxic pharmaceutically suitable auxiliaries, and the use thereof for the purposes mentioned above.

In the case of parenteral administration, it has generally been found to be advantageous to administer amounts of about 5 to 250 mg every 24 hours to achieve effective results. In the case of oral administration, the amount is about 5 to 500 mg every 24 hours.

In spite of this, it may be necessary, as the case may be, to deviate from the amounts specified, specifically depending on body weight, administration route, individual behaviour towards the active ingredient, type of formulation, and time or interval of administration.

Unless stated otherwise, the percentages in the tests and examples which follow are percentages by weight; parts are parts by weight. Solvent ratios, dilution ratios and concentration data for liquid/liquid solutions are based in each case on volume. "w/v" means "weight/volume". For example, "10% w/v" means: 100 ml of solution or suspension contain 10 g of substance.

A) EXAMPLES

Abbreviations

Boc tert-butyloxycarbonyl
ca. circa
d day(s), doublet (in NMR)
TLC thin-layer chromatography
DCM dichloromethane
DCI direct chemical ionization (in MS)
dd doublet of doublets (in NMR)
DIC N,N'-diisopropylcarbodiimide
DIEA N,N-diisopropylethylamine
DMAP 4-dimethylaminopyridine
DMF N,N-dimethylformamide
DMSO dimethyl sulphoxide
eq. equivalent(s)
ESI electrospray ionization (in MS)
h hour(s)
HATU O-(7-azabenzotriazol-1-yl)-N,N,N',N'-tetramethyluronium hexafluorophosphate
HPLC high-pressure, high-performance liquid chromatography
HV high vacuum
LC-MS liquid chromatography-coupled mass spectroscopy
LDA lithium diisopropylamide
m multiplet (in NMR)
min minute(s)
MS mass spectroscopy
NMR nuclear magnetic resonance spectroscopy
Oxyma ethyl cyano(hydroxyimino)acetate
q quartet or quadruplet (in NMR)
quant. quantitative
quin quintet (in NMR)
RP reversed phase (in HPLC)
RT room temperature
$R_t$ retention time (in HPLC)
s singlet (in NMR)
sxt sextet (in NMR)
SFC supercritical fluid chromatography (with supercritical carbon dioxide as mobile phase)
t triplet (in NMR)
THF tetrahydrofuran
TFA trifluoroacetic acid
T3P 2,4,6-tripropyl-1,3,5,2,4,6-trioxatriphosphinane 2,4,6-trioxide HPLC, LC-MS and GC Methods:

Method 1:
Instrument: Waters ACQUITY SQD UPLC System; column: Waters Acquity UPLC HSS T3 1.8µ 50 mm×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 2:
Instrument: Waters ACQUITY SQD UPLC System; column: Waters Acquity UPLC HSS T3 1.8µ 50 mm×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A; oven: 50° C.; flow rate: 0.35 ml/min; UV detection: 210-400 nm.

Method 3:
Instrument: Micromass Quattro Premier with Waters UPLC Acquity; column: Thermo Hypersil GOLD 1.9µ 50 mm×1 mm; eluent A: 1 l water+0.5 ml 50% formic acid, eluent B: 1 l acetonitrile+0.5 ml 50% formic acid; gradient: 0.0 min 97% A→0.5 min 97% A→3.2 min 5% A→4.0 min 5% A; oven: 50° C.; flow rate: 0.3 ml/min; UV detection: 210 nm.

Method 4:
MS instrument: Waters (Micromass) Quattro Micro; HPLC instrument: Agilent 1100 Series; column: YMC-Triart C18 3µ 50 mm×3 mm; eluent A: 1 l water+0.01 mol ammonium carbonate, eluent B: 1 l acetonitrile; gradient: 0.0 min 100% A→2.75 min 5% A→4.5 min 5% A; oven: 40° C.; flow rate: 1.25 ml/min; UV detection: 210 nm.

Method 5:
MS instrument: Waters (Micromass) QM; HPLC instrument: Agilent 1100 series; column: Agilent ZORBAX Extend-C18 3.0 mm×50 mm 3.5 micron; eluent A: 1 l water+0.01 mol ammonium carbonate, eluent B: 1 l acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 6:

MS instrument: Waters (Micromass) ZQ; HPLC instrument: Agilent 1100 series; column: Agilent ZORBAX Extend-C18 3.0 mm×50 mm 3.5 micron; eluent A: 1 l water+0.01 mol ammonium carbonate, eluent B: 1 l acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 7:

Instrument: Thermo DFS, Trace GC Ultra; column: Restek RTX-35, 15 m×200 µm×0.33 µm; constant flow rate of helium: 1.20 ml/min; oven: 60° C.; inlet: 220° C.; gradient: 60° C., 30° C./min→300° C. (hold for 3.33 min).

Method 8:

Instrument: Agilent MS Quad 6150; HPLC: Agilent 1290; column: Waters Acquity UPLC HSS T3 1.8µ 50 mm×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 9:

Instrument: Thermo Scientific DSQII, Thermo Scientific Trace GC Ultra; column: Restek RTX-35MS, 15 m×200 µm×0.33 µm; constant flow rate of helium: 1.20 ml/min; oven: 60° C.; inlet: 220° C.; gradient: 60° C., 30° C./min→300° C. (hold for 3.33 min).

Method 10:

Instrument MS: Waters SQD; Instrument HPLC: Waters UPLC; column: Zorbax SB-Aq (Agilent), 50 mm×2.1 mm, 1.8 µm; eluent A: water+0.025% formic acid, eluent B: acetonitrile+0.025% formic acid; gradient: 0.0 min 98% A→0.9 min 25% A→1.0 min 5% A→1.4 min 5% A→1.41 min 98% A→1.5 min 98% A; oven: 40° C.; flow rate: 0.60 ml/min; UV detection: DAD; 210 nm.

Method 11:

MS instrument: Waters (Micromass) Quattro Micro; instrument: Waters UPLC Acquity; column: Waters BEH C18 1.7µ, 50 mm×2.1 mm; eluent A: 1 l water+0.01 mol ammonium formate, eluent B: 1 l acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm.

Method 12:

MS instrument type Thermo Scientific FT-MS; UHPLC+ instrument type Thermo Scientific UltiMate 3000; column Waters, HSST3, 2.1 mm×75 mm, C18 1.8 µm; eluent A 1 l of water+0.01% formic acid; eluent B 1 l of acetonitrile+ 0.01% formic acid; gradient 0.0 min 10% B→2.5 min 95% B→3.5 min 95% B; oven 50° C.; flow rate 0.90 ml/min; UV detection 210 nm/optimum integration path 210-300 nm Method 13:

GC/MS measurements: OV-1 column, column length 50 m, internal diameter 0.25 mm, film thickness 0.25 µm; temperature at first kept at 50° C. for 1 min, then increased at a rate of 10° C./min to 280° C. and kept there isothermally for 6 min; carrier gas: helium with a flow rate of 2 ml/min.

Method 14:

HPLC/ESI measurements: RP-C18 column (150 mm×4.6 mm) with 1 cm precolumn; particle size 5 µm, pore size 300 Å; eluent: mixtures of acetonitrile and water with 1% formic acid, mixing ratio altered over 15 min in a linear manner from initially 77% water to 77% acetonitrile and then kept under isocratic conditions for 5 min; flow rate: 1 ml/min.

Microwave:

The microwave reactor used was a "single-mode" instrument of the Emrys™ Optimizer type.

When compounds according to the invention are purified by preparative HPLC by the above-described methods in which the eluents contain additives, for example trifluoroacetic acid, formic acid or ammonia, the compounds according to the invention may be obtained in salt form, for example as trifluoroacetate, formate or ammonium salt, if the compounds according to the invention contain a sufficiently basic or acidic functionality. Such a salt can be converted to the corresponding free base or acid by various methods known to the person skilled in the art.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na$^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Starting Compounds

General Method 1A: Amide Coupling with HATU/DIEA

To a solution of the appropriate carboxylic acid (1.0 eq.) in dimethylformamide (7-15 ml/mmol) under argon and at RT were added the amine (1.1-1.2 eq.), N,N-diisopropylethylamine (2.2 eq.) and a solution of HATU (1.2 eq.) in a little dimethylformamide. The reaction mixture was stirred at RT. After addition of water/ethyl acetate and phase separation, the organic phase was washed with water and with saturated aqueous sodium chloride solution, dried (sodium sulphate or magnesium sulphate), filtered and concentrated under reduced pressure. The crude product was then purified either by means of normal phase chromatography (cyclohexane/ ethyl acetate mixtures or dichloromethane/methanol mixtures) or preparative RP-HPLC (water/acetonitrile gradient or water/methanol gradient).

General Method 2A: Amide Coupling Using T3P/DIEA

Under argon and at 0° C. or RT, N,N-diisopropylethylamine (3 eq.) and propylphosphonic anhydride (T3P, 50% in dimethylformamide or in ethyl acetate, 3 eq.) were added dropwise to a solution of the carboxylic acid and the appropriate amine (1.1-1.5 eq.) in dimethylformamide (0.15-0.05 mmol). The reaction mixture was stirred at RT and then concentrated under reduced pressure. After addition of water/ethyl acetate and phase separation, the aqueous phase was extracted twice with ethyl acetate. The combined organic phases were dried (sodium sulphate or magnesium sulphate), filtered and concentrated under reduced pressure. The crude product was then purified either by means of flash chromatography (cyclohexane/ethyl acetate mixtures or dichloromethane/methanol mixtures) or preparative HPLC (water/acetonitrile gradient or water/methanol gradient).

General Method 3A: Amide coupling using T3P/pyridine

A solution of the appropriate carboxylic acid (1 eq.) and the appropriate amine (1.1-1.5 eq.) in pyridine (about 0.1- 0.2 M) was heated to 60 to 90° C., and T3P (50% in dimethylformamide or ethyl acetate, 1.5-4 eq.) was added dropwise. Alternatively, T3P (50% in dimethylformamide or ethyl acetate, 1.5-4 eq.) was added dropwise at RT and the mixture was then stirred at RT or heated to 50 to 90° C. After 1 to 20 h, the reaction mixture was cooled to RT, and water and ethyl acetate were added. The aqueous phase was extracted with ethyl acetate. The combined organic phases were washed with aqueous buffer solution (pH=5), with saturated aqueous sodium hydrogencarbonate solution and with saturated aqueous sodium chloride solution, dried over sodium sulphate and concentrated under reduced pressure. The crude product was then optionally purified either by normal phase chromatography (cyclohexane/ethyl acetate mixtures or dichloromethane/methanol mixtures) or preparative RP-HPLC (water/acetonitrile gradient or water/methanol gradient).

Example 1.1A

2-Fluoro-4-nitrobenzamide

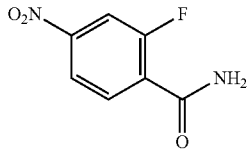 [SMILES: NC(=O)c1ccc([N+](=O)[O-])cc1F]

To a solution of 5.00 g (27.0 mmol) of 2-fluoro-4-nitrobenzoic acid and 2.29 g (29.7 mmol, 1.1 eq.) of ammonium acetate in 50 ml of dimethylformamide were added, under argon at 0° C., 14.1 ml (81.0 mmol, 3 eq.) of N,N-diisopropylethylamine and 47.3 ml (81.0 mmol, 3 eq.) of a T3P solution (50% in dimethylformamide) and then the mixture was stirred at RT for 3.5 h and at 60° C. for 3 h. After further addition of 7.1 ml (40.5 mmol, 1.5 eq.) of N,N-diisopropylethylamine and 23.7 ml (40.5 mmol, 1.5 eq.) of a T3P solution (50% in dimethylformamide), the reaction mixture was stirred at RT overnight and concentrated under reduced pressure. The residue was admixed with water and ethyl acetate, and the aqueous phase was extracted twice with ethyl acetate. The combined organic phases were washed with saturated aqueous sodium chloride solution, dried (sodium sulphate), filtered and concentrated under reduced pressure. The residue was purified by means of flash chromatography (silica gel 50, cyclohexane/ethyl acetate mixture). Yield: 1.06 g (21% of theory)

LC/MS [Method 3]: $R_t$=1.21 min; MS (ESIpos): m/z=185 (M+H)$^+$.

Example 1.1B

4-Amino-2-fluorobenzamide

A solution of 1.11 g (5.88 mmol) of 2-fluoro-4-nitrobenzamide in 60 ml of ethanol was hydrogenated in the presence of 111 mg of palladium (10% on activated carbon) at RT and standard pressure for 4 h. The reaction mixture was then filtered through Celite and the residue was washed with ethanol. The combined filtrates were concentrated under reduced pressure. The residue was used without further purification. Yield: 860 mg (95% of theory)

LC/MS [Method 5]: $R_t$=0.85 min; MS (ESIpos): m/z=155 (M+H)$^+$.

Example 1.2A

Imidazo[1,2-a]pyridin-6-amine

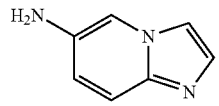

A solution of 600 mg (3.68 mmol) of 6-nitroimidazo[1,2-a]pyridine in 30 ml of ethanol was hydrogenated in the presence of 60 mg of palladium (10% on activated carbon) at RT and standard pressure overnight. The reaction mixture was then filtered through Celite and the residue was washed with ethanol. The combined filtrates were concentrated under reduced pressure and dried. The crude product was used without further purification in the next stage. Yield: 512 mg (quant.).

LC/MS [Method 5]: $R_t$=0.89 min; MS (ESIpos): m/z=134 (M+H)$^+$, $^1$H-NMR (400 MHz, DMSO-d$_6$): δ [ppm]=7.72-7.62 (m, 2H), 7.33 (d, 1H), 7.30 (d, 1H), 6.80 (dd, 1H), 4.83 (s, 2H).

Example 1.3A

1-Benzyl 2-tert-butyl 1-methylhydrazine-1,2-dicarboxylate

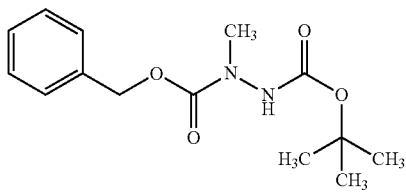 [SMILES: CN(NC(=O)OC(C)(C)C)C(=O)OCc1ccccc1]

At RT, 20.6 g (94.6 mmol, 1.2 eq.) of di-tert-butyl dicarbonate in 42 ml of dichloromethane were added to a solution of 14.2 g (78.8 mmol) of benzyl 1-methylhydrazinecarboxylate in 100 ml of propan-2-ol, and the mixture was stirred at RT for 24 h. The reaction mixture was diluted with dichloromethane and water. After phase separation, the organic phase was dried (sodium sulphate), filtered and concentrated under reduced pressure. The crude product was purified by means of flash chromatography (silica gel 50, cyclohexane/ethyl acetate mixtures). Yield: 24.8 g (80% purity, 90% of theory).

LC/MS [Method 1]: $R_t$=1.00 min; MS (ESIneg): m/z=279 (M−H)$^−$.

Example 1.3B tert-Butyl 2-methylhydrazinecarboxylate

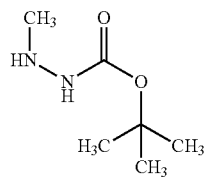

A solution of 24.8 g (80% purity, 70.8 mmol) of 1-benzyl 2-tert-butyl 1-methylhydrazine-1,2-dicarboxylate in 500 ml of ethanol was hydrogenated in the presence of 1.24 g of palladium (10% on activated carbon) at RT and standard pressure. The reaction mixture was then filtered through Celite, and the filtrate was concentrated under reduced pressure and dried. Yield: 12.3 g (48% purity, 57% of theory).

Example 1.3C tert-Butyl 2-(2-fluoro-4-nitrobenzoyl)-2-methylhydrazinecarboxylate

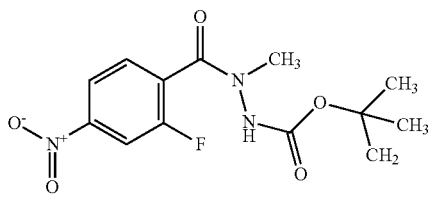 [SMILES: CN(NC(=O)OC(C)(C)C)C(=O)c1ccc([N+](=O)[O-])cc1F]

To a solution of 9.1 g (49.3 mmol, 1.2 eq.) of 2-fluoro-4-nitrobenzoic acid in 200 ml of dimethylformamide were added, under argon and at RT, 17.1 g (53.4 mmol, 1.3 eq.) of (benzotriazol-1-yloxy)bisdimethylaminomethylium fluoroborate and 21.4 ml (123.1 mol, 3.0 eq.) of N,N-diisopropylethylamine, and the mixture was stirred at RT for 20 min. A solution of 12.5 g (48% purity, 41 mmol) of tert-butyl 2-methylhydrazinecarboxylate in 50 ml of dimethylformamide was added, and the reaction mixture was stirred at RT for 6 h. Dimethylformamide was removed under reduced pressure. After addition of water/ethyl acetate and phase separation, the organic phase was washed with 10% aqueous citric acid and with saturated aqueous sodium chloride solution, dried (sodium sulphate), filtered and concentrated under reduced pressure. The crude product was purified by means of flash chromatography (silica gel 60, cyclohexane/ethyl acetate mixtures). Yield: 8.35 g (65% of theory)

LC/MS [Method 1]: $R_t$=0.91 min; MS (ESIneg): m/z=312 (M−H)−, $^1$H-NMR (400 MHz, DMSO-$d_6$): δ [ppm]=9.78 (s, 1H), 8.20 (d, 1H), 8.11 (d, 1H), 7.59 (t, 1H), 3.13 (s, 3H), 1.24 (s, 9H).

Example 1.3D

2-Fluoro-N-methyl-4-nitrobenzohydrazide

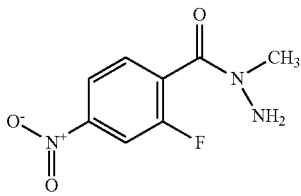

A solution of 3.6 g (11.5 mmol) of tert-butyl 2-(2-fluoro-4-nitrobenzoyl)-2-methylhydrazinecarboxylate in 57 ml of hydrogen chloride in dioxane (4 M) was stirred at RT for 3 h. The reaction mixture was concentrated under reduced pressure and the residue was taken up in ethyl acetate and washed with saturated aqueous sodium hydrogencarbonate solution. The organic phase was dried (sodium sulphate), filtered and concentrated under reduced pressure. Yield: 2.0 g (81% of theory)

LC/MS [Method 1]: $R_t$=0.50 min; MS (ESIpos): m/z=214 (M+H)+, $^1$H-NMR (400 MHz, DMSO-$d_6$): δ [ppm]=8.09 (m, 2H), 7.61 (dd, 1H), 3.2 (s, 3H).

Example 1.3E

2-Methyl-6-nitro-1,2-dihydro-3H-indazol-3-one

To a solution of 2.4 g (10.9 mmol) of 2-fluoro-N-methyl-4-nitrobenzohydrazide in 25 ml of DMF at RT were added 6.6 ml (37.9 mmol, 3.5 eq.) of N,N-diisopropylethylamine, and the mixture was stirred at 80° C. overnight. The reaction mixture was concentrated under reduced pressure and the residue was taken up in ethyl acetate. The precipitated solid was filtered off and dried under reduced pressure. Yield: 595 mg (28% of theory)

LC/MS [Method 1]: $R_t$=0.49 min; MS (ESIpos): m/z=194 (M+H)+, $^1$H-NMR (400 MHz, DMSO-$d_6$): δ [ppm]=8.14 (s, 1H), 7.85 (d, 1H), 7.78 (dd, 1H), 3.48 (s. 3H).

Example 1.3F tert-Butyl 2-methyl-6-nitro-3-oxo-2,3-dihydro-1H-indazole-1-carboxylate

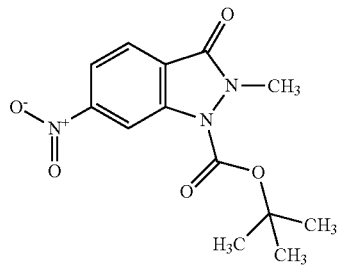 [SMILES: Cn1c(=O)c2ccc([N+](=O)[O-])cc2n1C(=O)OC(C)(C)C]

At RT, a solution of 0.8 g (3.7 mmol, 1.2 eq.) of di-tert-butyl dicarbonate in 6 ml of dichloromethane was added to a solution of 595 mg (3.0 mmol) of 2-methyl-6-nitro-1,2-dihydro-3H-indazol-3-one in 25 ml of propan-2-ol, and the mixture was stirred at RT for 12 h. To improve the solubility of the reaction mixture, 6 ml of dimethylformamide were added. A further 4 eq. of di-tert-butyl dicarbonate were added, and the reaction mixture was stirred at RT for 24 h and then diluted with dichloromethane and water. After phase separation, the organic phase was dried (sodium sulphate), filtered and concentrated under reduced pressure. The crude product was purified by means of flash chromatography (silica gel 60, cyclohexane/ethyl acetate mixtures). Yield: 720 mg (80% of theory)

LC/MS [Method 1]: $R_t$=1.04 min; MS (ESIpos): m/z=194 (M+H−Boc)$^+$, $^1$H-NMR (400 MHz, DMSO-d$_6$): δ [ppm]=8.62 (d, 1H), 8.17 (dd, 1H), 8.05 (d, 1H), 3.58 (s, 3H), 1.63 (s, 9H).

Example 1.3G tert-Butyl 6-amino-2-methyl-3-oxo-2,3-dihydro-1H-indazole-1-carboxylate

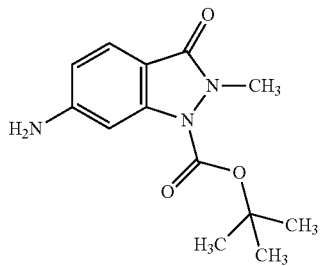 [SMILES: Cn1c(=O)c2ccc(N)cc2n1C(=O)OC(C)(C)C]

A solution of 715 mg (2.4 mmol) of tert-butyl 2-methyl-6-nitro-3-oxo-2,3-dihydro-H-indazole-1-carboxylate in 30 ml of ethanol was hydrogenated in the presence of 52 mg of palladium (10% on activated carbon) at RT and standard pressure. The reaction mixture was then filtered through Celite, and the filtrate was concentrated under reduced pressure and dried. Yield: 668 mg (quant.).

LC/MS [Method 1]: $R_t$=0.79 min; MS (ESIpos): m/z=264 (M+H)$^+$, $^1$H-NMR (400 MHz, DMSO-d$_6$): δ [ppm]=7.36 (d, 1H), 6.94 (d, 1H), 6.53 (dd, 1H), 6.21 (s, 2H), 1.58 (s, 9H).

Example 2.1A 1-(2-Bromo-4-chlorophenyl)methanamine

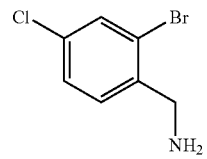

To a solution of 5.00 g (23.1 mmol) of 2-bromo-4-chlorobenzonitrile in 200 ml of THF were added dropwise, while cooling with an ice bath, 23.1 ml (46.2 mmol) of lithium aluminium hydride (2M in THF), and the mixture was stirred at 0 to 4° C. for a further 2 h. Subsequently, 2 ml of water, 2 ml of aqueous 20% sodium hydroxide solution and 6 ml of water were successively and cautiously added dropwise. The mixture was warmed to room temperature and stirred for a further 1 h. The precipitate was filtered off through Celite and the filtrate was concentrated under reduced pressure. Yield: 3.52 g (53% purity, 37% of theory).

LC/MS [Method 1]: $R_t$=0.42 min; MS (ESIpos): m/z=222 (M+H)$^+$.

Example 2.1B tert-Butyl (2-bromo-4-chlorobenzyl)carbamate

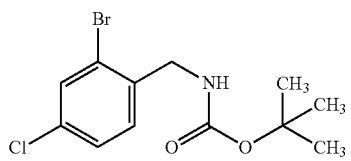 [SMILES: CC(C)(C)OC(=O)NCc1ccc(Cl)cc1Br]

To a solution of 3.52 g (53% purity, 8.46 mmol) of 1-(2-bromo-4-chlorophenyl)methanamine in 17 ml THF were added 1.98 g (9.05 mmol) of di-tert-butyl dicarbonate dissolved in 17 ml of tetrahydrofuran, and the resulting reaction solution was heated under reflux overnight. A further 3.69 g (16.9 mmol) of di-tert-butyl dicarbonate were added, and the mixture was heated under reflux for 48 h. The reaction was terminated by addition of saturated aqueous sodium chloride solution, and the mixture was then extracted three times with methyl tert-butyl ether. The combined organic phases were dried over magnesiumsulphate and filtered, and the solvent was removed under reduced pressure. The residue was purified by means of flash chromatography (silica gel 50, cyclohexane/ethyl acetate mixture). Yield: 1.63 g (60% of theory)

$^1$H-NMR (400 MHz, DMSO-d$_6$): δ [ppm]=7.73 (d, 1H), 7.51-7.45 (m, 2H), 7.28 (d, 1H), 4.13 (d, 2H), 1.40 (s, 9H).

Example 2.1C (2-{[(tert-Butoxycarbonyl)amino]methyl}-5-chlorophenyl)boric acid

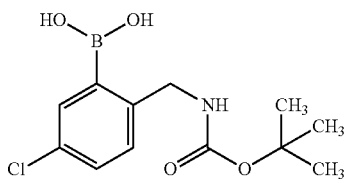 [SMILES: CC(C)(C)OC(=O)NCc1ccc(Cl)cc1B(O)O]

1.63 g (5.08 mmol) of tert-butyl (2-bromo-4-chlorobenzyl)carbamate were codistilled three times with 30 ml each time of toluene and then dried under high vacuum for 1 h. Subsequently added dropwise to a solution of this tert-butyl (2-bromo-4-chlorobenzyl)carbamate in 50 ml of tetrahydrofuran under argon at −78° C. were 3.18 ml (5.08 mmol, 1.0 eq.) of a methyllithium solution (1.6 M in diethyl ether), the mixture was stirred for 30 min, 2.03 ml (5.08 mmol, 1.0 eq.) of an n-butyllithium solution (2.5 M in n-hexane) were added, the mixture was stirred for 30 min, and finally 570 µl (5.08 mmol, 1.0 eq.) of trimethyl borate were added. After the addition had ended, the reaction mixture was allowed to come to RT and stirred at RT for a further 1 h, and then, while cooling with an ice bath, 50 ml of a saturated aqueous ammonium chloride solution were added. The mixture was extracted three times with ethyl acetate. The combined organic phases were washed with saturated aqueous sodium chloride solution, dried over magnesium sulphate and filtered, and the solvent was removed under reduced pressure. Yield: 1.27 g (50% purity, 44% of theory).

LC/MS [Method 1]: $R_t$=0.90 min; MS (ESIneg): m/z=284 (M−H)⁻.

Example 2.2A 1-(2-Bromo-4-chlorophenyl)cyclopropanamine

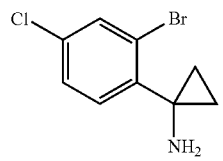 [SMILES: NC1(c2ccc(Cl)cc2Br)CC1]

4.00 g (18.5 mmol) of 2-bromo-4-chlorobenzonitrile were co-evaporated three times with 10 ml of toluene and the residue was dried under high vacuum overnight. The residue was taken up in 90 ml of dimethyl ether, 5.59 ml (20.3 mmol) of titanium tetra-iso-propoxide were added and the mixture was cooled down to −65° C. Subsequently, 20.3 ml (40.7 mmol) of ethylmagnesium chloride solution (2M in diethyl ether) were added and the mixture was stirred at −65° C. for a further 10 min and at room temperature for a further 1 h. Finally, 4.68 ml (36.9 mmol) of boron trifluoride-diethyl ether complex were added dropwise and the reaction mixture was stirred at room temperature for a further 1 h. The reaction mixture was poured onto 250 ml of 10% aqueous sodium hydroxide solution and 100 ml of diethyl ether, and stirred for a further 1 h. The mixture was filtered through Celite, the phases were separated and the aqueous phase was extracted twice with 100 ml of diethyl ether. The combined organic phases were dried over magnesium sulphate and filtered, and the solvent was removed under reduced pressure. Yield: 2.78 g (64% purity, 39% of theory).

LC/MS [Method 3]: $R_t$=1.44 min; MS (ESIpos): m/z=248 (M+H)⁺.

Example 2.2B tert-Butyl 1-(2-bromo-4-chlorophenyl)cyclopropyl]carbamate

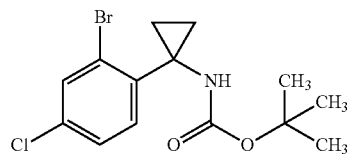

To a solution of 2.78 g (64% purity, 7.22 mmol) of 1-(2-bromo-4-chlorophenyl)cyclopropanamine in 72 ml of dichloromethane were added, at room temperature, 2.64 ml (15.2 mmol) of N,N-diisopropylethylamine and 2.68 g (12.3 mmol) of di-tert-butyl dicarbonate, and the mixture was stirred overnight. The reaction solution was diluted with 50 ml of water and the phases were separated. The aqueous phase was extracted once with 50 ml of dichloromethane and the combined organic phases were washed with 50 ml of saturated aqueous sodium chloride solution, dried over magnesium sulphate and filtered, and the solvent was removed under reduced pressure. The residue was purified by means of flash chromatography (silica gel 50, cyclohexane/ethyl acetate mixture). Yield: 1.27 g (51% of theory)

¹H-NMR (400 MHz, DMSO-$d_6$): δ [ppm]=7.70-7.37 (m, 3H), 1.31 (s, 9H), 1.14-0.96 (m, 4H).

Example 2.2C (2-{1-[(tert-Butoxycarbonyl)amino]cyclopropyl}-5-chlorophenyl)boric acid

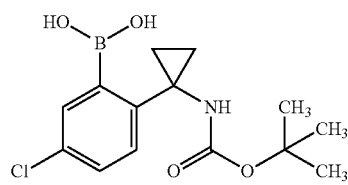 [SMILES: CC(C)(C)OC(=O)NC1(c2ccc(Cl)cc2B(O)O)CC1]

1.27 g (3.66 mmol) of tert-butyl [1-(2-bromo-4-chlorophenyl)cyclopropyl]carbamate were codistilled three times with 30 ml each time of toluene and then dried under high vacuum for 1 h. Subsequently added dropwise to a solution of this tert-butyl [1-(2-bromo-4-chlorophenyl)cyclopropyl]carbamate in 40 ml of tetrahydrofuran under argon at −78° C. were 2.29 ml (3.66 mmol, 1.0 eq.) of a methyllithium solution (1.6 M in diethyl ether), the mixture was stirred for 30 min, 1.47 ml (3.66 mmol, 1.0 eq.) of an n-butyllithium solution (2.5 M in n-hexane) were added, the mixture was stirred for 30 min, and finally 411 µl (3.66 mmol, 1.0 eq.) of trimethyl borate were added. After the addition had ended, the reaction mixture was allowed to come to RT and stirred at RT for a further 1 h, and then, while cooling with an ice bath, 50 ml of a saturated aqueous ammonium chloride solution were added. The mixture was extracted three times with 50 ml of ethyl acetate. The combined organic phases were washed with saturated aqueous sodium chloride solution, dried over magnesium sulphate and filtered, and the solvent was removed under reduced pressure. Yield: 0.99 g (68% purity, 59% of theory).

LC/MS [Method 1]: $R_t$=0.98 min; MS (ESIneg): m/z=310 (M−H)⁻.

Example 2.3A

2-Bromo-4-chloro-1-[2-nitroethenyl]benzene

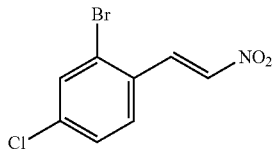 [SMILES: O=[N+]([O-])/C=C/c1ccc(Cl)cc1Br]

6.83 g (31.1 mmol) of 2-bromo-4-chlorobenzaldehyde and 5.52 g (71.6 mmol) of ammonium acetate were partly dissolved in 78 ml of acetic acid. Subsequently, 4.80 ml (80.7 mmol) of nitromethane were added and the reaction mixture was heated under reflux for 90 min. The mixture was cooled down to room temperature, 80 ml of water were added and the mixture was extracted with dichloromethane. The combined organic phases were washed with water and saturated aqueous sodium chloride solution, dried over sodium sulphate and filtered, and the solvent was removed under reduced pressure. Yield: 6.86 g (82% of theory)

¹H-NMR (400 MHz, DMSO-d₆): δ [ppm]=8.29 (d, 1H), 8.17 (d, 1H), 8.06 (d, 1H), 7.99 (d, 1H), 7.62 (dd, 1H).

Example 2.3B 2-(2-Bromo-4-chlorophenyl)ethanamine

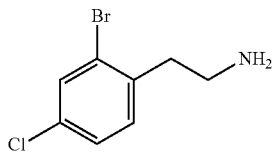 [SMILES: NCCc1ccc(Cl)cc1Br]

To a solution of 38.1 ml (76.2 mmol) of lithium borohydride (2M in THF) in 200 ml of THF were rapidly added dropwise at room temperature 19.3 ml (152 mmol) of chlorotrimethylsilane, and the mixture was then stirred for a further 20 min. The resulting reaction mixture was degassed, a solution of 5.00 g (19.0 mmol) of 2-bromo-4-chloro-1-[2-nitroethenyl]benzene in THF was added dropwise, and the mixture was heated under reflux for 2 h. The mixture was cooled down to room temperature and the reaction was ended by adding 50 ml of methanol. The solvent was removed under reduced pressure, and the residue was admixed with 50 ml of 20% aqueous potassium hydroxide solution and extracted with ethyl acetate. The combined organic phases were washed with saturated aqueous sodium chloride solution, dried over magnesium sulphate and filtered, and the solvent was removed under reduced pressure. Yield: 4.06 g (72% purity, 65% of theory).

LC/MS [Method 1]: $R_t$=0.53 min; MS (ESIpos): m/z=236 (M+H)⁺.

Example 2.3C tert-Butyl 2-(2-bromo-4-chlorophenyl)ethyl]carbamate

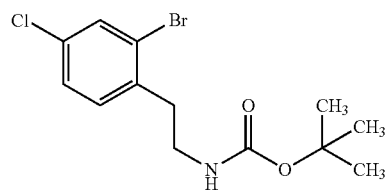 [SMILES: CC(C)(C)OC(=O)NCCc1ccc(Cl)cc1Br]

To a solution of 4.05 g (72% purity, 12.4 mmol) of 2-(2-bromo-4-chlorophenyl)ethanamine in 100 ml THF were added, while cooling with an ice bath, 2.85 g (13.1 mmol) of di-tert-butyl dicarbonate and 1.52 mg (1.24 mmol) of 4-dimethylaminopyridine. The mixture was warmed up spontaneously to room temperature and stirred for a further 1 h. Subsequently, the solvent was removed under reduced pressure, and the residue was taken up in water and extracted with ethyl acetate. The combined organic phases were washed with saturated aqueous sodium chloride solution, dried over magnesium sulphate and filtered, and the solvent was removed under reduced pressure. The residue was purified by flash chromatography (silica gel 50, cyclohexane/ethyl acetate gradient). Yield: 2.53 g (61% of theory)

LC/MS [Method 1]: $R_t$=1.23 min; MS (ESIpos): m/z=334 (M+H)⁺,

¹H-NMR (400 MHz, DMSO-d₆): δ [ppm]=7.70 (d, 1H), 7.41 (dd, 1H), 7.30 (d, 1H), 6.95-6.88 (m, 1H), 3.15 (dt, 2H), 2.80 (t, 2H), 1.35 (s, 9H).

Example 2.3D tert-Butyl {2-[4-chloro-2-(4,4,5,5-tetramethyl-1,3,2-dioxaborolan-2-yl)phenyl]ethyl}carbamate

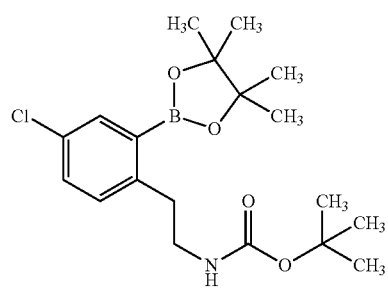 [SMILES: CC(C)(C)OC(=O)NCCc1ccc(Cl)cc1B1OC(C)(C)C(C)(C)O1]

1.04 g (3.11 mmol) of tert-butyl [2-(2-bromo-4-chlorophenyl)ethyl]carbamate were initially charged in 15.6 ml of 1,2-dimethoxyethane and the resulting solution was degassed. Subsequently, 868 mg (3.42 mmol) of 4,4,4',4',5,5,5',5'-octamethyl-2,2'-bi-1,3,2-dioxaborolane, 610 mg (6.22 mmol) of potassium acetate and 254 mg (311 µmol) of 1,1'-bis(diphenylphosphine)ferrocenedichloropalladium(II) were added and the reaction mixture was stirred at 80° C. for 8 h. The reaction mixture was cooled down to room temperature and filtered through Celite, the filtercake was washed with dichloromethane and the solvent was removed under reduced pressure. The residue was purified by means of flash chromatography (silica gel 50, cyclohexane/ethyl acetate mixture). Yield: 363 mg (82% purity, 25% of theory) and 580 mg (78% purity, 38% of theory)

LC/MS [Method 1]: $R_t$=1.41 min; MS (ESIneg): m/z=380 (M−H)⁻.

Example 2.4A (2-Bromo-4-chlorophenyl)methanol

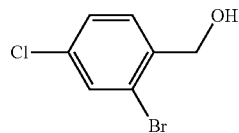

To a solution of 10.0 g (44.2 mmol) of 2-bromo-4-chlorobenzaldehyde in 90 ml of methanol in a baked-out flask were added in portions, under argon and while cooling with an ice bath, 836 mg (22.1 mmol) of sodium borohydride and the mixture was stirred while cooling with an ice bath for 1 h. After adding 200 ml of water, the methanol was removed under reduced pressure. The aqueous phase was extracted three times with in each case 80 ml of ethyl acetate. The combined organic phases were dried (magnesium sulphate), filtered and concentrated under reduced pressure. Yield: 7.75 g (79% of theory)

GC/MS [Method 9]: $R_t$=4.91 min; MS: m/z=220 (M)⁺,
¹H-NMR (400 MHz, DMSO-d₆): δ [ppm]=7.70 (d, 1H), 7.54 (d, 1H), 7.48 (dd, 1H), 5.51 (t, 1H), 4.48 (d, 2H).

Example 2.4B

2-Bromo-4-chlorobenzyl 4-methylbenzenesulphonate

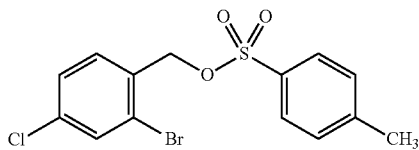 [SMILES: Cc1ccc(S(=O)(=O)OCc2ccc(Cl)cc2Br)cc1]

To a solution of 7.75 g (35.0 mmol) of (2-bromo-4-chlorophenyl)methanol in 100 ml of tetrahydrofuran were added, under argon and while cooling with an ice bath, 9.82 g (175.0 mmol, 5.0 eq.) of potassium hydroxide (previously dried and triturated) and then, dropwise, a solution of 8.17 g (42.0 mmol, 1.2 eq.) of para-toluenesulphonyl chloride in 65 ml of tetrahydrofuran. The reaction mixture was stirred while cooling with ice bath for a further 30 min, the cold bath was removed and then the mixture was allowed to come to RT and filtered through Celite. The filtrate was concentrated by rotary evaporator under reduced pressure (at water bath temperature <35° C.). The residue was co-evaporated three times with hexane (10 ml and 2×15 ml), dried under high vacuum and used without further purification (storage in a refrigerator). Yield: 14.20 g (75% purity, 81% of theory).

Example 2.4C (2-Bromo-4-chlorophenyl)acetonitrile

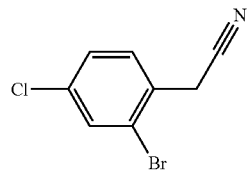 [SMILES: N#CCc1ccc(Cl)cc1Br]

To a solution of 14.20 g (75% purity, 28.3 mmol) of 2-bromo-4-chlorobenzyl 4-methylbenzenesulphonate in 142 ml of acetonitrile were added in portions, under argon at RT, 6.83 g (104.9 mmol, 3.7 eq.) of potassium cyanide and the mixture was stirred at RT for 60 h. The reaction mixture was filtered through Celite and the filtrate was concentrated under reduced pressure. The residue was co-evaporated repeatedly with hexane and then purified by means of flash chromatography (120 g of silica gel, cyclohexane/ethyl acetate mixture). Yield: 3.10 g (47% of theory)

GC/MS [Method 9]: $R_t$=5.29 min; MS: m/z=230 (M)⁺,
¹H-NMR (400 MHz, DMSO-d₆): δ [ppm]=7.87 (d, 1H), 7.61-7.53 (m, 2H), 4.09 (s, 2H).

Example 2.4D 1-(2-Bromo-4-chlorobenzyl)cyclopropanamine

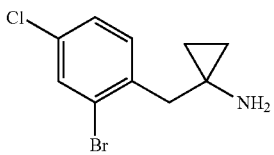 [SMILES: NC1(Cc2ccc(Cl)cc2Br)CC1]

3.49 g (15.1 mmol) of (2-bromo-4-chlorophenyl)acetonitrile were codistilled three times with toluene and then dried under high vacuum overnight. This residue was taken up in 100 ml of diethyl ether and, under argon at RT, 4.4 ml (15.9 mmol, 1.05 eq.) of titanium(IV) iso-propoxide were added to the solution, which was stirred at RT for 5 min. Subsequently added dropwise to the reaction mixture were 10.1 ml (30.3 mmol, 2.0 eq.) of an ethylmagnesium bromide solution (3 M in dimethyl ether), the mixture was stirred at RT for 30 min, 3.8 ml (30.3 mmol, 2.0 eq.) of boron trifluoride-diethyl ether complex were added rapidly and the mixture was stirred at RT for a further 60 min. The reaction mixture was poured onto a mixture of 250 ml of a 10% aqueous sodium hydroxide solution and 100 ml of diethyl ether, and filtered through Celite. After phase separation, the aqueous phase was extracted twice with 50 ml each time of diethyl ether. The combined organic phases were dried (magnesium sulphate), filtered, concentrated under reduced pressure and converted without further purification (storage in a refrigerator). Yield: 3.88 g (45% purity, 44% of theory).

LC/MS [Method 3]: $R_t$=1.56 min; MS (ESIpos): m/z=260 (M+H)⁺.

Example 2.4E tert-Butyl 1-(2-bromo-4-chlorobenzyl)cyclopropyl]carbamate

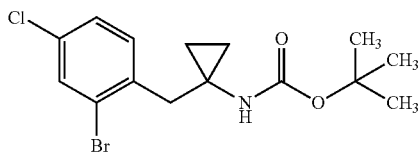 [SMILES: CC(C)(C)OC(=O)NC1(Cc2ccc(Cl)cc2Br)CC1]

To a solution of 3.88 g (45% purity, 6.7 mmol) of 1-(2-bromo-4-chlorobenzyl)cyclopropanamine in 94 ml of dichloromethane were added 2.5 ml (14.1 mmol, 2.1 eq.) of N,N-diisopropylethylamine and 2.5 g (11.4 mmol, 1.7 eq.) of di-tert-butyl dicarbonate, and the mixture was stirred at RT overnight. The reaction mixture was extracted three times with 100 ml each time of water. The aqueous phase was reextracted once with 100 ml of dichloromethane. The combined organic phases were washed with saturated aqueous sodium chloride solution, dried (magnesium sulphate), filtered and concentrated under reduced pressure. The residue was purified by means of flash chromatography (silica gel 50, cyclohexane/ethyl acetate mixture). Yield: 1.03 g (43% of theory)

LC/MS [Method 1]: $R_t$=1.32 min; MS (ESIpos): m/z=360 (M+H)$^+$, $^1$H-NMR (400 MHz, DMSO-d$_6$): δ [ppm]=7.70 (s, 1H), 7.45-7.38 (m, 2H), 7.09 (s, 1H), 2.94 (s, 2H), 1.34 (s, 9H), 0.80-0.60 (m, 4H).

Example 2.4F

[2-({1-[(tert-Butoxycarbonyl)amino]cyclopropyl}methyl)-5-chlorophenyl]boric acid

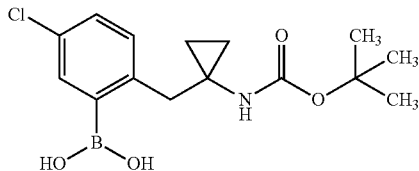 [SMILES: CC(C)(C)OC(=O)NC1(Cc2ccc(Cl)cc2B(O)O)CC1]

7.21 g (20.0 mmol) of tert-butyl [1-(2-bromo-4-chlorobenzyl)cyclopropyl]carbamate were codistilled three times with 60 ml each time of toluene and dried under high vacuum overnight. Subsequently added dropwise to a solution of this tert-butyl [1-(2-bromo-4-chlorobenzyl)cyclopropyl]carbamate in 200 ml of tetrahydrofuran under argon at −78° C. were 12.5 ml (20.0 mmol, 1.0 eq.) of a methyllithium solution (1.6 M in diethyl ether), the mixture was stirred for 30 min, 8.0 ml (20.0 mmol, 1.0 eq.) of an n-butyllithium solution (2.5 M in n-hexane) were added, the mixture was stirred for 30 min, and finally 2.2 ml (20 mmol, 1.0 eq.) of trimethyl borate were added. After the addition had ended, the reaction mixture was allowed to come to RT and stirred at RT for a further 1 h, and then, while cooling with an ice bath, 210 ml of a saturated aqueous ammonium chloride solution were added. The precipitated salts were filtered and washed with ethyl acetate. The combined filtrates were extracted three times with ethyl acetate. The combined organic phases were washed with saturated aqueous sodium chloride solution and concentrated under reduced pressure. The residue was dried under high vacuum and stored under argon. Yield: 6.5 g (81% purity, 81% of theory).

LC/MS [Method 1]: $R_t$=0.91 min; MS (ESIneg): m/z=324 (M−H)$^-$.

Example 2.5A

Methyl 2-bromo-N-(tert-butoxycarbonyl)-4-chlorophenylalaninate (Racemate)

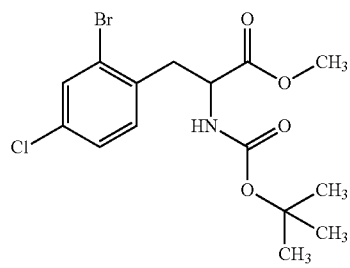 [SMILES: COC(=O)C(Cc1ccc(Cl)cc1Br)NC(=O)OC(C)(C)C]

To a solution of 47.8 ml (318 mmol, 2 eq.) of N,N,N',N'-tetramethylethane-1,2-diamine and 44.5 ml (318 mmol, 2 eq.) of N-isopropylpropan-2-amine (32.0 g, 318 mmol, 2 eq.) in 600 ml of tetrahydrofuran were added dropwise, under argon at −78° C., 127 ml (318 mmol, 2 eq.) of a solution of n-butyllithium in hexane (2.5M), and the mixture was stirred at −78° C. for 20 min. Then a solution of 30 g (159 mmol, 1 eq.) of methyl N-(ter-butoxycarbonyl)glycinate in 25 ml of tetrahydrofuran was added dropwise to the reaction mixture, in the course of which the internal temperature was kept below −70° C., and the mixture was stirred at this temperature for a further 60 min. Subsequently, a solution of 45 g (158 mmol, 1 eq.) of 2-bromo-1-(bromomethyl)-4-chlorobenzene in 40 ml of tetrahydrofuran was added dropwise, in the course of which the internal temperature was kept below −69° C. The reaction mixture was stirred at below −78° C. for a further 2 h, then allowed to come to −20° C. and quenched with 600 ml of saturated aqueous ammonium chloride solution. After addition of ethyl acetate and phase separation, the aqueous phase was extracted with ethyl acetate. The combined organic phases were washed twice with saturated aqueous sodium chloride solution, dried (sodium sulphate), filtered and very substantially concentrated under reduced pressure down to a pressure of 100 mbar. The desired product crystallized out of the residue when left to stand overnight, and was stirred with 80 ml of ethanol, filtered and dried under reduced pressure. Yield: 38.1 g (61% of theory)

GC/MS [Method 13]: $R_t$=23.23 min; MS: m/z=391 (M)$^+$, $^1$H-NMR (500 MHz, CDCl$_3$): δ [ppm]=7.54 (d, 1H), 7.21 (dd, 1H), 7.12 (d, 1H), 5.06 (d, 1H), 4.60 (q, 1H), 3.26 (dd, 1H), 3.24 (s, 3H), 3.05 (dd, 1H), 1.37 (s, 9H).

Example 2.5B tert-Butyl [1-(2-bromo-4-chlorophenyl)-3-hydroxypropan-2-yl]carbamate (Racemate)

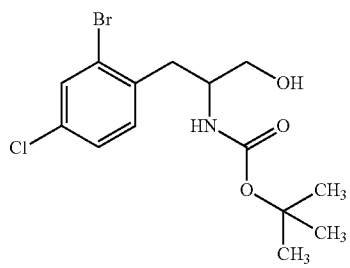 [SMILES: CC(C)(C)OC(=O)NC(CO)Cc1ccc(Cl)cc1Br]

To a suspension of 28.3 g (72.1 mmol, 1 eq.) of methyl 2-bromo-N-(tert-butoxycarbonyl)-4-chlorophenylalaninate (racemate) in 470 ml of tetrahydrofuran were added, at 0° C., 3.6 g (93.7 mmol, 1.3 eq.) of lithium aluminium hydride, in the course of which the internal temperature of the reaction mixture was kept below 10° C. After the addition had ended, the reaction mixture was allowed to come to RT. After 300 ml of tetrahydrofuran had been added for better stirrability, the reaction mixture was stirred at RT for 2.5 h. Subsequently, the reaction mixture was quenched by gradually adding 280 ml of saturated aqueous potassium sodium tartrate solution and stirred at RT for 20 min. After phase separation, the aqueous phase was extracted twice with ethyl acetate. The combined organic phases were washed with saturated aqueous sodium chloride solution, dried (sodium sulphate), filtered and concentrated under reduced pressure. The residue was taken up in 2-methoxy-2-methylpropane, and the mixture was washed twice with water and once with saturated aqueous sodium chloride solution and concentrated under reduced pressure. Yield: 19.8 g (75% of theory). The residue was used in the next stage without further purification.

Example 2.5C tert-Butyl 4-(2-bromo-4-chlorobenzyl)-1,2,3-oxathiazolidine-3-carboxylate 2-oxide (Diastereomer Mixture)

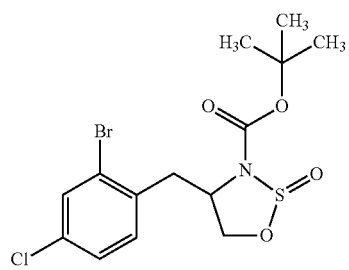 [SMILES: CC(C)(C)OC(=O)N1C(Cc2ccc(Cl)cc2Br)COS1=O]

To a solution of 8.0 g (22.0 mmol, 1 eq.) of tert-butyl [1-(2-bromo-4-chlorophenyl)-3-hydroxypropan-2-yl]carbamate (racemate) in 150 ml of dichloromethane were added dropwise, under argon at −60° C., 2.08 ml (28.7 mmol, 1.3 eq.) of thionyl chloride. Subsequently, 8.9 ml of pyridine (110 mmol, 5 eq.) were added dropwise, an exothermic reaction set in after a few drops of pyridine had been added, the reaction temperature rose to −40° C. and the reaction mixture was cooled again to −60° C. After the addition had ended, the reaction mixture was allowed to come to RT overnight and quenched with water. After addition of ethyl acetate and phase separation, the aqueous phase was extracted twice with ethyl acetate. The combined organic phases were washed with a mixture (1:1) of saturated aqueous sodium chloride solution and 20% aqueous citric acid solution and twice with saturated aqueous sodium chloride solution, dried (sodium sulphate), filtered and concentrated under reduced pressure. Yield: 7.8 g (87% of theory). The residue was used in the next stage without further purification.

HPLC/MS [Method 14]: $R_t$=17.3/17.6 min; MS (ESIpos): m/z=434 (M+Na)$^+$.

Example 2.5D tert-Butyl 4-(2-bromo-4-chlorobenzyl)-1,2,3-oxathiazolidine-3-carboxylate 2,2-dioxide (Racemate)

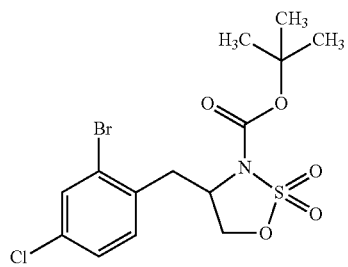 [SMILES: CC(C)(C)OC(=O)N1C(Cc2ccc(Cl)cc2Br)COS1(=O)=O]

To a solution of 20 g (48.9 mmol, 1 eq.) of tert-butyl 4-(2-bromo-4-chlorobenzyl)-1,2,3-oxathiazolidine-3-carboxylate 2-oxide (diastereomer mixture) in 500 ml of acetonitrile were added, at 0° C., 16.75 g (78.3 mmol, 1.6 eq.) of sodium periodate, 114 mg of ruthenium trichloride and 125 ml of water. The reaction mixture was stirred for 2.5 h, forming a precipitate which was then filtered. The filtrate was admixed with 150 ml of water and, after addition of 2-methoxy-2-methylpropane and phase separation, the aqueous phase was extracted three times with 2-methoxy-2-methylpropane. The combined organic phases were washed with saturated aqueous sodium sulphite solution and with saturated aqueous sodium chloride solution, dried (sodium sulphate), filtered and concentrated under reduced pressure, giving 7.5 g of crude material. The solids from the filtration were extracted three times with hot 2-methoxy-2-methylpropane. The combined organic phases were washed with saturated aqueous sodium sulphite solution and with saturated aqueous sodium chloride solution, dried (sodium sulphate), filtered and concentrated under reduced pressure, giving 9.6 g of crude material. The combined crude products were stirred with 30 ml of ethyl acetate, filtered and dried under reduced pressure. Yield: 9.4 g (45% of theory)

HPLC/MS [Method 14]: $R_t$=16.6 min; MS (ESIpos): m/z=875 (2M+Na)$^+$.

Example 2.5E tert-Butyl [1-(2-bromo-4-chlorophenyl)-3-fluoropropan-2-yl]carbamate (Racemate)

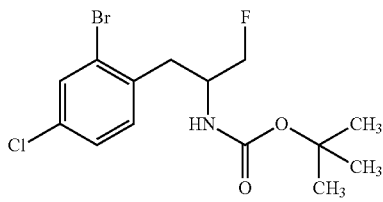

To a suspension of 9.3 g (21.8 mmol, 1 eq.) of tert-butyl 4-(2-bromo-4-chlorobenzyl)-1,2,3-oxathiazolidine-3-carboxylate 2,2-dioxide (racemate) in 250 ml of tetrahydrofuran were added 1.8 ml (10.9 mmol, 0.5 eq.) of triethylamine trihydrofluoride and 6.65 ml (47.9 mmol, 2.2 eq.) of triethylamine. The reaction mixture was stirred at 55° C. for 16 h, cooled down to RT and then quenched with 380 ml of water. After addition of ethyl acetate and phase separation, the aqueous phase was extracted three times with ethyl acetate. The combined organic phases were washed twice with saturated aqueous sodium chloride solution, dried (sodium sulphate), filtered and concentrated under reduced pressure. 7.8 g of crude product were obtained. For column chromatography purification, the crude product was combined with material from other batches and 8.2 g thus obtained were purified by means of flash chromatography (250 g of silica gel, dichloromethane/methanol mixtures from 95/5→85/15). Yield: 3.3 g.

Further flash chromatography (150 g of silica gel, dichloromethane/methanol mixtures from 95/5 to 85/15) of the mixed fraction gave another 1.3 g of the desired product.

HPLC/MS [Method 14]: $R_t$=16.0 min; MS (ESIpos): m/z=388 (M+Na)$^+$, $^1$H-NMR (500 MHz, CDCl$_3$): δ [ppm]=7.51-7.49 (m, 1H), 7.46-7.41 (m, 1H), 7.22-7.16 (m, 1H), 4.97-4.51 (m, 3H), 3.33-3.05 (m, 2H), 1.27-1.07 (br. s, 9H), $^{19}$F-NMR (470 MHz, CDCl$_3$): δ [ppm]=−216.6 ppm.

Example 3.1A

Ethyl 4-(2-{[(tert-butoxycarbonyl)amino]methyl}-5-chlorophenyl)-1-(1-ter-butoxy-1-oxobutan-2-yl)-6-oxo-1,6-dihydropyridine-3-carboxylate (Stereoisomer Mixture)

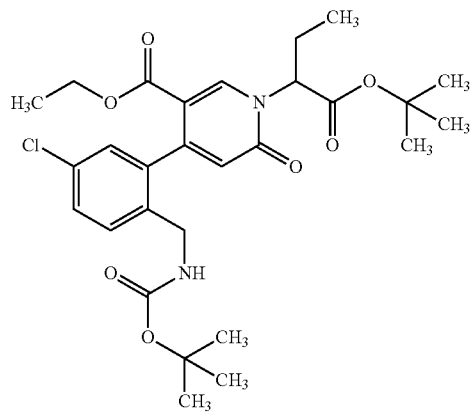 [SMILES: CCOC(=O)c1cn(C(CC)C(=O)OC(C)(C)C)c(=O)cc1-c1cc(Cl)ccc1CNC(=O)OC(C)(C)C]

796 mg (5.76 mmol) of potassium carbonate were dried in the reaction vessel and then 850 mg (1.86 mmol) of ethyl 1-(1-tert-butoxy-1-oxobutan-2-yl)-6-oxo-4-{[(trifluoromethyl)sulphonyl]oxy}-1,6-dihydropyridine-3-carboxylate (racemate), 1.27 g (2.23 mmol) of (2-{[(tert-butoxycarbonyl)amino]methyl}-5-chlorophenyl)boric acid (50% purity) and 18 ml of 1,4-dioxane were added. The reaction mixture was degassed, 215 mg (186 μmol) of tetrakis(triphenylphosphine)palladium(0) were added and the mixture was agitated at 110° C. for 1.5 h. The mixture was cooled down to room temperature and the solvent was removed under reduced pressure. The residue was purified by means of flash chromatography (silica gel 50, cyclohexane/ethyl acetate mixture). Yield: 685 mg (65% of theory)

LC/MS [Method 1]: $R_t$=1.34 min; MS (ESIpos): m/z=549 (M+H)$^+$.

Example 3.1B

2-{4-[2-(Aminomethyl)-5-chlorophenyl]-5-(ethoxycarbonyl)-2-oxopyridin-1(2H)-yl}butanoic acid (Stereoisomer Mixture)

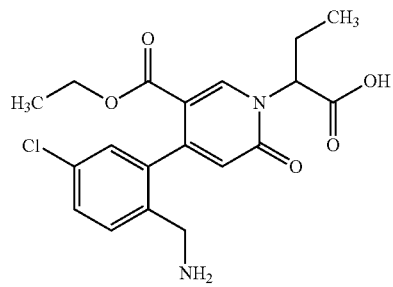 [SMILES: CCOC(=O)c1cn(C(CC)C(=O)O)c(=O)cc1-c1cc(Cl)ccc1CN]

680 mg (1.24 mmol) of ethyl 4-(2-{[(tert-butoxycarbonyl)amino]methyl-}5-chlorophenyl)-1-(1-tert-butoxy-1-oxobutan-2-yl)-6-oxo-1,6-dihydropyridine-3-carboxylate (stereoisomer mixture) were initially charged in 5 ml of dichloromethane, and 954 μl (12.4 mmol) of trifluoroacetic acid were added. The mixture was stirred at room temperature until conversion was complete. Subsequently, the solvent was removed under reduced pressure and the residue was repeatedly co-evaporated with dichloromethane and toluene. Yield: 751 mg (89% purity, quantitative)

LC/MS [Method 1]: $R_t$=0.65 min; MS (ESIpos): m/z=393 (M+H)$^+$.

Example 3.1C 2-(10-Chloro-2,5-dioxo-2,5,6,7-tetrahydro-3H-pyrido[3,4-d][2]benzazepin-3-yl)butanoic acid (Stereoisomer Mixture)

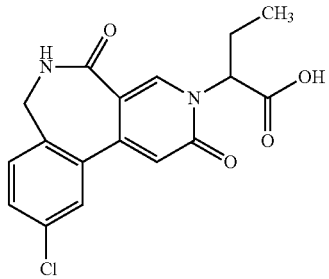 [SMILES: CCC(C(=O)O)n1cc2c(cc1=O)-c1cc(Cl)ccc1CNC2=O]

A solution of 486 mg (1.10 mmol) of 2-{4-[2-(aminomethyl)-5-chlorophenyl]-5-(ethoxycarbonyl)-2-oxopyridin-1

(2H)-yl}butanoic acid (stereoisomer mixture) in 11 ml of tetrahydrofuran was added under argon to activated 3 Å molecular sieve (dried at 200° C. in a drying cabinet overnight) and stirred at RT for 2 h. Subsequently, the reaction mixture was admixed under argon at RT with 8.22 ml (22.0 mmol, 20 eq.) of a sodium ethoxide solution (21% in ethanol, dried beforehand over activated 3 Å molecular sieve for 2 h) and stirred at room temperature for 45 min. After dilution with ethyl acetate, the reaction mixture was admixed with saturated aqueous ammonium chloride solution and brought to pH 3 with aqueous hydrochloric acid solution (1 N) and extracted again with ethyl acetate. The combined organic phases were washed three times with 50 ml of aqueous 0.5 M hydrochloric acid and 50 ml of saturated aqueous sodium chloride solution, dried over magnesium sulphate and filtered, and the solvent was removed under reduced pressure. Yield: 364 mg (95% of theory)

LC/MS [Method 1]: $R_t$=0.70 min; MS (ESIpos): m/z=347 (M+H)$^+$.

Example 3.1D tert-Butyl 4-{[2-(10-chloro-2,5-dioxo-2,5,6,7-tetrahydro-3H-pyrido[3,4-d][2]benzazepin-3-yl)butanoyl]amino}benzoate (Stereoisomer Mixture)

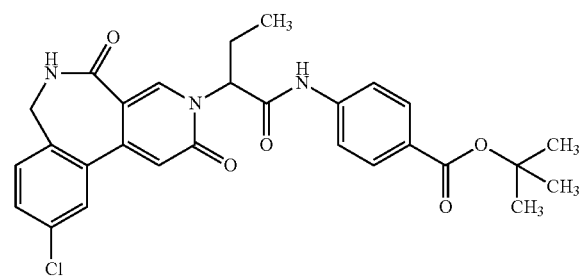 [SMILES: CCC(C(=O)Nc1ccc(C(=O)OC(C)(C)C)cc1)n1cc2c(cc1=O)-c1cc(Cl)ccc1CNC2=O]

75.0 mg (216 µmol) of 2-(10-chloro-2,5-dioxo-2,5,6,7-tetrahydro-3H-pyrido[3,4-d][2]benzazepin-3-yl)butanoic acid (stereoisomer mixture) and 62.7 mg (324 µmol, 1.5 eq.) of tert-butyl 4-aminobenzoate were initially charged in 5 ml of pyridine. Subsequently, 505 µl (865 µmol) of propylphosphonic anhydride (T3P, 50% in ethyl acetate, 4 eq.) were added dropwise and the reaction mixture was stirred at 60° C. overnight. The reaction was cooled to room temperature and 50 ml of water were added. The mixture was extracted three times with 30 ml of ethyl acetate. The combined organic phases were washed three times with pH 5 buffer, and the solvent was removed under reduced pressure. The residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 44.2 mg (39% of theory)

LC/MS [Method 1]: $R_t$=1.05 min; MS (ESIpos): m/z=522 (M+H)$^+$, $^1$H-NMR (400 MHz, DMSO-$d_6$): δ [ppm]=10.9 (s, 1H), 8.55 (br. s, 1H), 8.27 (s, 1H), 7.87 (d, 2H), 7.76-7.72 (m, 3H), 7.54 (dd, 1H), 7.43 (d, 1H), 6.65 (s, 1H), 5.67-5.60 (m, 1H), 4.29-3.89 (2×br. s, 2H), 2.26-2.15 (m, 1H), 2.11-1.97 (m, 1H), 1.54 (s, 9H), 0.92 (t, 3H).

Example 4.1A

Ethyl 4-(2-{1-[(tert-butoxycarbonyl)amino]cyclopropyl}-5-chlorophenyl)-1-(1-tert-butoxy-1-oxobutan-2-yl)-6-oxo-1,6-dihydropyridine-3-carboxylate (Stereoisomer Mixture)

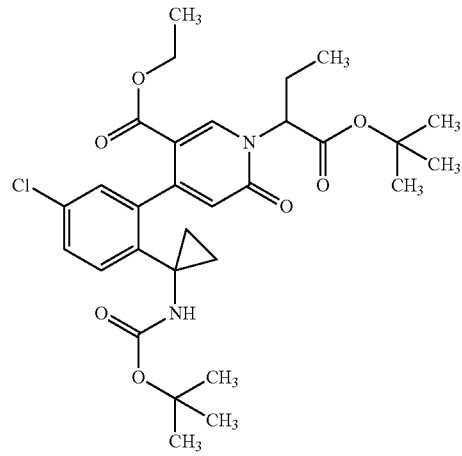 [SMILES: CCOC(=O)c1cn(C(CC)C(=O)OC(C)(C)C)c(=O)cc1-c1cc(Cl)ccc1C1(NC(=O)OC(C)(C)C)CC1]

860 mg (6.22 mmol) of potassium carbonate were dried in the reaction vessel and then 918 mg (2.01 mmol) of ethyl 1-(1-tert-butoxy-1-oxobutan-2-yl)-6-oxo-4-{[(trifluoromethyl)sulphonyl]oxy}-1,6-dihydropyridine-3-carboxylate (racemate), 920 mg (2.08 mmol) of (2-{1-[(tert-butoxycarbonyl)amino]cyclopropyl}-5-chlorophenyl)boric acid (68% purity) and 20 ml of 1,4-dioxane were added. The reaction mixture was degassed, 232 mg (201 µmol) of tetrakis(triphenylphosphine)palladium(0) were added and the mixture was agitated at 80° C. for 7 h. The mixture was cooled down to room temperature and filtered, and the solvent was removed under reduced pressure. The residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 149 mg (12% of theory)

LC/MS [Method 1]: $R_t$=1.39 min; MS (ESIpos): m/z=575 (M+H)$^+$.

Example 4.1B

2-{4-[2-(Aminocyclopropyl)-5-chlorophenyl]-5-(ethoxycarbonyl)-2-oxopyridin-1(2H)-yl}butanoic acid (Stereoisomer Mixture)

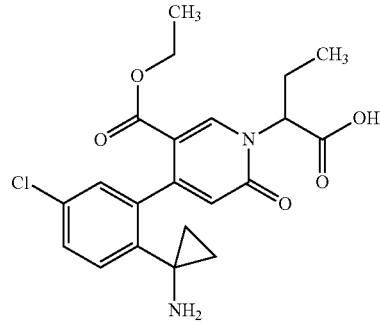 [SMILES: CCOC(=O)c1cn(C(CC)C(=O)O)c(=O)cc1-c1cc(Cl)ccc1C1(N)CC1]

165 mg (275 µmol) of ethyl 4-(2-{1-[(tert-butoxycarbonyl)amino]cyclopropyl}-5-chlorophenyl)-1-(1-tert-butoxy-1-oxobutan-2-yl)-6-oxo-1,6-dihydropyridine-3-carboxylate (stereoisomer mixture) were initially charged in 3 ml of dichloromethane, and 530 µl (6.89 mmol) of trifluoroacetic acid were added in portions while cooling with an ice bath. The mixture was stirred at room temperature until conversion was complete. Subsequently, the solvent was removed under reduced pressure and the residue was co-evaporated three times with 10 ml of toluene. The residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 60 mg (94% purity, 49% of theory)

LC/MS [Method 1]: $R_t$=0.66 min; MS (ESIpos): m/z=419 (M+H)$^+$.

Example 4.1C 2-(10'-Chloro-2',5'-dioxo-5',6'-dihydrospiro[cyclopropane-1,7'-pyrido[3,4-d][2]benzazepine]-3'(2'H)-yl)butanoic acid (Stereoisomer Mixture)

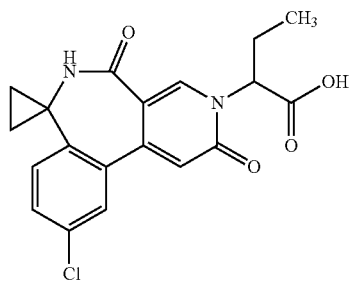 [SMILES: CCC(C(=O)O)n1cc2c(cc1=O)-c1cc(Cl)ccc1C1(CC1)NC2=O]

A solution of 60.0 mg (143 µmol) of 2-{4-[2-(1-aminocyclopropyl)-5-chlorophenyl]-5-(ethoxycarbonyl)-2-oxopyridin-1(2H)-yl}butanoic acid (stereoisomer mixture) in 3 ml of tetrahydrofuran was added under argon to activated 3 Å molecular sieve (dried at 200° C. in a drying cabinet overnight) and stirred at RT for 2 h. Subsequently, the reaction mixture was admixed under argon at RT with 670 µl (2.87 mmol, 20 eq.) of a sodium ethoxide solution (21% in ethanol, dried beforehand over activated 3 Å molecular sieve for 2 h) and stirred at room temperature for 45 min. After dilution with ethyl acetate, the reaction mixture was admixed with saturated aqueous ammonium chloride solution and brought to pH 3 with aqueous hydrochloric acid solution (1 N) and extracted again with ethyl acetate. The combined organic phases were washed with 50 ml of aqueous saturated sodium chloride solution, dried over magnesium sulphate and filtered, and the solvent was removed under reduced pressure. Yield: 51.8 mg (97% of theory)

LC/MS [Method 1]: $R_t$=0.69 min; MS (ESIpos): m/z=373 (M+H)$^+$.

Example 4.1D tert-Butyl 4-{[2-(10'-chloro-2',5'-dioxo-5',6'-dihydrospiro[cyclopropane-1,7'-pyrido[3,4-d][2]benzazepine]-3'(2'H)-yl)butanoyl]amino}benzoate (Stereoisomer Mixture)

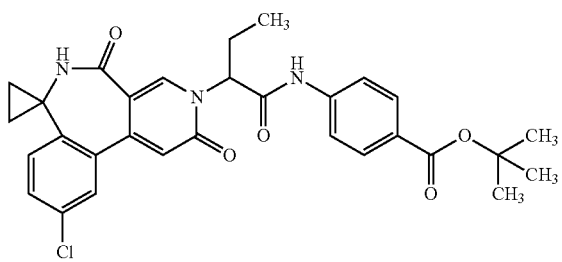 [SMILES: CCC(C(=O)Nc1ccc(C(=O)OC(C)(C)C)cc1)n1cc2c(cc1=O)-c1cc(Cl)ccc1C1(CC1)NC2=O]

52.0 mg (139 µmol) of 2-(10'-chloro-2',5'-dioxo-5',6'-dihydrospiro[cyclopropane-1,7'-pyrido[3,4-d][2]benzazepine]-3'(2'H)-yl)butanoic acid (stereoisomer mixture) and 40.4 mg (209 µmol, 1.5 eq.) of tert-butyl 4-aminobenzoate were initially charged in 3 ml of pyridine. Subsequently, 163 µl (558 µmol) of propylphosphonic anhydride (T3P, 50% in ethyl acetate, 4 eq.) were added dropwise and the reaction mixture was stirred at 60° C. overnight and at 80° C. for 2 h. The reaction mixture was purified directly by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 46.9 mg (76% of theory)

LC/MS [Method 1]: $R_t$=1.13 min; MS (ESIpos): m/z=548 (M+H)$^+$, $^1$H-NMR (400 MHz, DMSO-d$_6$): δ [ppm]=10.9 (2×s, 1H), 8.88/8.85 (2×s, 1H), 8.20 (s, 1H), 7.89-7.85 (m, 2H), 7.76-7.71 (m, 3H), 7.52 (dd, 1H), 7.38 (d, 1H), 6.66/6.64 (2×s, 1H), 5.68-5.61 (m, 1H), 2.28-1.99 (m, 2H), 1.54 (s, 9H), 1.52-1.45 (m, 1H), 1.21-1.12 (m, 1H), 0.98-0.81 (m, 4H), 0.63- 0.54 (m, 1H).

Example 5.1A

Ethyl 4-chloro-6-oxo-1,6-dihydropyridine-3-carboxylate

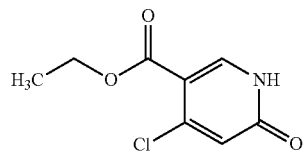

9.82 g (44.6 mmol) of ethyl 4,6-dichloropyridine-3-carboxylate were initially charged in 98 ml of acetic acid, and 4.03 g (49.1 mmol) of sodium acetate were added. The reaction mixture was heated under reflux overnight and then poured onto 100 ml of water. The precipitate was filtered off with suction, washed with water and dried under high vacuum. Yield: 6.35 g (91% purity, 64% of theory).

LC/MS [Method 1]: $R_t$=0.61 min; MS (ESIpos): m/z=202 (M+H)$^+$, $^1$H-NMR (400 MHz, DMSO-d$_6$): δ [ppm]=12.4 (br. s, 1H), 8.11 (s, 1H), 6.55 (s, 1H), 4.22 (q, 2H), 1.28 (t, 3H).

Example 5.1B

Ethyl 1-(2-tert-butoxy-2-oxoethyl)-4-chloro-6-oxo-1,6-dihydropyridine-3-carboxylate

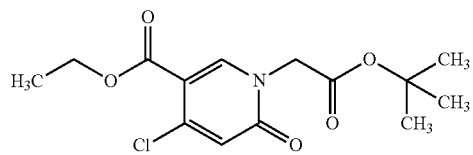 [SMILES: CCOC(=O)c1cn(CC(=O)OC(C)(C)C)c(=O)cc1Cl]

2.00 g (9.92 mmol) of ethyl 4-chloro-6-oxo-1,6-dihydropyridine-3-carboxylate, 2.32 g (11.9 mmol) of tert-butyl bromoacetate and 2.06 g (14.9 mmol) of potassium carbonate were stirred at 100° C. in 35 ml of dimethylformamide for 45 min. Subsequently, the solvent was removed under reduced pressure, and the residue was taken up in water and extracted with ethyl acetate. The combined organic phases were washed with aqueous saturated sodium chloride solution, dried with magnesium sulphate and filtered, and the solvent was removed under reduced pressure. Yield: 3.07 g (94% purity, 92% of theory).

LC/MS [Method 1]: R$_t$=0.96 min; MS (ESIpos): m/z=316 (M+H)$^+$, $^1$H-NMR (400 MHz, DMSO-d$_6$): δ [ppm]=8.62 (s, 1H), 6.60 (s, 1H), 4.71 (s, 2H), 4.26 (q, 2H), 1.42 (s, 9H), 1.30 (t, 3H).

Example 5.1C

[1-(2-tert-Butoxy-2-oxoethyl)-5-(ethoxycarbonyl)-2-oxo-1,2-dihydropyridin-4-yl]boric acid

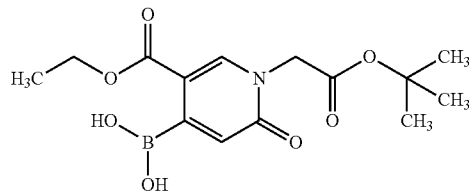 [SMILES: CCOC(=O)c1cn(CC(=O)OC(C)(C)C)c(=O)cc1B(O)O]

3.07 g (9.72 mmol) of ethyl 1-(2-tert-butoxy-2-oxoethyl)-4-chloro-6-oxo-1,6-dihydropyridine-3-carboxylate were initially charged in 35 ml of 1,4-dioxane and the solution was degassed. Subsequently, 1.91 g (19.4 mmol) of potassium acetate, 0.71 g (0.97 mmol) of 1,1'-bis(diphenylphosphine)ferrocenepalladium(II) chloride, 2.72 g (10.7 mmol) of 4,4,4',4',5,5,5',5'-octamethyl-2,2'-bi-1,3,2-dioxaborolane were added and the reaction mixture was stirred at 130° C. for 2.5 h. The mixture was cooled down to room temperature, diluted with ethyl acetate and filtered through silica gel, and the solvent was removed under reduced pressure. The residue was purified by means of flash chromatography (silica gel 50, cyclohexane/ethyl acetate mixture, then dichloromethane/methanol mixture). Yield: 431 mg (69% purity, 9% of theory)

LC/MS [Method 1]: R$_t$=0.64 min; MS (ESIpos): m/z=326 (M+H)$^+$.

Example 5.1D

Ethyl 4-(2-{2-[(tert-butoxycarbonyl)amino]ethyl}-5-chlorophenyl)-1-(2-tert-butoxy-2-oxoethyl)-6-oxo-1,6-dihydropyridine-3-carboxylate

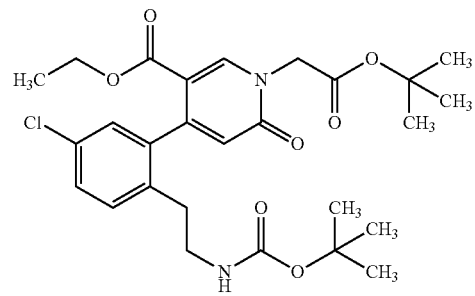 [SMILES: CCOC(=O)c1cn(CC(=O)OC(C)(C)C)c(=O)cc1-c1cc(Cl)ccc1CCNC(=O)OC(C)(C)C]

386 mg (1.15 mmol) of tert-butyl [2-(2-bromo-4-chlorophenyl)ethyl]carbamate were initially charged in 11 ml of THF and the resulting solution was degassed. Subsequently, 1.00 g (75% purity, 2.31 mmol) of [1-(2-tert-butoxy-2-oxoethyl)-5-(ethoxycarbonyl)-2-oxo-1,2-dihydropyridin-4-yl]boronic acid, 67 mg (58 µmol) of tetrakis(triphenylphosphine)palladium(0) and 350 mg (2.31 mmol) of caesium fluoride were added, and the reaction mixture was stirred at 110° C. overnight. The solvent was removed under reduced pressure, and the residue was taken up in acetonitrile, filtered through a fine filter and purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 303 mg (49% of theory)

LC/MS [Method 1]: R$_t$=1.27 min; MS (ESIpos): m/z=535 (M+H)$^+$, $^1$H-NMR (400 MHz, DMSO-d$_6$): δ [ppm]=8.61 (s, 1H), 7.37 (dd, 1H), 7.26 (d, 1H), 7.12 (d, 1H), 6.75-6.69 (m, 1H), 6.28 (s, 1H), 4.77 (s, 2H), 4.00-3.92 (m, 2H), 3.04-2.95 (m, 2H), 2.57-2.38 (m, 2H), 1.44 (s, 9H), 1.32 (s, 9H), 0.93 (t, 3H).

Example 5.1E

{4-[2-(2-Aminoethyl)-5-chlorophenyl]-5-(ethoxycarbonyl)-2-oxopyridin-1(2H)-yl}acetic acid

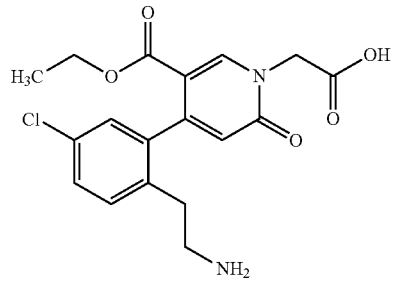 [SMILES: CCOC(=O)c1cn(CC(=O)O)c(=O)cc1-c1cc(Cl)ccc1CCN]

307 mg (574 µmol) of ethyl 4-(2-{[(tert-butoxycarbonyl)amino]ethyl}-5-chlorophenyl)-1-(2-tert-butoxy-2-oxoethyl)-6-oxo-1,6-dihydropyridine-3-carboxylate were initially charged in 5 ml of dichloromethane, and 633 μl (8.61 mmol) of trifluoroacetic acid were added. The mixture was stirred for a further 3 h. The solvent was removed under reduced pressure and the residue was codistilled three times with 2 ml of dichloromethane and finally lyophilized. The lyophilizate was purified by means of preparative HPLC [column: Chromatorex C18, 10 μm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 74 mg (30% of theory)

LC/MS [Method 1]: $R_t$=0.63 min; MS (ESIpos): m/z=379 (M+H)$^+$, $^1$H-NMR (400 MHz, DMSO-$d_6$): δ [ppm]=8.42 (s, 1H), 7.41 (dd, 1H), 7.33 (d, 1H), 7.14 (d, 1H), 6.18 (s, 1H), 4.42-4.30 (m, 2H), 3.96 (q, 2H), 2.93-2.82 (m, 2H), 2.76-2.59 (m, 2H), 0.97 (t, 3H).

Example 5.1F (11-Chloro-2,5-dioxo-5,6,7,8-tetrahydropyrido[3,4-e][3]benzazocin-3(2H)-yl)acetic acid

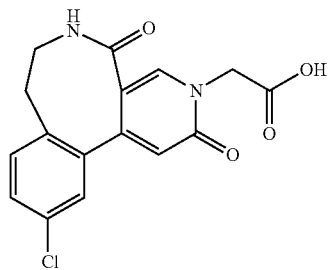 [SMILES: O=C(O)Cn1cc2c(cc1=O)-c1cc(Cl)ccc1CCNC2=O]

74.0 mg (195 μmol) of {4-[2-(2-aminoethyl)-5-chlorophenyl]-5-(ethoxycarbonyl)-2-oxopyridin-1(2H)-yl}acetic acid were initially charged in 3.9 ml of THF, and 15.6 mg (391 μmol) of sodium hydride (60% in mineral oil) were added. The mixture was stirred at room temperature for a further 30 min and then 7.8 mg (0.20 mmol) of sodium hydride (60% in mineral oil) were added. The mixture was stirred for a further 4 h and the reaction was ended by adding water. The phases were separated and the aqueous phase was extracted three times with 10 ml of ethyl acetate. The combined organic phases were dried over magnesium sulphate and filtered, and the solvent was removed under reduced pressure. The residue was purified by means of preparative HPLC [column: Chromatorex C18, 10 μm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 4.6 mg (95% purity, 7% of theory) and 6.4 mg (85% purity, 8% of theory)

LC/MS [Method 1]: $R_t$=0.56 min; MS (ESIpos): m/z=333 (M+H)$^+$, $^1$H-NMR (400 MHz, DMSO-$d_6$): δ [ppm]=7.86 (s, 1H), 7.72 (t, 1H), 7.45 (dd, 1H), 7.31 (d, 1H), 7.23 (d, 1H), 6.28 (s, 1H), 4.64 (s, 2H), 3.47-3.21 (m, 2H), 2.98-2.89 (m, 2H).

Alternatively, the title compound can also be prepared in analogy to the method described in Example 9.1G. The conversion of 36 mg (61 μmol) of {4-[2-(2-aminoethyl)-5-chlorophenyl]-5-(ethoxycarbonyl)-2-oxopyridin-1(2H)-yl}acetic acid (64% purity) gave 15.4 mg (44% purity, 33% of theory) of the title compound.

LC/MS [Method 3]: $R_t$=1.49 min; MS (ESIpos): m/z=333 (M+H)$^+$.

Example 5.1G tert-Butyl 4-{[(11-chloro-2,5-dioxo-5,6,7,8-tetrahydropyrido[3,4-e][3]benzazocin-3(2H)-yl)acetyl]amino}benzoate

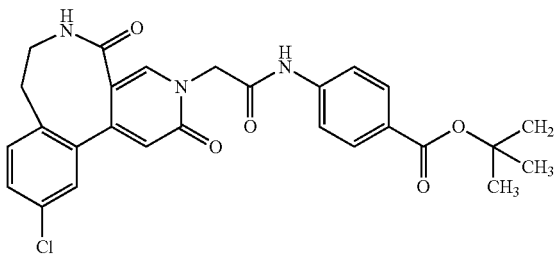 [SMILES: CC(C)(C)OC(=O)c1ccc(NC(=O)Cn2cc3c(cc2=O)-c2cc(Cl)ccc2CCNC3=O)cc1]

15 mg (45 μmol) of (11-chloro-2,5-dioxo-5,6,7,8-tetrahydropyrido[3,4-e][3]benzazocin-3(2H)-yl)acetic acid were dissolved in 0.5 ml of dimethylformamide, and 8.7 mg (45 μmol) of tert-butyl 4-aminobenzoate and 0.64 mg (4.5 μmol) of Oxyma were added. Subsequently, 7.0 μl (45 μmol) of di-iso-propylcarbodiimide were added dropwise and the reaction mixture was agitated at 40° C. over the weekend. The solvent was removed under reduced pressure and the residue was purified by means of preparative HPLC [column: Chromatorex C18, 10 μm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 5.7 mg (21% purity, 5% of theory)

LC/MS [Method 2]: $R_t$=2.94 min; MS (ESIpos): m/z=508 (M+H)$^+$.

Example 6.1A tert-Butyl 2-aminobutanoate (Racemate)

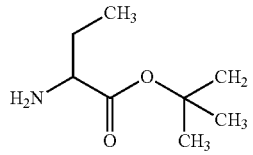

10.0 g (44.8 mmol) of tert-butyl 2-bromobutanoate (racemate) were initially charged in 30 ml THF, and 800 ml of aqueous ammonium hydroxide solution (25%) were added at room temperature. The mixture was stirred for a further 96 h and then all volatile constituents were removed on a rotary evaporator at 100 mbar and bath temperature 35 to 38° C. The aqueous phase was extracted three times with 200 ml of dichloromethane. The combined organic phases were dried and filtered, and the solvent was removed under reduced pressure at bath temperature 35° C. Yield: 5.40 g (74% of theory)

$^1$H-NMR (400 MHz, CDCl$_3$): δ [ppm]=3.28-3.24 (m, 1H), 1.76-1.66 (m, 1H), 1.64-1.53 (m, 1H), 1.45 (s, 9H), 0.94 (t, 3H).

Example 6.1B

Ethyl 1-(1-tert-butoxy-1-oxobutan-2-yl)-4-hydroxy-6-oxo-1,6-dihydropyridine-3-carboxylate (Racemate)

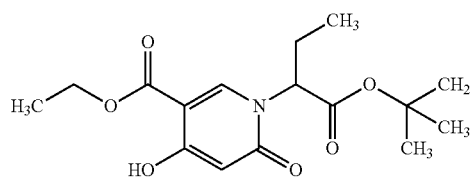 [SMILES: CCOC(=O)c1cn(C(CC)C(=O)OC(C)(C)C)c(=O)cc1O]

2.66 ml (14.7 mmol) of diethyl 3-oxopentanedicarboxylate and 3.35 ml (20.5 mmol, 1.4 eq.) of diethoxymethyl acetate were stirred at 100° C. for 2.5 h, and the mixture was cooled to RT, then co-evaporated three times with toluene and dried under high vacuum. The residue was taken up in 29.4 ml of ethanol, a solution of 2.50 g (15.4 mmol, 1.05 eq.) of tert-butyl 2-aminobutanoate (racemate) in ethanol was added while cooling with ice and the mixture was stirred at RT for 2 h. Subsequently, the reaction mixture was admixed with 5.47 ml (14.7 mmol, 1.0 eq.) of a sodium ethoxide solution (21% in ethanol) and stirred at RT for 1 h. The reaction was terminated by addition of 100 ml of saturated aqueous ammonium chloride solution and 50 ml of ethyl acetate. The phases were separated and the aqueous phase was extracted three times with 50 ml of ethyl acetate. The combined organic phases were washed with saturated aqueous sodium chloride solution, dried over magnesium sulphate and filtered, and the solvent was removed under reduced pressure. The residue was purified by means of flash chromatography (silica gel 50, cyclohexane/ethyl acetate mixture). Yield: 2.86 g (60% of theory)

LC/MS [Method 1]: $R_t$=1.00 min; MS (ESIpos): m/z=326 (M+H)$^+$, $^1$H-NMR (400 MHz, DMSO-d$_6$): δ [ppm]=10.9 (s, 1H), 8.33 (s, 1H), 5.70 (s, 1H), 4.99 (dd, 1H), 4.29 (q, 2H), 2.12-1.92 (m, 2H), 1.37 (s, 9H), 1.30 (t, 3H), 0.79 (t, 3H).

Example 6.1C

Ethyl 1-(1-tert-butoxy-1-oxobutan-2-yl)-6-oxo-4-{[(trifluoromethyl)sulphonyl]oxy}-1,6-dihydropyridine-3-carboxylate (Racemate)

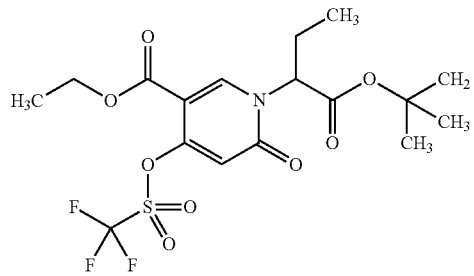 [SMILES: CCOC(=O)c1cn(C(CC)C(=O)OC(C)(C)C)c(=O)cc1OS(=O)(=O)C(F)(F)F]

To a solution of 2.86 g (8.79 mmol) of ethyl 1-(1-tert-butoxy-1-oxobutan-2-yl)-4-hydroxy-6-oxo-1,6-dihydropyridine-3-carboxylate (racemate) in 20 ml of dichloromethane were added, under argon at −78° C., 2.45 ml (17.6 mmol, 2.0 eq.) of triethylamine and then, in portions, 5.99 g (14.1 mmol, 1.6 eq.) of N-(4-tert-butylphenyl)-1,1,1-trifluoro-N-[(trifluoromethyl)sulphonyl]methanesulphonamide. The reaction mixture was allowed to come to RT and stirred at RT overnight, and then the solvent was removed under reduced pressure. The residue was purified by means of flash chromatography (silica gel 50, cyclohexane/ethyl acetate mixture). Yield: 2.76 g (69% of theory)

LC/MS [Method 1]: $R_t$=1.23 min; MS (ESIneg): m/z=456 (M−H)$^-$, $^1$H-NMR (400 MHz, DMSO-d$_6$): δ [ppm]=8.66 (s, 1H), 6.68 (s, 1H), 5.10 (dd, 1H), 4.31 (q, 2H), 2.19-1.99 (m, 2H), 1.37 (s, 9H), 1.31 (t, 3H), 0.83 (t, 3H).

Example 6.1D

Ethyl 4-(2-{2-[(tert-butoxycarbonyl)amino]ethyl}-5-chlorophenyl)-1-(1-tert-butoxy-1-oxobutan-2-yl)-6-oxo-1,6-dihydropyridine-3-carboxylate (Stereoisomer Mixture)

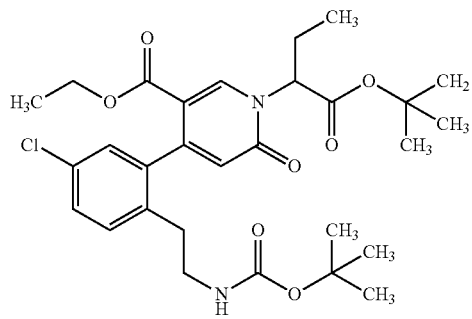 [SMILES: CCOC(=O)c1cn(C(CC)C(=O)OC(C)(C)C)c(=O)cc1-c1cc(Cl)ccc1CCNC(=O)OC(C)(C)C]

429 mg (3.10 mmol) of potassium carbonate were dried in the reaction vessel and then 473 mg (1.03 mmol) of ethyl 1-(1-tert-butoxy-1-oxobutan-2-yl)-6-oxo-4-{[(trifluoromethyl)sulphonyl]oxy}-1,6-dihydropyridine-3-carboxylate (racemate), 671 mg (1.76 mmol) of tert-butyl {2-[4-chloro-2-(4,4,5,5-tetramethyl-1,3,2-dioxaborolan-2-yl)phenyl]ethyl}carbamate and 10 ml of 1,4-dioxane were added. The reaction mixture was degassed, 119 mg (103 μmol) of tetrakis(triphenylphosphine)palladium(0) were added and the mixture was stirred at 110° C. overnight. The mixture was cooled down to room temperature and filtered through Celite, and the solvent was removed under reduced pressure. The residue was purified by means of flash chromatography (silica gel 50, cyclohexane/ethyl acetate mixture). Yield: 330 mg (96% purity, 54% of theory)

LC/MS [Method 1]: $R_t$=1.33 min; MS (ESIpos): m/z=563 (M+H)$^+$, $^1$H-NMR (400 MHz, DMSO-d$_6$): δ [ppm]=8.45/8.44 (2×s, 1H), 7.39-7.35 (m, 1H), 7.27/7.24 (2×d, 1H), 7.17/7.14 (2×d, 1H), 6.75-6.66 (m, 1H), 6.28/6.27 (2×s, 1H), 5.16-5.07 (m, 1H), 3.99-3.91 (m, 2H), 3.03-2.95 (m, 2H), 2.57-2.40 (m, 2H), 2.21-2.01 (m, 2H), 1.41/1.40 (2×s, 9H), 1.31 (s, 9H), 0.93-0.85 (m, 6H).

Example 6.1E

2-{4-[2-(2-Aminoethyl)-5-chlorophenyl]-5-(ethoxy-carbonyl)-2-oxopyridin-1(2H)-yl}butanoic acid (Stereoisomer Mixture)

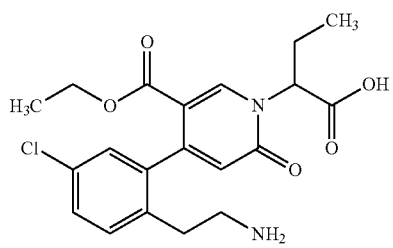 [SMILES: CCOC(=O)c1cn(C(CC)C(=O)O)c(=O)cc1-c1cc(Cl)ccc1CCN]

330 mg (586 µmol) of ethyl 4-(2-{[(tert-butoxycarbonyl)amino]ethyl}-5-chlorophenyl)-1-(2-tert-butoxy-2-oxobutan-2-yl)-6-oxo-1,6-dihydropyridine-3-carboxylate (stereoisomer mixture) were initially charged in 5.5 ml of dichloromethane, and 1.36 ml (17.6 mmol) of trifluoroacetic acid were added. The mixture was stirred at room temperature for a further 6 h. Subsequently, the solvent was removed under reduced pressure and the residue was co-evaporated twice with 20 ml of toluene. Yield: 328 mg (95% purity, quantitative)

LC/MS [Method 1]: $R_t$=0.72 min; MS (ESIpos): m/z=407 (M+H)$^+$, $^1$H-NMR (400 MHz, DMSO-d$_6$): δ [ppm]=13.2 (br. s, 1H), 8.51/8.49 (2×s, 1H), 7.69 (br. s, 2H), 7.44 (dd, 1H), 7.35 (d, 1H), 7.23-7.21 (m, 1H), 6.31 (s, 1H), 5.23-5.17 (m, 1H), 4.00-3.94 (m, 2H), 3.00-2.85 (m, 2H), 2.77-2.58 (m, 2H), 2.25-2.03 (m, 2H), 0.94 (t, 3H), 0.88 (2×t, 3H).

Example 6.1F 2-(11-Chloro-2,5-dioxo-5,6,7,8-tetrahydropyrido[3,4-e][3]benzazocin-3(2H)-yl)butanoic acid (Stereoisomer Mixture)

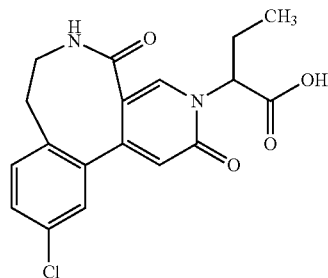 [SMILES: CCC(C(=O)O)n1cc2c(cc1=O)-c1cc(Cl)ccc1CCNC2=O]

A solution of 238 mg (585 µmol) of 2-{4-[2-(2-aminoethyl)-5-chlorophenyl]-5-(ethoxycarbonyl)-2-oxopyridin-1(2H)-yl}butanoic acid (stereoisomer mixture) in 6 ml of tetrahydrofuran was added under argon to activated 3 Å molecular sieve (dried at 200° C. in a drying cabinet overnight) and stirred at RT for 2 h. Subsequently, the reaction mixture was admixed under argon at RT with 437 µl (1.17 mmol, 2 eq.) of a sodium ethoxide solution (21% in ethanol, dried beforehand over activated 3 Å molecular sieve for 2 h) and stirred at room temperature for 40 min. After diluting with ethyl acetate, saturated aqueous ammonium chloride solution was added to the reaction mixture. The phases were separated and the aqueous phase was extracted three times with ethyl acetate. The aqueous phase was then brought to pH 3 with aqueous hydrochloric acid solution (1 N) and extracted again with ethyl acetate. The combined organic phases were dried (sodium sulphate) and filtered, and the solvent was removed under reduced pressure. Yield: 184 mg (87% of theory)

LC/MS [Method 1]: $R_t$=0.68 min; MS (ESIpos): m/z=361 (M+H)$^+$, $^1$H-NMR (400 MHz, DMSO-d$_6$): δ [ppm]=13.1 (br. s, 1H), 7.80/7.79 (2×s, 1H), 7.78-7.73 (m, 1H), 7.45 (dd, 1H), 7.31 (d, 1H), 7.28-7.26 (m, 1H), 6.30 (2×s, 1H), 5.13/5.03 (2×dd, 1H), 3.45-3.23 (m, 2H), 2.98-2.89 (m, 2H), 2.18-2.05 (m, 2H), 0.84/0.83 (2×t, 3H).

Example 6.1G tert-Butyl 4-{[2-(11-chloro-2,5-dioxo-5,6,7,8-tetrahydropyrido[3,4-e][3]benzazocin-3(2H)-yl)butanoyl]amino}benzoate (Stereoisomer Mixture)

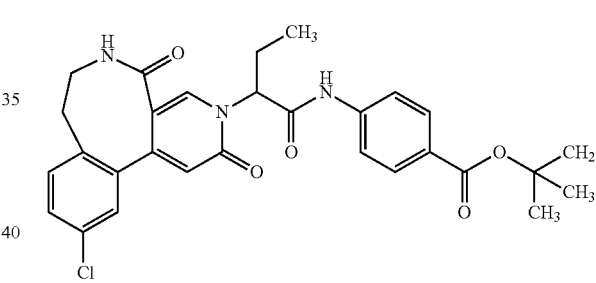

184 mg (510 µmol) of 2-(11-chloro-2,5-dioxo-5,6,7,8-tetrahydropyrido[3,4-e][3]benzazocin-3(2H)-yl)butanoic acid (stereoisomer mixture) were dissolved in 5 ml of dimethylformamide, and 98.6 mg (510 µmol) of tert-butyl 4-aminobenzoate and 72.5 mg (510 µmol) of Oxyma were added. Subsequently, 79.5 µl (510 µmol) of di-iso-propylcarbodiimide were added dropwise and the reaction mixture was agitated at 40° C. overnight. The solvent was removed under reduced pressure and the residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 156 mg (97% purity, 55% of theory)

LC/MS [Method 1]: $R_t$=1.07 min; MS (ESIpos): m/z=536 (M+H)$^+$, $^1$H-NMR (400 MHz, DMSO-d$_6$): δ [ppm]=10.8 (s, 1H), 7.90-7.71 (m, 6H), 7.48-7.43 (m, 1H), 7.31 (d, 1H), 7.29-7.26 (m, 1H), 6.34/6.33 (2×s, 1H), 5.63-5.55 (m, 1H), 3.48-3.23 (m, 2H), 2.99-2.90 (m, 2H), 2.24-2.03 (m, 2H), 1.54 (s, 9H), 0.91/0.90 (2×t, 3H).

Example 7.1A tert-Butyl 2-(1,3-dioxo-1,3-dihydro-2H-isoindol-2-yl)-4-methylpentanoate (Racemate)

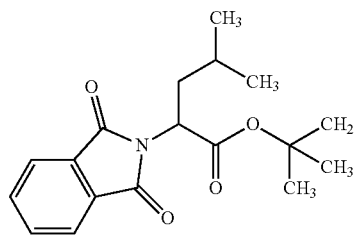 [SMILES: CC(C)CC(C(=O)OC(C)(C)C)N1C(=O)c2ccccc2C1=O]

10.0 g (38.3 mmol) of 2-(1,3-dioxo-1,3-dihydro-2H-isoindol-2-yl)-4-methylpentanoic acid (racemate) were dissolved in a mixture of 6 ml of THF and 6 ml of tert-butanol. Subsequently, 8.77 g (40.2 mmol) of di-tert-butyl dicarbonate in portions and 1.40 g (11.5 mmol) of 4-dimethylaminopyridine were added. The mixture was stirred at room temperature overnight. The reaction mixture was diluted with 150 ml of ethyl acetate, and washed with 100 ml of saturated aqueous ammonium chloride solution, 100 ml of water and 100 ml of saturated aqueous sodium chloride solution. The organic phase was dried over sodium sulphate and filtered, and the solvent was removed under reduced pressure. The residue was purified by means of flash chromatography (silica gel 50, cyclohexane/ethyl acetate mixture). Yield: 11.4 g (96% purity, 90% of theory).

LC/MS [Method 1]: $R_t$=1.27 min; MS (ESIpos): m/z=318 $(M+H)^+$, $^1$H-NMR (400 MHz, DMSO-$d_6$): δ [ppm]=7.96-7.87 (m, 4H), 4.77 (dd, 1H), 2.18-2.08 (m, 1H), 1.87-1.78 (m, 1H), 1.50-1.39 (m, 1H), 1.34 (s, 9H), 0.89-0.85 (m, 6H).

Example 7.1B

Tert-Butyl Leucinate (Racemate)

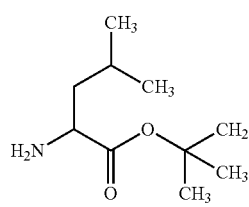

To a solution of 11.3 g (35.6 mmol) of tert-butyl 2-(1,3-dioxo-1,3-dihydro-2H-isoindol-2-yl)-4-methylpentanoate (racemate) in tert-butanol were added 4.33 ml (71.2 mmol) of hydrazine hydrate (80% in water), and the mixture was heated to boiling for 1 min. Subsequently, it was stirred with water and sodium carbonate until the precipitate formed went into solution. The mixture was extracted three times with diethyl ether and then acidified to pH 5 with hydrochloric acid (5 M in cyclopentyl methyl ether). It was extracted once more with diethyl ether. The combined diethyl ether phases did not contain any product and were discarded. The aqueous phase was diluted with ethyl acetate and water. The phases were separated and the aqueous phase was extracted with ethyl acetate. The combined organic phases were dried over magnesium sulphate and filtered, and the solvent was removed under reduced pressure (100 mbar, water bath temperature 35° C.). Yield: 5.65 g (39% purity, 33% of theory).

GC/MS [Method 9]: $R_t$=2.81 min; MS: m/z=187 $(M)^+$.

Example 7.1C

Ethyl 1-(1-tert-butoxy-4-methyl-1-oxopentan-2-yl)-4-hydroxy-6-oxo-1,6-dihydropyridine-3-carboxylate (Racemate)

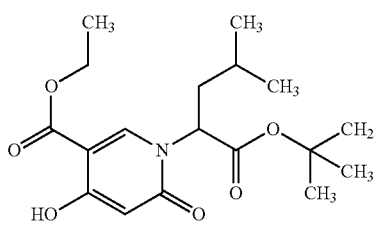 [SMILES: CCOC(=O)c1cn(C(CC(C)C)C(=O)OC(C)(C)C)c(=O)cc1O]

462 µl (2.54 mmol) of diethyl 3-oxopentanedicarboxylate and 581 µl (3.56 mmol, 1.4 eq.) of diethoxymethyl acetate were stirred at 100° C. for 2.5 h. After cooling to room temperature, the mixture was coevaporated three times with toluene and dried under high vacuum. The residue was taken up in 2.5 ml of ethanol, a solution of 500 mg (2.67 mmol, 1.05 eq.) of tert-butyl leucinate (racemate) in ethanol was added while cooling with ice and the mixture was stirred at room temperature overnight. Subsequently, the reaction mixture was admixed with 949 µl (2.54 mmol, 1.0 eq.) of a sodium ethoxide solution (21% in ethanol) and stirred at room temperature overnight. The reaction was ended by adding saturated aqueous ammonium chloride solution and ethyl acetate. The phases were separated and the aqueous phase was extracted three times with ethyl acetate. The combined organic phases were washed with saturated aqueous sodium chloride solution, dried over magnesium sulphate and filtered, and the solvent was removed under reduced pressure. The residue was purified by means of flash chromatography (silica gel 50, cyclohexane/ethyl acetate mixture) and preparative HPLC (iso-hexane/iso-propanol mixture). Yield: 154 mg (90% purity, 15% of theory)

LC/MS [Method 1]: $R_t$=1.17 min; MS (ESIpos): m/z=354 $(M+H)^+$, $^1$H-NMR (400 MHz, DMSO-$d_6$): δ [ppm]=10.9 (s, 1H), 8.33 (s, 1H), 5.71 (s, 1H), 5.22 (dd, 1H), 4.29 (q, 2H), 2.02-1.93 (m, 1H), 1.88-1.79 (m, 1H), 1.38 (s, 9H), 1.38-1.27 (m, 1H), 1.30 (t, 3H), 0.88-0.83 (m, 6H).

Example 7.1D

Ethyl 1-(1-tert-butoxy-4-methyl-1-oxopentan-2-yl)-6-oxo-4-{[(trifluoromethyl)sulphonyl]oxy}-1,6-dihydropyridine-3-carboxylate (Racemate)

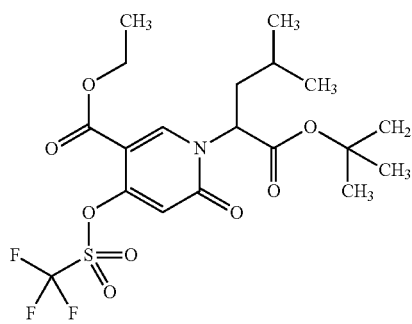 [SMILES: CCOC(=O)c1cn(C(CC(C)C)C(=O)OC(C)(C)C)c(=O)cc1OS(=O)(=O)C(F)(F)F]

To a solution of 140 mg (396 μmol) of ethyl 1-(1-tert-butoxy-4-methyl-1-oxopentan-2-yl)-4-hydroxy-6-oxo-1,6-dihydropyridine-3-carboxylate (racemate) in 1 ml of dichloromethane were added, under argon at −78° C., 110 μl (792 μmol, 2.0 eq.) of triethylamine and then, in portions, 262 mg (634 μmol, 1.6 eq.) of N-(4-tert-butylphenyl)-1,1,1-trifluoro-N-[(trifluoromethyl)sulphonyl]methanesulphonamide. The reaction mixture was allowed to come to room temperature and stirred at room temperature overnight, and then the solvent was removed under reduced pressure. The residue was purified by means of flash chromatography (silica gel 50, cyclohexane/ethyl acetate mixture). Yield: 169 mg (94% purity, 82% of theory)

LC/MS [Method 1]: $R_t$=1.33 min; MS (ESIpos): m/z=486 (M+H)$^+$, $^1$H-NMR (400 MHz, DMSO-d$_6$): δ [ppm]=8.67 (s, 1H), 6.70 (s, 1H), 5.29 (dd, 1H), 4.32 (q, 2H), 2.08-2.00 (m, 1H), 1.96-1.88 (m, 1H), 1.37 (s, 9H), 1.43-1.33 (m, 1H), 1.31 (t, 3H), 0.89 (d, 3H), 0.87 (d, 3H).

Example 7.1E

Ethyl 4-(2-{2-[(tert-butoxycarbonyl)amino]ethyl}-5-chlorophenyl)-1-(1-tert-butoxy-4-methyl-1-oxopentan-2-yl)-6-oxo-1,6-dihydropyridine-3-carboxylate (Stereoisomer Mixture)

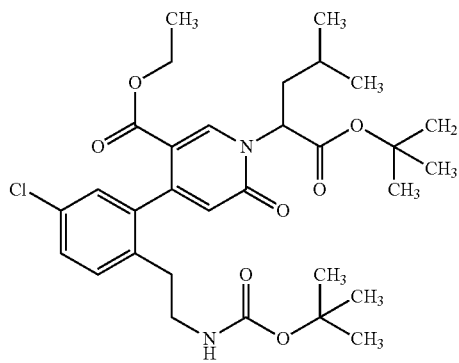 [SMILES: CCOC(=O)c1cn(C(CC(C)C)C(=O)OC(C)(C)C)c(=O)cc1-c1cc(Cl)ccc1CCNC(=O)OC(C)(C)C]

115 mg (834 μmol) of potassium carbonate were dried in the reaction vessel and then 135 mg (278 μmol) of ethyl 1-(1-tert-butoxy-4-methyl-1-oxopentan-2-yl)-6-oxo-4-{[(trifluoromethyl)sulphonyl]oxy}-1,6-dihydropyridine-3-carboxylate (racemate), 122 mg (320 μmol) of tert-butyl (2-[4-chloro-2-(4,4,5,5-tetramethyl-1,3,2-dioxaborolan-2-yl)phenyl]ethyl)carbamate and 2.6 ml of 1,4-dioxane were added. The reaction mixture was degassed, 32 mg (28 μmol) of tetrakis(triphenylphosphine)palladium(0) were added and the mixture was stirred at 110° C. for 6 h, at room temperature overnight and at 110° C. for a further 2 h. The mixture was cooled down to room temperature and filtered through Celite, and the solvent was removed under reduced pressure. The residue was purified by means of flash chromatography (silica gel 50, cyclohexane/ethyl acetate mixture). Yield: 106 mg (93% purity, 60% of theory)

LC/MS [Method 1]: $R_t$=1.46 min; MS (ESIpos): m/z=591 (M+H)$^+$.

Example 7.1F

2-{4-[2-(2-Aminoethyl)-5-chlorophenyl]-5-(ethoxycarbonyl)-2-oxopyridin-1 (2H)-yl}4-methylpentanoic acid (Stereoisomer Mixture)

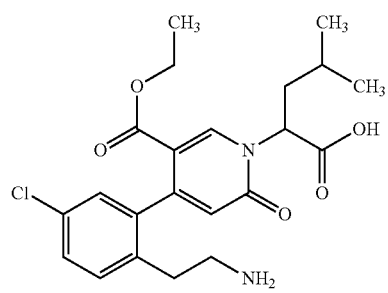 [SMILES: CCOC(=O)c1cn(C(CC(C)C)C(=O)O)c(=O)cc1-c1cc(Cl)ccc1CCN]

85.0 mg (144 μmol) of ethyl 4-(2-{2-[(tert-butoxycarbonyl)amino]ethyl}-5-chlorophenyl)-1-(1-tert-butoxy-4-methyl-1-oxopentan-2-yl)-6-oxo-1,6-dihydropyridine-3-carboxylate (stereoisomer mixture) were initially charged in 1.5 ml of dichloromethane, and 415 μl (5.39 mmol) of trifluoroacetic acid were added. The mixture was stirred at room temperature for a further 4 h. Subsequently, the solvent was removed under reduced pressure and the residue was co-evaporated twice with 20 ml of toluene. Yield: 328 mg (95% purity, quantitative)

LC/MS [Method 1]: $R_t$=0.79 min; MS (ESIpos): m/z=435 (M+H)$^+$.

Example 7.1G 2-(11-Chloro-2,5-dioxo-5,6,7,8-tetrahydropyrido[3,4-e][3]benzazocin-3(2H)-yl)-4-methylpentanoic acid (Stereoisomer Mixture)

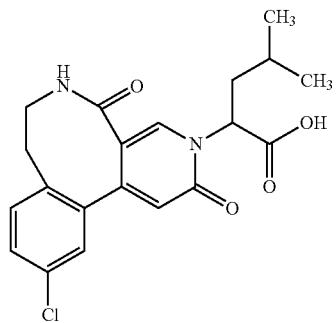 [SMILES: CC(C)CC(C(=O)O)n1cc2c(cc1=O)-c1cc(Cl)ccc1CCNC2=O]

A solution of 66.0 mg (152 μmol) of 2-{4-[2-(2-aminoethyl)-5-chlorophenyl]-5-(ethoxycarbonyl)-2-oxopyridin-1 (2H)-yl}-4-methylpentanoic acid (stereoisomer mixture) in 1.5 ml of tetrahydrofuran was added under argon to activated 3 Å molecular sieve (dried at 200° C. in a drying cabinet overnight) and stirred at RT for 2 h. Subsequently, the reaction mixture was admixed under argon at RT with 113 μl (304 μmol, 2 eq.) of a sodium ethoxide solution (21% in ethanol, dried beforehand over activated 3 Å molecular sieve for 2 h) and stirred at room temperature for 40 min. Another 55.0 μl (152 μmol) of a sodium ethoxide solution (21% in ethanol, dried beforehand over activated 3 Å molecular sieve for 2 h) were added and the mixture was stirred at room temperature overnight. After diluting with ethyl acetate, saturated aqueous ammonium chloride solution was added to the reaction mixture. The phases were separated and the aqueous phase was extracted three times with ethyl acetate. The aqueous phase was then brought to pH 3 with aqueous hydrochloric acid solution (1N) and extracted again with ethyl acetate. The combined organic phases were dried (sodium sulphate) and filtered, and the solvent was removed under reduced pressure. Yield: 31.3 mg (96% purity, 51% of theory)

LC/MS [Method 1]: $R_t$=0.78/0.80 min; MS (ESIpos): m/z=389 (M+H)$^+$, $^1$H-NMR (400 MHz, DMSO-d$_6$): δ [ppm]=13.2 (br. s, 1H), 7.82 (2×s, 1H), 7.80-7.74 (m, 1H), 7.45 (dd, 1H), 7.33-7.26 (m, 2H), 6.30 (s, 1H), 5.39-5.27 (m, 1H), 3.42-3.23 (m, 2H), 3.00-2.87 (m, 2H), 2.19-2.09 (m, 1H), 1.94-1.86 (m, 1H), 1.44-1.33 (m, 1H), 0.92-0.87 (m, 6H).

Example 7.1H tert-Butyl 4-{[2-(1-chloro-2,5-dioxo-5,6,7,8-tetrahydropyrido[3,4-e][3]benzazocin-3(2H)-yl)-4-methylpentanoyl]amino}benzoate (Stereoisomer Mixture)

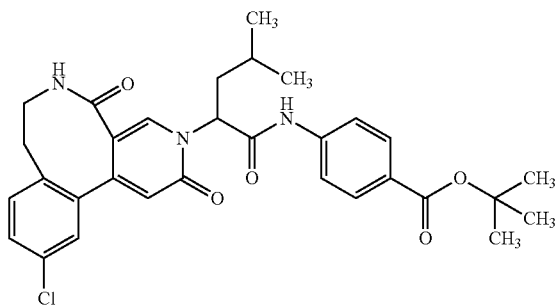 [SMILES: CC(C)CC(C(=O)Nc1ccc(C(=O)OC(C)(C)C)cc1)n1cc2c(cc1=O)-c1cc(Cl)ccc1CCNC2=O]

15 mg (39 µmol) of 2-(11-chloro-2,5-dioxo-5,6,7,8-tetrahydropyrido[3,4-e][3]benzazocin-3(2H)-yl)-4-methylpentanoic acid (stereoisomer mixture) were dissolved in 400 µl of dimethylformamide, and 7.5 mg (39 µmol) of tert-butyl 4-aminobenzoate and 5.5 mg (39 µmol) of Oxyma were added. 6.0 µl (39 µmol) of di-iso-propylcarbodiimide were added dropwise and the reaction solution was agitated at 40° C. overnight. Subsequently, a further 1.5 mg (8.0 µmol) tert-butyl 4-aminobenzoate and 1.2 µl (8.0 µmol) of di-iso-propylcarbodiimide were added and the mixture was agitated at 40° C. for a further 3 h. The solvent was removed under reduced pressure and the residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 13.9 mg (64% of theory)

LC/MS [Method 1]: $R_t$=1.16 min; MS (ESIpos): m/z=564 (M+H)$^+$, $^1$H-NMR (400 MHz, DMSO-d$_6$): δ [ppm]=10.9 (2×s, 1H), 7.91-7.72 (m, 6H), 7.48-7.43 (m, 1H), 7.33-7.27 (m, 2H), 6.34/6.33 (2×s, 1H), 5.87-5.80 (m, 1H), 3.47-3.23 (m, 2H), 3.02-2.87 (m, 2H), 2.19-2.09 (m, 1H), 1.93-1.83 (m, 1H), 1.54 (s, 9H), 1.49-1.38 (m, 1H), 0.96-0.91 (m, 6H).

Example 8.1A

Ethyl 4-[(2-{1-[(tert-butoxycarbonyl)amino] cyclopropyl}methyl)-5-chlorophenyl]-1-(1-tert-butoxy-1-oxobutan-2-yl)-6-oxo-1,6-dihydropyridine-3-carboxylate (Stereoisomer Mixture)

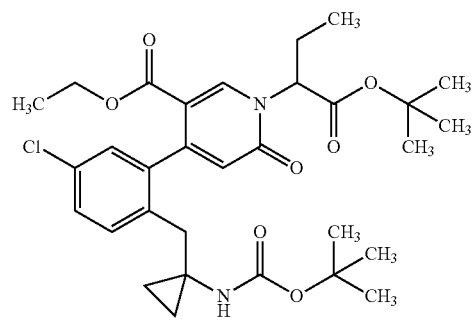 [SMILES: CCOC(=O)c1cn(C(CC)C(=O)OC(C)(C)C)c(=O)cc1-c1cc(Cl)ccc1CC1(NC(=O)OC(C)(C)C)CC1]

629 mg (4.55 mmol) of potassium carbonate were dried in the reaction vessel and then 672 mg (1.47 mmol) of ethyl 1-(1-tert-butoxy-1-oxobutan-2-yl)-6-oxo-4-{[(trifluoromethyl)sulphonyl]oxy}-1,6-dihydropyridine-3-carboxylate (racemate), 800 mg (1.47 mmol) of [(2-(1-[(tert-butoxycarbonyl)amino]cyclopropyl)methyl)-5-chlorophenyl]boric acid (60% purity) and 14.7 ml of 1,4-dioxane were added. The reaction mixture was degassed, 170 mg (147 µmol) of tetrakis(triphenylphosphine)palladium(0) were added and the mixture was agitated at 10° C. overnight. The mixture was cooled down to room temperature and filtered through a fine filter, and the solvent was removed under reduced pressure. The residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 249 mg (29% of theory)

LC/MS [Method 1]: $R_t$=1.35 min; MS (ESIpos): m/z=589 (M+H)$^+$.

Example 8.1B

2-[4-{2-[(1-Aminocyclopropyl)methyl]-5-chlorophenyl}-5-(ethoxycarbonyl)-2-oxopyridin-1(2H)-yl] butanoic acid (Stereoisomer Mixture)

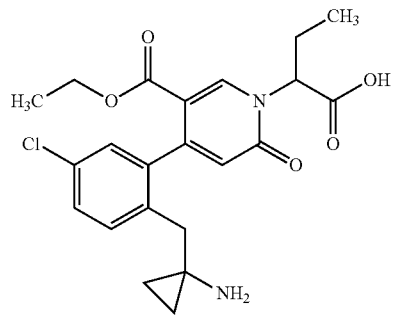 [SMILES: CCOC(=O)c1cn(C(CC)C(=O)O)c(=O)cc1-c1cc(Cl)ccc1CC1(N)CC1]

249 mg (423 µmol) of ethyl 4-[2-{1-[(tert-butoxycarbonyl)amino]cyclopropyl}methyl)-5-chlorophenyl]-1-(1-tert-butoxy-1-oxobutan-2-yl)-6-oxo-1,6-dihydropyridine-3-carboxylate (stereoisomer mixture) were initially charged in 4 ml of dichloromethane, and 651 µl (8.45 mmol) of trifluoroacetic acid were added. The mixture was stirred at room temperature for a further 2 h. Subsequently, the solvent was removed under reduced pressure and the residue was co-evaporated repeatedly with toluene. Yield: 263 mg (94% purity, quantitative)

LC/MS [Method 1]: $R_t$=0.68 min; MS (ESIpos): m/z=433 (M+H)$^+$.

Example 8.1C 2-(11'-Chloro-2',5'-dioxo-2',5',6',8'-tetrahydro-3'H-spiro[cyclopropan-1,7'-pyrido[3,4-e][3]benzazocine]-3'-yl)butanoic acid (Stereoisomer Mixture)

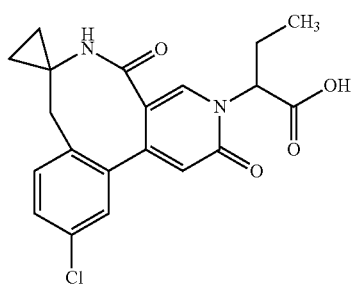 [SMILES: CCC(C(=O)O)n1cc2c(cc1=O)-c1cc(Cl)ccc1CC1(CC1)NC2=O]

A solution of 263 mg (553 µmol) of 2-[4-{2-[(1-aminocyclopropyl)methyl]-5-chlorophenyl}-5-(ethoxycarbonyl)-2-oxopyridin-1(2H)-yl]butanoic acid (stereoisomer mixture) in 5 ml of tetrahydrofuran was added under argon to activated 3 Å molecular sieve (dried at 200° C. in a drying cabinet overnight) and stirred at RT for 2 h. Subsequently, the reaction mixture was admixed under argon at RT with 4.13 ml (11.1 mmol, 20 eq.) of a sodium ethoxide solution (21% in ethanol, dried beforehand over activated 3 Å molecular sieve for 2 h) and stirred at room temperature for 45 min. After dilution with ethyl acetate, the reaction mixture was admixed with saturated aqueous ammonium chloride solution and brought to pH 3 with aqueous hydrochloric acid solution (1 N) and extracted again with ethyl acetate. The combined organic phases were dried (sodium sulphate) and filtered, and the solvent was removed under reduced pressure. The residue was taken up once again in 50 ml of ethyl acetate and filtered through Celite. The filtrate was washed twice with 25 ml of aqueous hydrochloric acid (0.5 M) and 20 ml of saturated aqueous sodium chloride solution, dried over magnesium sulphate and filtered, and the solvent was removed under reduced pressure. Yield: 124 mg (94% purity, 54% of theory)

LC/MS [Method 1]: $R_t$=0.72/0.74 min; MS (ESIpos): m/z=387 (M+H)$^+$.

Example 8.1D tert-Butyl 4-{[2-(11'-chloro-2',5'-dioxo-2',5',6',8'-tetrahydro-3'H-spiro[cyclopropane-1,7'-pyrido[3,4-e][3]benzazocine]-3'-yl)butanoyl]amino}benzoate (Stereoisomer Mixture)

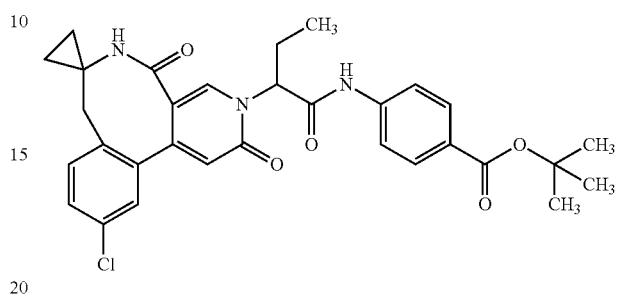

90.0 mg (219 µmol) of 2-(11'-chloro-2',5'-dioxo-2',5',6',8'-tetrahydro-3'H-spiro[cyclopropane-1,7'-pyrido[3,4-e][3]benzazocine]-3'-yl)butanoic acid (stereoisomer mixture) were dissolved in 2.2 ml of dimethylformamide, and 42.3 mg (219 µmol) of tert-butyl 4-aminobenzoate and 21.8 mg (153 µmol) of Oxyma were added. Subsequently, 34.1 µl (219 µmol) of di-iso-propylcarbodiimide were added dropwise and the reaction solution was agitated at 40° C. overnight. The solvent was removed under reduced pressure and the residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile]. Yield: 87.2 mg (71% of theory)

LC/MS [Method 1]: $R_t$=1.08 min; MS (ESIpos): m/z=562 (M+H)$^+$, $^1$H-NMR (400 MHz, DMSO-d$_6$): δ [ppm]=10.8 (2×s, 1H), 8.15/8.09 (2×s, 1H), 7.90-7.68 (m, 5H), 7.45 (dd, 1H), 7.33-7.27 (m, 2H), 6.33/6.32 (2×s, 1H), 5.72/5.62 (2×dd, 1H), 3.28-3.16 (m, 1H), 2.74-2.63 (m, 1H), 2.23-2.05 (m, 2H), 1.54 (s, 9H), 1.04-0.87 (m, 4H), 0.80-0.65 (m, 3H).

Example 9.1A tert-Butyl N-(diphenylmethylene)-O-methylhomoserinate (Racemate)

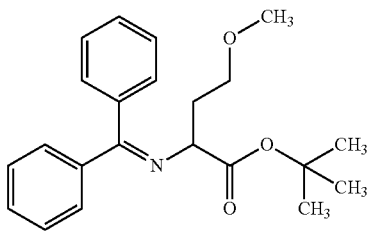 [SMILES: COCCC(N=C(c1ccccc1)c1ccccc1)C(=O)OC(C)(C)C]

To a solution of 4.43 g (15.0 mmol) of tert-butyl N-(diphenylmethylene)glycinate in 150 ml of tetrahydrofuran were added dropwise, under argon at −78° C., 19.5 ml (1.0 M in THF, 19.5 mmol, 1.3 eq.) of lithium bis(trimethylsilyl) amide, the mixture was stirred for 15 min, and then 5.85 g (80% purity, 22.5 mmol, 1.5 eq.) of 2-methoxyethyl trifluoromethanesulphonate were added dropwise. The reaction mixture was stirred at −78° C. for a further 15 min, allowed to come to RT, stirred for another 30 min and then quenched with water. After addition of ethyl acetate and phase separation, the aqueous phase was extracted twice with ethyl acetate. The combined organic phases were washed with saturated aqueous sodium chloride solution, dried (sodium sulphate), filtered and concentrated under reduced pressure. The residue was purified by means of flash chromatography (silica gel 50, cyclohexane/ethyl acetate mixture). Yield: 4.61 g (87% of theory)

LC/MS [Method 1]: $R_t$=1.17 min; MS (ESIpos): m/z=354 (M+H)$^+$, $^1$H-NMR (400 MHz, DMSO-d$_6$): δ [ppm]=7.56-7.35 (m, 8H), 7.18-7.11 (m, 2H), 3.92 (dd, 1H), 3.38-3.32 (m, 1H), 3.26-3.17 (m, 1H), 3.12 (s, 3H), 2.10-1.91 (m, 2H), 1.37 (s, 9H).

Example 9.1B tert-Butyl O-methylhomoserinate (Racemate)

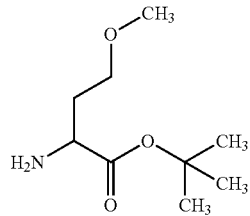

To a solution of 4.61 g (13.0 mmol) of tert-butyl N-(diphenylmethylene)-O-methylhomoserinate (racemate) in 150 ml of tetrahydrofuran were added 150 ml of an aqueous citric acid solution (1M) and the mixture was stirred at RT for 2 h. Subsequently, tetrahydrofuran was removed under reduced pressure. The resulting aqueous solution was neutralized cautiously with solid sodium bicarbonate and extracted twice with dichloromethane. The combined organic phases were dried (sodium sulphate), filtered and concentrated on a rotary evaporator under reduced pressure (>150 mbar at water bath temperature <25° C.). The residue was purified by means of flash chromatography (silica gel 50, dichloromethane/methanol mixture). Yield: 2.58 g (quant.)

GC/MS [Method 9]: $R_t$=3.26 min; MS: m/z=189 (M)$^+$, $^1$H-NMR (400 MHz, DMSO-d$_6$): δ [ppm]=3.48-3.39 (m, 1H), 3.39-3.33 (m, 1H), 3.25-3.14 (m, 1H), 3.21 (s, 3H), 1.84-1.73 (m, 1H), 1.66 (br. s, 1H), 1.60-1.50 (m, 1H), 1.40 (s, 9H).

Example 9.1C

Ethyl 1-(1-tert-butoxy-4-methoxy-1-oxobutan-2-yl)-4-hydroxy-6-oxo-1,6-dihydropyridine-3-carboxylate (Racemate)

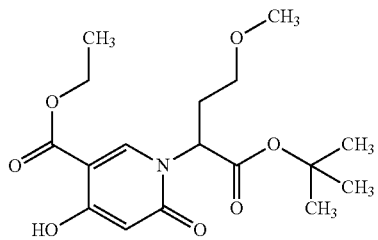 [SMILES: CCOC(=O)c1cn(C(CCOC)C(=O)OC(C)(C)C)c(=O)cc1O]

2.35 ml (90% purity, 11.7 mmol) of diethyl 3-oxopentanedicarboxylate and 2.67 ml (16.3 mmol, 1.4 eq.) of diethoxymethyl acetate were stirred at 100° C. for 2.5 h, and the mixture was cooled to RT, then co-evaporated three times with toluene and dried under high vacuum. The residue was taken up in 70 ml of ethanol, a solution of 2.32 g (12.2 mmol, 1.05 eq.) of tert-butyl O-methylhomoserinate (racemate) in 20 ml of ethanol was added while cooling with ice and the mixture was stirred at RT for 1 h. Subsequently, the reaction mixture was admixed with 4.36 ml (11.7 mmol, 1.0 eq.) of a sodium ethoxide solution (21% in ethanol, dried beforehand over about 15 g of activated 3 Å molecular sieve), stirred at RT for 1 h and quenched with saturated aqueous ammonium chloride solution. The solid that precipitates out was filtered, washed with ethyl acetate and discarded. After phase separation, the combined filtrates were extracted three times with ethyl acetate. The combined organic phases were washed with saturated aqueous sodium chloride solution, dried (sodium sulphate), filtered and concentrated under reduced pressure. The residue was purified by means of flash chromatography (silica gel 50, cyclohexane/ethyl acetate mixture). Yield: 2.37 g (56% of theory)

LC/MS [Method 1]: $R_t$=0.98 min; MS (ESIneg): m/z=354 (M−H)$^-$, $^1$H-NMR (400 MHz, DMSO-d$_6$): δ [ppm]=10.85 (s, 1H), 8.31 (s, 1H), 5.69 (s, 1H), 5.11 (dd, 1H), 4.36-4.23 (m, 2H), 3.38-3.32 (m, 1H), 3.15 (s, 3H), 3.14-3.07 (m, 1H), 2.31-2.14 (m, 2H), 1.37 (s, 9H), 1.29 (t, 3H).

Example 9.1D

Ethyl 1-(1-tert-butoxy-4-methoxy-1-oxobutan-2-yl)-6-oxo-4-{[(trifluoromethyl)sulphonyl]oxy}-1,6-dihydropyridine-3-carboxylate (Racemate)

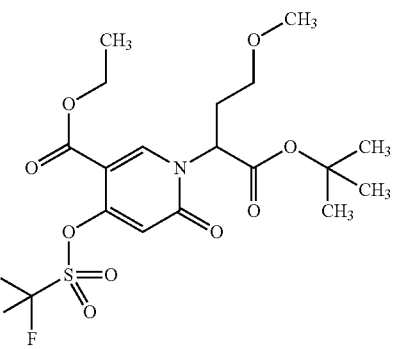

To a solution of 4.49 g (12.4 mmol) of ethyl 1-(1-tert-butoxy-4-methoxy-1-oxobutan-2-yl)-4-hydroxy-6-oxo-1,6-dihydropyridine-3-carboxylate (racemate) in 50 ml of dichloromethane were added, under argon at −78° C., 3.45 ml (24.8 mmol, 2.0 eq.) of triethylamine and then, in portions, 8.19 g (19.8 mmol, 1.6 eq.) of N-(4-tert-butylphenyl)-1,1,1-trifluoro-N-[(trifluoromethyl)sulphonyl]methanesulphonamide. The reaction mixture was allowed to come to RT, stirred at RT for 6 h and then concentrated under reduced pressure. The residue was purified by means of flash chromatography (silica gel 50, cyclohexane/ethyl acetate mixture). Yield: 4.85 g (76% of theory)

LC/MS [Method 1]: $R_t$=1.23 min; MS (ESIpos): m/z=488 (M+H)$^+$,

¹H-NMR (400 MHz, DMSO-d₆): δ [ppm]=8.65 (s, 1H), 6.66 (s, 1H), 5.27 (t, 1H), 4.38-4.25 (m, 2H), 3.44-3.36 (m, 1H), 3.23-3.14 (m, 1H), 3.11 (s, 3H), 2.35-2.24 (m, 2H), 1.36 (s, 9H), 1.30 (t, 3H).

Example 9.1E

Ethyl 4-[(2-{1-[(tert-butoxycarbonyl)amino]cyclopropyl}methyl)-5-chlorophenyl]-1-(1-tert-butoxy-4-methoxy-1-oxobutan-2-yl)-6-oxo-1,6-dihydropyridine-3-carboxylate (Stereoisomer Mixture)

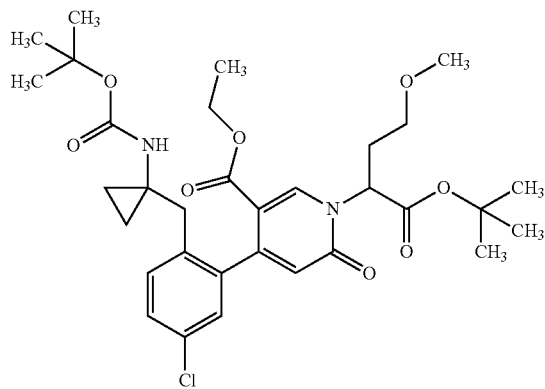 [SMILES: CCOC(=O)c1cn(C(CCOC)C(=O)OC(C)(C)C)c(=O)cc1-c1cc(Cl)ccc1CC1(NC(=O)OC(C)(C)C)CC1]

A mixture of 4.60 g (9.0 mmol) of ethyl 1-(1-tert-butoxy-4-methoxy-1-oxobutan-2-yl)-6-oxo-4-{[(trifluoromethyl)sulphonyl]oxy}-1,6-dihydropyridine-3-carboxylate (racemate), 4.14 g (10.3 mmol, 1.15 eq.) of [2-({1-[(tert-butoxycarbonyl)amino]cyclopropyl}methyl)-5-chlorophenyl]boric acid and 3.72 g (26.9 mmol, 3.0 eq.) of potassium carbonate was dried under high vacuum, placed under argon, 100 ml of dioxane were added and argon was passed through the mixture for 10 min. Subsequently, 732 mg (0.9 mmol, 0.1 eq.) of [1,1-bis(diphenylphosphino)ferrocene]palladium(II) chloride-monodichloromethane adduct were added to the reaction mixture, which was stirred at oil bath temperature 80° C. for 1 h. After cooling to RT, the reaction mixture was combined with a previous, analogously conducted test batch of 200 mg (0.39 mmol) of ethyl 1-(1-tert-butoxy-4-methoxy-1-oxobutan-2-yl)-6-oxo-4-{[(trifluoromethyl)sulphonyl]oxy}-1,6-dihydropyridine-3-carboxylate (racemate) and filtered through Celite. After washing with dioxane, the combined filtrates were concentrated under reduced pressure. The residue was taken up in water and extracted twice with ethyl acetate. The combined organic phases were washed with saturated aqueous sodium chloride solution, dried (sodium sulphate), filtered and concentrated under reduced pressure. The residue was purified by means of flash chromatography (silica gel 50, cyclohexane/ethyl acetate mixture). Yield: 4.84 g (89% purity, 74% of theory based on both batches)

LC/MS [Method 1]: $R_t$=1.29 min; MS (ESIpos): m/z=619 (M+H)⁺.

Example 9.1F

2-[4-{2-[(1-Aminocyclopropyl)methyl]-5-chlorophenyl}-5-(ethoxycarbonyl)-2-oxopyridin-1(2H)-yl]-4-methoxybutanoic acid (Stereoisomer Mixture)

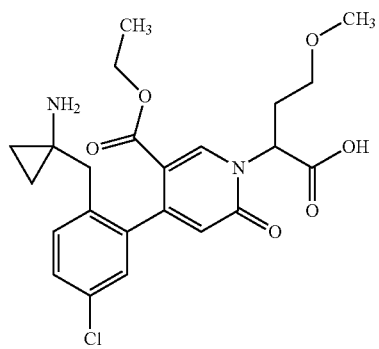 [SMILES: CCOC(=O)c1cn(C(CCOC)C(=O)O)c(=O)cc1-c1cc(Cl)ccc1CC1(N)CC1]

To a solution of 4.84 g (89% purity, 7.0 mmol) of ethyl 4-[2-({1-[(tert-butoxycarbonyl)amino]cyclopropyl}methyl)-5-chlorophenyl]-1-(1-tert-butoxy-4-methoxy-1-oxobutan-2-yl)-6-oxo-1,6-dihydropyridine-3-carboxylate (stereoisomer mixture) in 50 ml of dichloromethane were added under argon, while cooling with an ice bath, 10.7 ml (139 mmol, 20 eq.) of trifluoroacetic acid, and the mixture was stirred for 5 min, allowed to come to RT, stirred at RT for 6.5 h and then concentrated under reduced pressure. The residue was co-evaporated twice with toluene and once with dichloromethane, dried under high vacuum and converted without further purification. Yield: 4.45 g (80% purity, quant.)

LC/MS [Method 1]: $R_t$=0.62 min; MS (ESIpos): m/z=463 (M+H)⁺.

Example 9.1G 2-(11'-Chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (Stereoisomer Mixture)

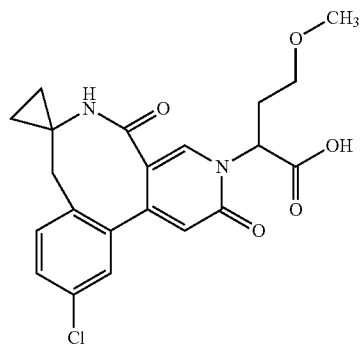 [SMILES: COCCC(C(=O)O)n1cc2c(cc1=O)-c1cc(Cl)ccc1CC1(CC1)NC2=O]

A solution of 4.37 g (80% purity, 7.6 mmol) of 2-[4-{2-[(1-aminocyclopropyl)methyl]-5-chlorophenyl}-5-(ethoxycarbonyl)-2-oxopyridin-1(2H)-yl]-4-methoxybutanoic acid (stereoisomer mixture) in 100 ml of tetrahydrofuran was added under argon to about 15 g of activated 3 Å molecular sieve (dried at 200° C. in a drying cabinet overnight) and stirred at RT for 2 h. Subsequently, the reaction mixture was admixed under argon at RT with 45 ml (151 mmol, 20 eq.) of a sodium ethoxide solution (21% in ethanol, dried beforehand over about 15 g of activated 3 Å molecular sieve for 2 h) and stirred at RT for 75 min. After dilution with ethyl acetate, the reaction mixture was decanted off from the molecular sieve, admixed with saturated aqueous ammonium chloride solution and then brought to pH 3 with aqueous hydrochloric acid solution (1 N). After phase separation, the aqueous phase was extracted three times with ethyl acetate. The combined organic phases were dried (sodium sulphate), filtered and concentrated under reduced pressure. The residue was purified by means of flash chromatography (silica gel 50, dichloromethane/methanol mixture). Yield: 1.05 g (33% of theory)

LC/MS [Method 1]: $R_t$=0.73 min; MS (ESIpos): m/z=417 (M+H)$^+$, $^1$H-NMR (400 MHz, DMSO-d$_6$): δ [ppm]=13.17-12.98 (m, 1H), 8.07/8.05 (2×s, 1H), 7.74/7.70 (2×s, 1H), 7.48-7.42 (m, 1H), 7.34-7.25 (m, 2H), 6.28 (s, 1H), 5.32/5.20 (2×t, 1H), 3.42-3.34 (m, 1H), 3.24-3.13 (m, 2H), 3.21/3.19 (2×s, 3H), 2.70 (dd, 1H), 2.41-2.30 (m, 2H), 1.01-0.92 (m, 1H), 0.80-0.72 (m, 1H), 0.72-0.63 (m, 2H).

Example 9.1H tert-Butyl 4-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}benzoate (Stereoisomer Mixture)

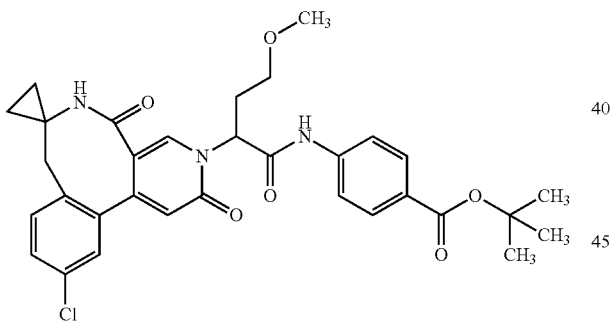

According to General Method 2A, 30 mg (71 µmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 18 mg (93 µmol, 1.3 eq.) of tert-butyl 4-aminobenzoate. After aqueous work-up, the crude product was purified by preparative RP-HPLC (Reprosil C18, water/acetonitrile gradient). Yield: 21 mg (49% of theory)

LC/MS [Method 1]: $R_t$=1.11 min; MS (ESIpos): m/z=592 (M+H)$^+$, $^1$H-NMR (400 MHz, DMSO-d$_6$): δ [ppm]=10.83/10.76 (2×s, 1H), 8.14/8.08 (2×s, 1H), 7.90-7.70 (2×m, 5H), 7.48-7.43 (m, 1H), 7.31 (d, 1H), 7.30-7.26 (m, 1H), 6.31 (s, 1H), 5.87/5.76 (t/dd, 1H), 3.45-3.36 (m, 1H), 3.3-3.15 (m, 2H), 3.23/3.20 (2×s, 3H), 2.75-2.63 (dd, 1H), 2.46-2.28 (m, 2H), 1.53 (s, 9H), 1.04-0.93 (m, 1H), 0.82-0.72 (m, 2H), 0.72-0.63 (m, 1H).

Example 9.2A tert-Butyl 6-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}-2-methyl-3-oxo-2,3-dihydro-1H-indazole-1-carboxylate (Stereoisomer Mixture)

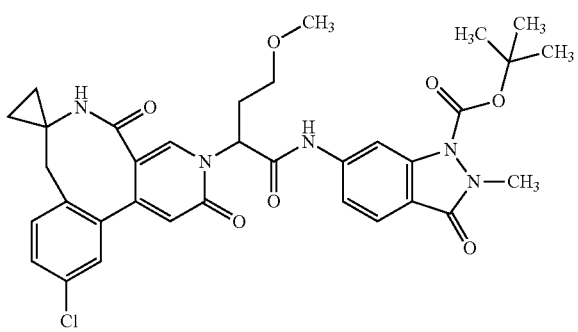 [SMILES: COCCC(C(=O)Nc1ccc2c(=O)n(C)n(C(=O)OC(C)(C)C)c2c1)n1cc2c(cc1=O)-c1cc(Cl)ccc1CC1(CC1)NC2=O]

According to General Method 1A, 70 mg (168 µmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 51 mg (185 µmol, 1.1 eq.) of tert-butyl 6-amino-2-methyl-3-oxo-2,3-dihydro-1H-indazole-1-carboxylate. After aqueous work-up, the crude product was purified by preparative RP-HPLC (Reprosil C18, water/acetonitrile gradient). Yield: 81 mg (73% of theory)

LC/MS [Method 1]: $R_t$=0.95 min; MS (ESIpos): m/z=662 (M+H)$^+$.

Example 9.3A

Methyl 5-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}pyridine-2-carboxylate (Stereoisomer Mixture)

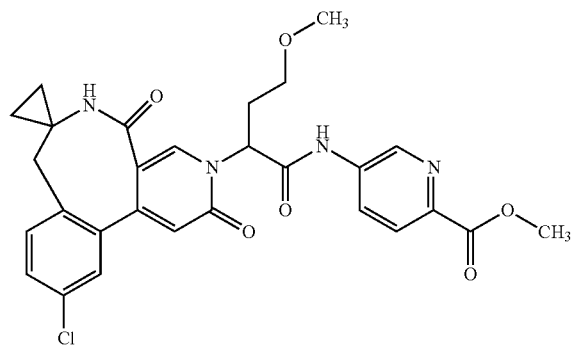 [SMILES: COCCC(C(=O)Nc1ccc(C(=O)OC)nc1)n1cc2c(cc1=O)-c1cc(Cl)ccc1CC1(CC1)NC2=O]

According to General Method 3A, 125 mg (300 µmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 50 mg (330 µmol, 1.1 eq.) of methyl 5-aminopyridine-2-carboxylate. Pyridine was removed under reduced pressure. The residue was stirred with water, and the resultant precipitate was filtered, washed with water and dried under high vacuum. Yield: 135 mg (89% purity, 73% of theory)

LC/MS [Method 1]: $R_t$=0.80 min; MS (ESIpos): m/z=551 (M+H)$^+$.

Example 9.4A

Methyl 5-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}thiophene-2-carboxylate (Stereoisomer Mixture)

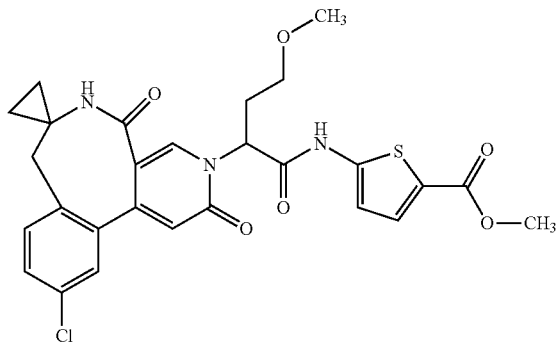 [SMILES: COCCC(C(=O)Nc1ccc(C(=O)OC)s1)n1cc2c(cc1=O)-c1cc(Cl)ccc1CC1(CC1)NC2=O]

According to General Method 1A, 83 mg (200 μmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 36 mg (220 μmol, 1.1 eq.) of methyl 5-aminothiophene-2-carboxylate. The reaction mixture was concentrated under reduced pressure. The residue was stirred with water, and the resultant precipitate was filtered, washed with water and dried under high vacuum. The precipitate was purified further by means of preparative RP-HPLC (Reprosil C18, water/acetonitrile gradient). Yield: 66 mg (58% of theory)

LC/MS [Method 1]: $R_t$=0.88 min; MS (ESIpos): m/z=556 (M+H)$^+$.

Example 9.5A

Methyl 5-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}thiophene-3-carboxylate (Stereoisomer Mixture)

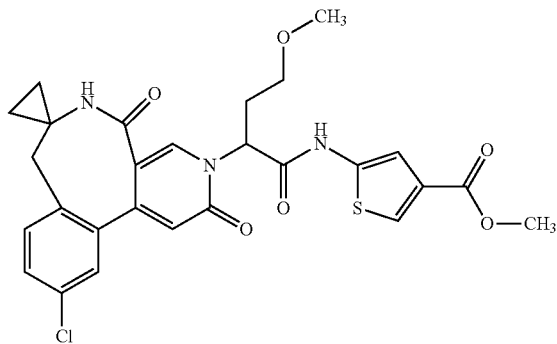 [SMILES: COCCC(C(=O)Nc1cc(C(=O)OC)cs1)n1cc2c(cc1=O)-c1cc(Cl)ccc1CC1(CC1)NC2=O]

According to General Method 1A, 83 mg (200 μmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 36 mg (220 μmol, 1.1 eq.) of methyl 5-aminothiophene-3-carboxylate. The reaction mixture was concentrated under reduced pressure. The residue was stirred with water, and the resultant precipitate was filtered, washed with water and dried under high vacuum. Yield: 116 mg (quant.).

LC/MS [Method 1]: $R_t$=0.88 min; MS (ESIpos): m/z=556 (M+H)$^+$.

Example 9.6A

Methyl 4-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}thiophene-2-carboxylate (Stereoisomer Mixture)

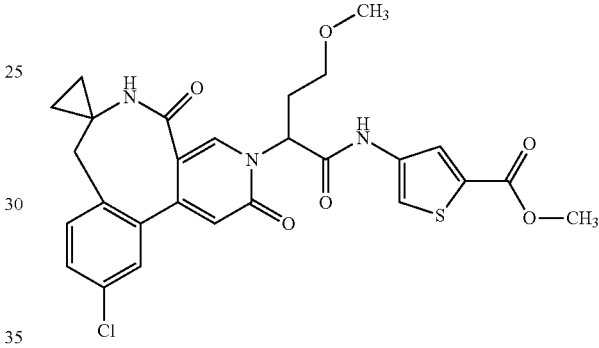

According to General Method 1A, 80 mg (192 μmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 33 mg (211 μmol, 1.1 eq.) of methyl 4-aminothiophene-2-carboxylate. The reaction mixture was concentrated under reduced pressure. The residue was stirred with water, and the resultant precipitate was filtered, washed with water and dried under high vacuum. The precipitate was purified further by means of preparative RP-HPLC (Reprosil C18, water/acetonitrile gradient). Yield: 83 mg (78% of theory)

LC/MS [Method 1]: $R_t$=0.93 min; MS (ESIpos): m/z=556 (M+H)$^+$.

Example 10.1A

Methyl trans-4-hydroxycyclohexanecarboxylate

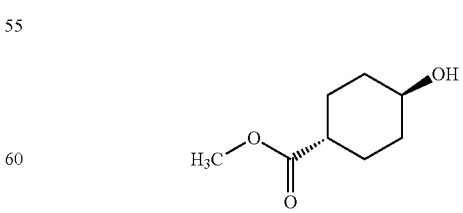

To a solution of 25.0 g (165 mmol, 95% purity) of trans-4-hydroxycyclohexanecarboxylic acid in 207 ml of methanol were added, at RT, 11.4 ml of sulphuric acid, and the resulting reaction solution was heated under reflux overnight. Subsequently, the mixture was neutralized with saturated aqueous sodium hydrogencarbonate solution and extracted three times with 250 ml of ethyl acetate. The combined organic phases were dried over magnesium sulphate and filtered, and the solvent was removed under reduced pressure. 25.5 g (97% of theory) of the title compound were obtained.

GC/MS [Method 9]: $R_t$=3.86 min; MS: m/z=158 (M)$^+$,
$^1$H-NMR (400 MHz, DMSO-d$_6$): δ [ppm]=4.55 (d, 1H), 3.57 (s, 3H), 3.39-3.30 (m, 1H), 2.25-2.16 (m, 1H), 1.89-1.77 (m, 4H), 1.40-1.27 (m, 2H), 1.21-1.08 (m, 2H).

Example 10.1B

Methyl trans-4-methoxycyclohexanecarboxylate

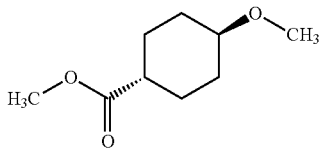

To a solution of 24.6 g (149 mmol) of methyl trans-4-hydroxycyclohexanecarboxylate in 1525 ml of dichloromethane were added, at 0° C. (ice bath), 35.2 g (164 mmol) of N,N,N',N'-tetramethylnaphthalene-1,8-diamine and the mixture was stirred at RT for 30 min. Subsequently, the mixture was cooled again to 0° C. (ice bath) and 30.0 g (203 mmol) of trimethyloxonium tetrafluoroborate were added. The mixture was stirred at RT overnight. Owing to incomplete reactions, the mixture was cooled to 0° C. (ice bath) and 30.0 g (203 mmol) of trimethyloxonium tetrafluoroborate were added to the reaction mixture, which was stirred at RT for a further 24 h. The reaction was ended by adding 1845 ml of water, 1100 ml of dichloromethane were added, and the phases were separated. The aqueous phase was extracted three times with dichloromethane, the combined organic phases were dried over magnesium sulphate and filtered and the solvent was removed under reduced pressure. The residue was purified by means of flash chromatography (cyclohexane-ethyl acetate gradient), and 18.4 g (72% of theory) of the title compound were obtained.

GC/MS [Method 9]: $R_t$=3.54 min; MS: m/z=172 (M)$^+$,
$^1$H-NMR (400 MHz, DMSO-d$_6$): δ [ppm]=3.58 (s, 3H), 3.22 (s, 3H), 3.12-3.03 (m, 1H), 2.32-2.23 (m, 1H), 2.01-1.84 (m, 4H), 1.41-1.29 (m, 2H), 1.19-1.07 (m, 2H).

Example 10.1C (trans-4-Methoxycyclohexyl)methanol

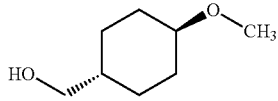

To 42.8 ml (103 mmol) of lithium aluminium hydride (2.4M in THF) in 307 ml of tert-butyl methyl ether was slowly added dropwise, at RT, a solution of 16.1 g (93.5 mmol) of methyl trans-4-methoxycyclohexanecarboxylate in 307 ml of tert-butyl methyl ether. On completion of addition, the mixture was heated to 40° C. and stirred for a further 6 h. The mixture was cooled to RT and the reaction was ended by adding 37.4 ml of water and 37.4 ml of 10% aqueous potassium hydroxide solution. The organic phase was decanted off, dried over sodium sulphate and filtered, and the solvent was removed under reduced pressure. 13.0 g (96% of theory) of the title compound were obtained.

GC/MS [Method 9]: $R_t$=3.09 min; MS: m/z=144 (M)$^+$,
$^1$H-NMR (400 MHz, DMSO-d$_6$): δ [ppm]=4.36 (t, 1H), 3.22 (s, 3H), 3.21-3.17 (m, 2H), 3.06-2.97 (m, 1H), 2.20-1.94 (m, 2H), 1.76-1.69 (m, 2H), 1.33-1.23 (m, 1H), 1.10-0.98 (m, 2H), 0.93-0.81 (m, 2H).

Example 10.1D (trans-4-Methoxycyclohexyl)methyl trifluoromethanesulphonate

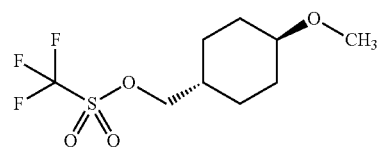 [SMILES: CO[C@H]1CC[C@H](COS(=O)(=O)C(F)(F)F)CC1]

2.30 g (15.9 mmol) of (trans-4-methoxycyclohexyl)methanol were initially charged in 32 ml of dichloromethane, and 2.79 ml (23.9 mmol) of 2,6-dimethylpyridine and 4.05 ml (23.9 mmol) of trifluoromethanesulphonic anhydride were added successively at 0° C. (ice bath). The mixture was stirred at 0° C. for 1 h. The reaction was diluted with 300 ml of diethyl ether and washed four times with 100 ml of a mixture of 1 N aqueous hydrochloric acid and saturated aqueous sodium chloride solution (1:3). The organic phase was finally washed with saturated aqueous sodium hydrogencarbonate solution, dried over sodium sulphate and filtered, and the solvent was removed under reduced pressure. 2.49 g (17% of theory, 30% purity) of the title compound were obtained.

GC/MS [Method 9]: $R_t$=3.76 min; MS: m/z=276 (M)$^+$.

Example 10.1E

N-(Diphenylmethylidene)-3-(trans-4-methoxycyclohexyl)alanine tert-butyl ester (Racemate)

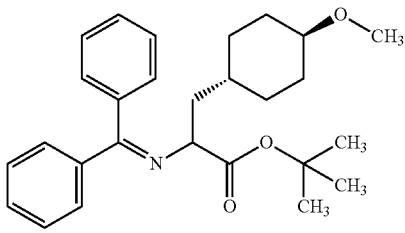 [SMILES: CO[C@H]1CC[C@H](CC(N=C(c2ccccc2)c2ccccc2)C(=O)OC(C)(C)C)CC1]

To a solution of 1.42 g (4.81 mmol) of tert-butyl N-(diphenylmethylene)glycinate in 40 ml of tetrahydrofuran were added dropwise, under argon at −78° C., 11.1 ml (1.0 M in THF, 11.1 mmol, 2.3 eq.) of lithium bis(trimethylsilyl) amide, the mixture was stirred for 15 min, and then 2.85 g (70% purity, 7.21 mmol, 1.5 eq.) of (trans-4-methoxycyclohexyl)methyl trifluoromethanesulphonate were added dropwise. The reaction mixture was stirred at −78° C. for a further 15 min, allowed to come to RT, stirred overnight and then quenched with 50 ml of water. After addition of ethyl acetate and phase separation, the aqueous phase was extracted twice with ethyl acetate. The combined organic phases were washed with saturated aqueous sodium chloride solution and concentrated under reduced pressure. The residue was purified by means of flash chromatography (silica gel 50, cyclohexane/ethyl acetate mixture). 0.54 g (18% of theory, 68% purity) of the title compound were obtained.

LC/MS [Method 1]: $R_t$=1.36 min; MS (ESIpos): m/z=422 (M+H)$^+$.

Example 10.1F 3-(trans-4-Methoxycyclohexyl)alanine tert-butyl ester (Racemate)

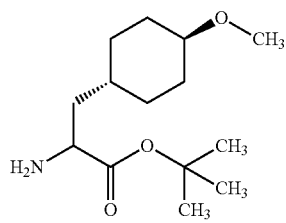

To a solution of 1.70 g (70% purity, 2.82 mmol) of N-(diphenylmethylidene)-3-(trans-4-methoxycyclohexyl) alanine tert-butyl ester (racemate) in tetrahydrofuran were added 50 ml of an aqueous citric acid solution (1M), and the mixture was stirred at RT for 90 min. Subsequently, tetrahydrofuran was removed under reduced pressure. The resulting aqueous solution was neutralized cautiously with solid sodium bicarbonate and extracted twice with dichloromethane. The combined organic phases were dried (sodium sulphate), filtered and concentrated on a rotary evaporator under reduced pressure (>150 mbar at water bath temperature <25° C.). The residue was purified by means of flash chromatography (silica gel 50, dichloromethane/methanol mixture). 739 mg (quant.) of the title compound were obtained.

GC/MS [Method 9]: $R_t$=5.50 min; MS: m/z=157 (M-CO$_2$tBu)$^+$, $^1$H-NMR (400 MHz, DMSO-d$_6$): δ [ppm]=3.21 (s, 3H), 3.20-3.13 (m, 1H), 3.08-2.99 (m, 1H), 2.02-1.92 (m, 2H), 1.77-1.68 (m, 2H), 1.62 (br. s, 2H), 1.42-1.21 (m, 3H), 1.41 (s, 9H), 1.10-0.78 (m, 4H).

Example 10.1G

Ethyl 1-[1-tert-butoxy-3-(trans-4-methoxycyclohexyl)-1-oxopropan-2-yl]-4-hydroxy-6-oxo-1,6-dihydropyridine-3-carboxylate (Racemate)

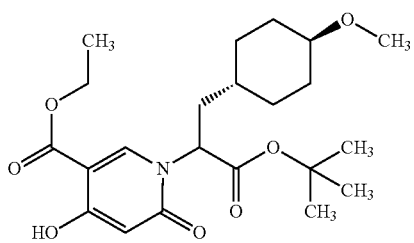 [SMILES: CCOC(=O)c1cn(C(C[C@H]2CC[C@H](OC)CC2)C(=O)OC(C)(C)C)c(=O)cc1O]

189 μl (1.04 mmol) of diethyl 3-oxopentanedicarboxylate and 239 μl (1.46 mmol, 1.4 eq.) of diethoxymethyl acetate were stirred at 100° C. for 2.5 h, and the mixture was cooled to RT, then co-evaporated three times with toluene and dried under high vacuum. The residue was taken up in 1 ml of ethanol, a solution of 282 mg (1.10 mmol, 1.05 eq.) of 3-(trans-4-methoxycyclohexyl)alanine tert-butyl ester (racemate) in 1 ml of ethanol was added while cooling with ice and the mixture was stirred at RT for 1 h. Subsequently, the reaction mixture was admixed with 390 μl (1.04 mmol, 1.0 eq.) of a sodium ethoxide solution (21% in ethanol, dried beforehand over about 15 g of activated 3 Å molecular sieve for 2 h), stirred at RT for 1 h and quenched with saturated aqueous ammonium chloride solution. After phase separation, the aqueous phase was extracted three times with ethyl acetate. The combined organic phases were dried (magnesium sulphate), filtered and concentrated under reduced pressure. The residue was purified by means of flash chromatography (silica gel 50, cyclohexane/ethyl acetate mixture). 150 mg (34% of theory) of the title compound were obtained.

LC/MS [Method 1]: $R_t$=1.05 min; MS (ESIpos): m/z=424 (M+H)$^+$, $^1$H-NMR (400 MHz, DMSO-d$_6$): δ [ppm]=10.89 (s, 1H), 8.31 (s, 1H), 5.70 (s, 1H), 5.26-5.18 (m, 1H), 4.32-4.26 (m, 2H), 3.19 (s, 3H), 3.06-2.97 (m, 1H), 2.00-1.75 (m, 5H), 1.65-1.57 (m, 1H), 1.37 (s, 9H), 1.29 (t, 3H), 1.05-0.83 (m, 5H).

Example 10.1H

Ethyl 1-[1-tert-butoxy-3-(trans-4-methoxycyclohexyl)-1-oxopropan-2-yl]-6-oxo-4-{[(trifluoromethyl)sulphonyl]oxy}-1,6-dihydropyridine-3-carboxylate (Racemate)

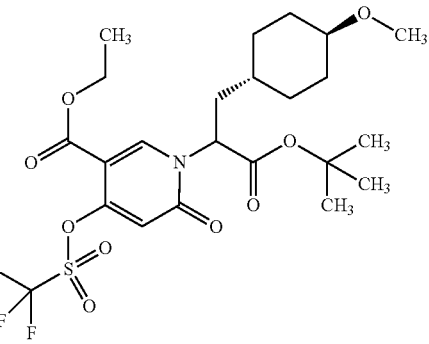

To a solution of 274 mg (647 μmol) of ethyl 1-[1-tert-butoxy-3-(trans-4-methoxycyclohexyl)-1-oxopropan-2-yl]-4-hydroxy-6-oxo-1,6-dihydropyridine-3-carboxylate (racemate) in 5 ml of dichloromethane were added, under argon at −78° C., 180 μl (1.29 mmol, 2.0 eq.) of triethylamine and then, in portions, 321 mg (776 μmol, 1.2 eq.) of N-(4-tert-butylphenyl)-1,1,1-trifluoro-N-[(trifluoromethyl)sulphonyl] methanesulphonamide. The reaction mixture was allowed to come to RT, stirred at RT overnight and then concentrated under reduced pressure. The residue was purified by means of flash chromatography (silica gel 50, cyclohexane/ethyl acetate mixture). 298 mg (82% of theory) of the title compound were obtained.

LC/MS [Method 1]: $R_t$=1.27 min; MS (ESIpos): m/z=556 (M+H)⁺,

¹H-NMR (400 MHz, DMSO-d₆): δ [ppm]=8.65 (s, 1H), 6.68 (s, 1H), 5.30-5.23 (m, 1H), 4.32 (q, 2H), 3.20 (s, 3H), 3.07-2.97 (m, 1H), 2.01-1.90 (m, 4H), 1.84-1.76 (m, 1H), 1.67-1.59 (m, 1H), 1.37 (s, 9H), 1.30 (t, 3H), 1.12-0.88 (m, 5H).

Example 10.1I

Ethyl 4-[(2-{1-[(tert-butoxycarbonyl)amino]cyclopropyl}methyl)-5-chlorophenyl]-1-[1-tert-butoxy-3-(trans-4-methoxycyclohexyl)-1-oxopropan-2-yl]-6-oxo-1,6-dihydropyridine-3-carboxylate (Stereoisomer Mixture)

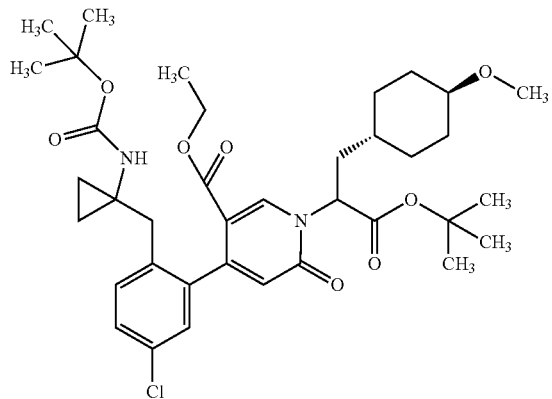 [SMILES: CCOC(=O)c1cn(C(C[C@H]2CC[C@H](OC)CC2)C(=O)OC(C)(C)C)c(=O)cc1-c1cc(Cl)ccc1CC1(NC(=O)OC(C)(C)C)CC1]

A mixture of 292 g (520 μmol) of ethyl 1-[1-tert-butoxy-3-(trans-4-methoxycyclohexyl)-1-oxopropan-2-yl]-6-oxo-4-{[(trifluoromethyl)sulphonyl]oxy}-1,6-dihydropyridine-3-carboxylate (racemate), 209 mg (520 μmol) of [2-({1-[(tert-butoxycarbonyl)amino]cyclopropyl}methyl)-5-chlorophenyl]boric acid and 216 mg (1.56 mmol, 3.0 eq.) of potassium carbonate was dried under high vacuum, placed under argon, 8 ml of dioxane were added and argon was passed through the mixture for 10 min. Subsequently, 42 mg (52 μmol, 0.1 eq.) of [1,1-bis-(diphenylphosphino)ferrocene]palladium(II) chloride-monodichloromethane adduct were added to the reaction mixture, which was stirred at oil bath temperature 80° C. for 1 h. After cooling to RT, the reaction mixture was filtered through Celite. After washing with dioxane, the combined filtrates were concentrated under reduced pressure. The residue was taken up in water and extracted twice with ethyl acetate. The combined organic phases were washed with saturated aqueous sodium chloride solution, dried (magnesium sulphate), filtered and concentrated under reduced pressure. The residue was purified by means of flash chromatography (silica gel 50, cyclohexane/ethyl acetate mixture). 286 mg (79% of theory) of the title compound were obtained.

LC/MS [Method 1]: $R_t$=1.41 min; MS (ESIpos): m/z=687 (M+H)⁺.

Example 10.1J

2-[4-{2-[(1-Aminocyclopropyl)methyl]-5-chlorophenyl}-5-(ethoxycarbonyl)-2-oxopyridin-1(2H)-yl]-3-(trans-4-methoxycyclohexyl)propanoic acid (Stereoisomer Mixture)

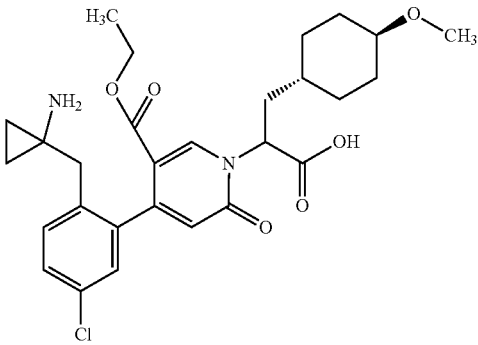 [SMILES: CCOC(=O)c1cn(C(C[C@H]2CC[C@H](OC)CC2)C(=O)O)c(=O)cc1-c1cc(Cl)ccc1CC1(N)CC1]

To a solution of 286 mg (412 μmol) of ethyl 4-[2-{1-[(tert-butoxycarbonyl)amino]cyclopropyl}methyl)-5-chlorophenyl]-1-[1-ter-butoxy-3-(trans-4-methoxycyclohexyl)-1-oxopropan-2-yl]-6-oxo-1,6-dihydropyridine-3-carboxylate (stereoisomer mixture) in 4 ml of dichloromethane were added, under argon, 635 μl (8.24 mmol, 20 eq.) of trifluoroacetic acid, and the mixture was stirred at RT overnight. Conversion was incomplete; a further 159 μl (206 mmol, 5 eq.) of trifluoroacetic acid were added and the mixture, after a further 12 h at RT, was concentrated under reduced pressure. The residue was co-evaporated repeatedly with toluene, dried under high vacuum and converted without further purification. 320 mg (quant.) of the title compound were obtained.

LC/MS [Method 1]: $R_t$=0.76 min; MS (ESIpos): m/z=531 (M+H)⁺.

Example 10.1K 2-(11'-Chloro-2',5'-dioxo-2',5',6',8'-tetrahydro-3'H-spiro[cyclopropane-1,7'-pyrido[3,4-e][3]benzazocine]-3'-yl)-3-(trans-4-methoxycyclohexyl)propanoic acid (Stereoisomer Mixture)

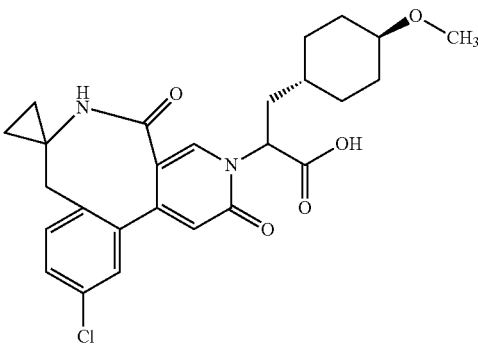 [SMILES: CO[C@H]1CC[C@H](CC(C(=O)O)n2cc3c(cc2=O)-c2cc(Cl)ccc2CC2(CC2)NC3=O)CC1]

A solution of 219 mg (412 μmol) of 2-[4-(2-[(1-aminocyclopropyl)methyl]-5-chlorophenyl)-5-(ethoxycarbonyl)-2-oxopyridin-1(2H)-yl]-3-(trans-4-methoxycyclohexyl)propanoic acid (stereoisomer mixture) in 5 ml of tetrahydrofuran was added under argon to activated 3 Å molecular sieve (dried at 200° C. in a drying cabinet overnight) and stirred at RT for 2 h. Subsequently, the reaction mixture was admixed under argon at RT with 3.1 ml (8.2 mmol, 20 eq.) of a sodium ethoxide solution (21% in ethanol, dried beforehand over about 15 g of activated 3 Å molecular sieve for 2 h) and stirred at RT for 60 min. After dilution with ethyl acetate, the reaction mixture was admixed with saturated aqueous ammonium chloride solution and then brought to pH 3 with aqueous hydrochloric acid solution (1 N). After phase separation, the aqueous phase was extracted three times with ethyl acetate. The combined organic phases were washed twice with 0.5 N aqueous hydrochloric acid and with 20 ml of saturated aqueous sodium chloride solution, dried (magnesium sulphate), filtered and concentrated under reduced pressure. 132 mg (66% of theory) of the title compound were obtained.

LC/MS [Method 1]: $R_t$=0.83I0.84 min; MS (ESIpos): m/z=485 (M+H)$^+$.

$^1$H-NMR (400 MHz, DMSO-d$_6$): δ [ppm]=13.25/13.05 (2×s, 1H), 8.10/8.09 (2×s, 1H), 7.77 (d, 1H), 7.45 (dd, 1H), 7.33-7.27 (m, 2H), 6.32/6.29 (2×s, 1H), 5.57-5.50/5.26-5.18 (2×m, 1H), 3.23-3.15 (m, 1H), 3.21/3.19 (2×s, 3H), 3.08-2.97 (m, 1H), 2.73-2.65 (m, 1H), 2.28-2.15 (m, 1H), 2.02-1.54 (m, 5H), 1.08-0.61 (m, 9H).

Example 10.1L

Ethyl 4-{[2-(11'-chloro-2',5'-dioxo-2',5',6',8'-tetrahydro-3'H-spiro[cyclopropane-1,7'-pyrido[3,4-e][3]benzazocine]-3'-yl)-3-(trans-4-methoxycyclohexyl)propanoyl]amino}benzoate (Stereoisomer Mixture)

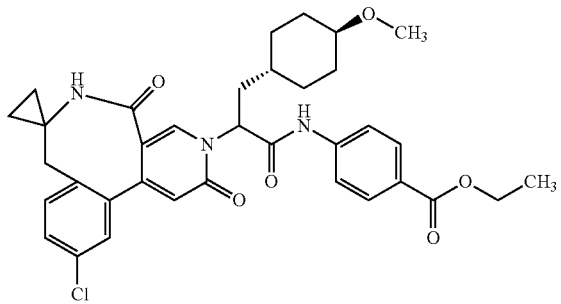 [SMILES: CCOC(=O)c1ccc(NC(=O)C(C[C@H]2CC[C@H](OC)CC2)n2cc3c(cc2=O)-c2cc(Cl)ccc2CC2(CC2)NC3=O)cc1]

A solution of 50.0 mg (103 μmol) of 2-(11'-chloro-2',5'-dioxo-2',5',6',8'-tetrahydro-3'H-spiro[cyclopropane-1,7'-pyrido[3,4-e][3]benzazocine]-3'-yl)-3-(trans-4-methoxycyclohexyl)propanoic acid (stereoisomer mixture), 17.0 mg (103 μmol, 1.0 eq.) of ethyl 4-aminobenzoate, 10 mg (72 μmol) of Oxyma and 16.1 μl (103 μmol) of N,N'-diisopropylcarbodiimide in DMF was stirred at 40° C. overnight. Subsequently, the solvent was removed under reduced pressure and the residue was purified by means of preparative HPLC [column: Chromatorex C18, 10 μm, 125 mm×30 mm, eluent: acetonitrile/0.1% formic acid gradient (0 to 3 min 10% acetonitrile, to 35 min 90% acetonitrile and for a further 3 min 90% acetonitrile)]. 42.8 mg (66% of theory) of the title compound were obtained.

LC/MS [Method 1]: $R_t$=1.09 min; MS (ESIpos): m/z=632 (M+H)$^+$, $^1$H-NMR (400 MHz, DMSO-d$_6$): δ [ppm]=10.88/10.82 (2×s, 1H), 8.16/8.10 (2×s, 1H), 7.97-7.68 (m, 5H), 7.48-7.42 (m, 1H), 7.33-7.27 (m, 2H), 6.33/6.32 (2×s, 1H), 5.93/5.83 (2×dd, 1H), 4.29 (q, 2H), 3.25-3.15 (m, 1H), 3.22/3.20 (2×s, 3H), 3.09-2.99 (m, 1H), 2.74-2.61 (m, 1H), 2.34-1.70 (m, 6H), 1.31 (t, 3H), 1.16-0.61 (m, 9H).

Example 11.1A

Ethyl 1-(1-tert-butoxy-1-oxo-3-phenylpropan-2-yl)-4-hydroxy-6-oxo-1,6-dihydropyridine-3-carboxylate (Racemate)

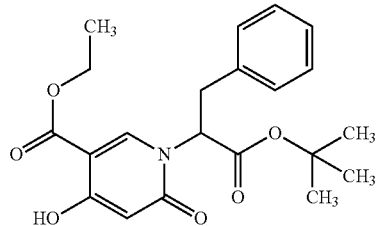 [SMILES: CCOC(=O)c1cn(C(Cc2ccccc2)C(=O)OC(C)(C)C)c(=O)cc1O]

2.1 ml (11.1 mmol) of diethyl 3-oxopentanedicarboxylate and 2.6 ml (15.5 mmol, 1.4 eq.) of diethoxymethyl acetate were stirred at 100° C. for 2.5 h, and the mixture was cooled to RT, then co-evaporated three times with toluene and dried under high vacuum. The residue was taken up in 80 ml of ethanol, 3.0 g (11.6 mmol, 1.05 eq.) of tert-butyl L-phenylalaninate hydrochloride (in 20 ml of ethanol and 1.93 ml of N,N-diisopropylethylamine) were added while cooling with ice and the mixture was stirred at RT for 1 h. Subsequently, the reaction mixture was admixed in portions with a total of 10.4 ml (27.7 mmol, 2.5 eq.) of a sodium ethoxide solution (21% in ethanol, dried beforehand over about 15 g of activated 3 Å molecular sieve for 2 h) and stirred at RT until conversion was virtually complete. Subsequently, the reaction mixture was quenched with saturated aqueous ammonium chloride solution. The solid that precipitates out was filtered, washed with ethyl acetate and discarded. After phase separation of the combined filtrates, the aqueous phase was extracted three times with ethyl acetate. The combined organic phases were washed with saturated aqueous sodium chloride solution, dried (sodium sulphate), filtered and concentrated under reduced pressure. The residue was purified by means of flash chromatography (silica gel 50, cyclohexane/ethyl acetate mixture). Yield: 3.2 g (90% purity, 67% of theory).

LC/MS [Method 1]: $R_t$=1.15 min; MS (ESIneg): m/z=388 (M+H)$^+$.

Example 11.1B

Ethyl 1-(1-tert-butoxy-1-oxo-3-phenylpropan-2-yl)-6-oxo-4-{[(trifluoromethyl)sulphonyl]oxy}-1,6-dihydropyridine-3-carboxylate (Racemate)

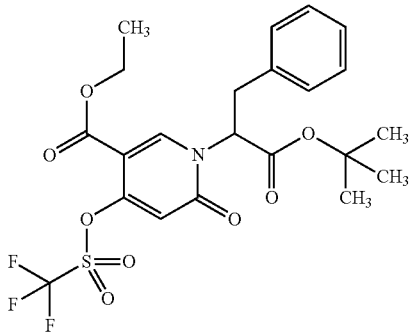 [SMILES: CCOC(=O)c1cn(C(Cc2ccccc2)C(=O)OC(C)(C)C)c(=O)cc1OS(=O)(=O)C(F)(F)F]

To a solution of 1.00 g (2.19 mmol) of ethyl 1-(1-tert-butoxy-1-oxo-3-phenylpropan-2-yl)-4-hydroxy-6-oxo-1,6-dihydropyridine-3-carboxylate (racemate) in 17 ml of dichloromethane were added, under argon at −78° C., 0.61 ml (4.39 mmol, 2.0 eq.) of triethylamine and then, in portions, 1.45 g (3.51 mmol, 1.6 eq.) of N-(4-tert-butylphenyl)-1,1,1-trifluoro-N-[(trifluoromethyl)sulphonyl]methanesulphonamide. The reaction mixture was allowed to come to RT, stirred at RT overnight and then concentrated under reduced pressure. The residue was purified by means of flash chromatography (silica gel 50, cyclohexane/ethyl acetate mixture). Yield: 554 mg (89% purity, 43% of theory)

LC/MS [Method 1]: $R_t$=1.30 min; MS (ESIpos): m/z=520 (M+H)$^+$.

Example 11.1C

Ethyl 4-[(2-{1-[(tert-butoxycarbonyl)amino]cyclopropyl}methyl)-5-chlorophenyl]-1-(1-tert-butoxy-1-oxo-3-phenylpropan-2-yl)-6-oxo-1,6-dihydropyridine-3-carboxylate (Stereoisomer Mixture)

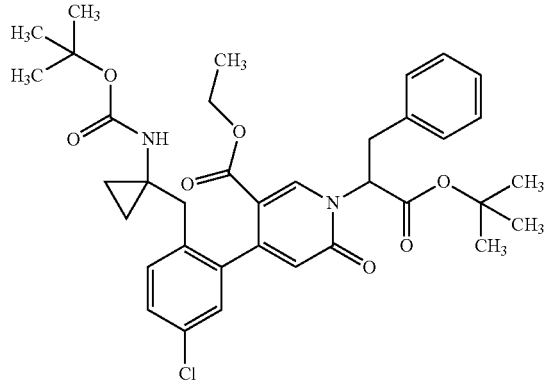 [SMILES: CCOC(=O)c1cn(C(Cc2ccccc2)C(=O)OC(C)(C)C)c(=O)cc1-c1cc(Cl)ccc1CC1(NC(=O)OC(C)(C)C)CC1]

A mixture of 554 mg (89% purity, 0.95 mmol) of ethyl 1-(1-tert-butoxy-1-oxo-3-phenylpropan-2-yl)-6-oxo-4-{[(trifluoromethyl)sulphonyl]oxy}-1,6-dihydropyridine-3-carboxylate (racemate), 439 mg (1.09 mmol, 1.15 eq.) of [2-{(1-[(tert-butoxycarbonyl)amino]cyclopropyl}methyl)-5-chlorophenyl]boric acid and 394 mg (2.85 mmol, 3.0 eq.) of potassium carbonate was dried under high vacuum, placed under argon, 10 ml of dioxane were added and argon was passed through the mixture for 10 min. Subsequently, 78 mg (0.10 mmol, 0.1 eq.) of [1,1-bis-(diphenylphosphino)ferrocene]palladium(II) chloride monodichloromethane adduct were added to the reaction mixture, which was stirred at oil bath temperature 80° C. for 1 h. After cooling to RT, the reaction mixture was filtered through Celite. After washing with dioxane, the combined filtrates were concentrated under reduced pressure. The residue was taken up in water and extracted twice with ethyl acetate. The combined organic phases were washed with saturated aqueous sodium chloride solution, dried (sodium sulphate), filtered and concentrated under reduced pressure.

Analogously, a second batch was conducted with 2.96 g (88% purity, 5.01 mmol) of ethyl 1-(1-tert-butoxy-1-oxo-3-phenylpropan-2-yl)-6-oxo-4-{[(trifluoromethyl)sulphonyl]oxy}-1,6-dihydropyridine-3-carboxylate (racemate), and the two products were combined and purified by means of flash chromatography (silica gel 50, cyclohexane/ethyl acetate mixture). Yield: 3.41 g (81% purity, 71% of theory based on both batches)

LC/MS [Method 1]: $R_t$=1.41 min; MS (ESIpos): m/z=651 (M+H)$^+$.

Example 11.1D

2-[4-{2-[(1-Aminocyclopropyl)methyl]-5-chlorophenyl}-5-(ethoxycarbonyl)-2-oxopyridin-1(2H)-yl]-3-phenylpropanoic acid (Stereoisomer Mixture)

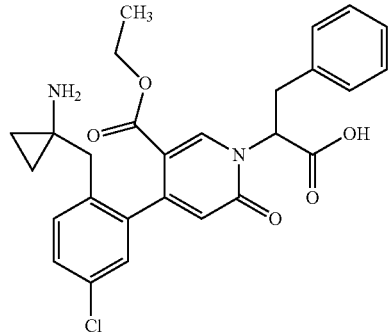 [SMILES: CCOC(=O)c1cn(C(Cc2ccccc2)C(=O)O)c(=O)cc1-c1cc(Cl)ccc1CC1(N)CC1]

To a solution of 3.41 g (assumed purity of 75%, 3.93 mmol) of ethyl 4-[2-{(1-[(tert-butoxycarbonyl)amino]cyclopropyl}methyl)-5-chlorophenyl]-1-(1-tert-butoxy-1-oxo-3-phenylpropan-2-yl)-6-oxo-1,6-dihydropyridine-3-carboxylate (stereoisomer mixture) in 40 ml of dichloromethane were added under argon, while cooling with an ice bath, 6.0 ml (78.5 mmol, 20 eq.) of trifluoroacetic acid, and the mixture was stirred for 5 min, allowed to come to RT, stirred at RT for 6 h and then concentrated under reduced pressure. Since the conversion was incomplete, the residue was dissolved once again in 40 ml of dichloromethane, 6.0 ml (78.5 mmol, 20 eq.) of trifluoroacetic acid were added dropwise under argon while cooling with an ice bath, and the mixture was stirred for 5 min, allowed to come to RT and stirred at RT for a further 6 h. Subsequently, the reaction mixture was concentrated under reduced pressure and the residue was co-evaporated twice with toluene, dried under high vacuum and converted without further purification. Yield: 3.36 g (70% purity, quant.)

LC/MS [Method 1]: $R_t$=0.79 min; MS (ESIpos): m/z=495 (M+H)$^+$.

Example 11.1E 2-(11'-Chloro-2',5'-dioxo-2',5',6',8'-tetrahydro-3'H-spiro[cyclopropane-1,7'-pyrido[3,4-e][3]benzazocine]-3'-yl)-3-phenylpropanoic acid (Stereoisomer Mixture)

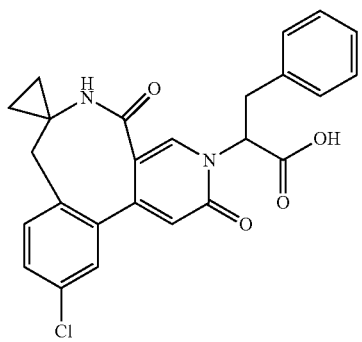 [SMILES: O=C1NC2(CC2)Cc2ccc(Cl)cc2-c2cc(=O)n(C(Cc3ccccc3)C(=O)O)cc21]

A solution of 1.5 g (70% purity, 2.1 mmol) of 2-[4-{2-[(1-aminocyclopropyl)methyl]-5-chlorophenyl}-5-(ethoxycarbonyl)-2-oxopyridin-1(2H)-yl]-3-phenylpropanoic acid (stereoisomer mixture) in 30 ml of tetrahydrofuran was added under argon to about 4 g of activated 3 Å molecular sieve (dried at 200° C. in a drying cabinet overnight) and stirred at RT for 2 h. Subsequently, the reaction mixture was admixed under argon at RT with 12.5 ml (42 mmol, 20 eq.) of a sodium ethoxide solution (21% in ethanol, dried beforehand over about 15 g of activated 3 Å molecular sieve for 2 h) and stirred at RT for 2 h. The reaction mixture was filtered, admixed with saturated aqueous ammonium chloride solution and then brought to pH 3 with aqueous hydrochloric acid solution (1 N). After phase separation, the aqueous phase was extracted twice with ethyl acetate. The combined organic phases were dried (sodium sulphate), filtered and concentrated under reduced pressure. The residue was converted without further purification. Yield: 643 mg (63% purity, 43% of theory)

LC/MS [Method 1]: $R_t$=0.86 min; MS (ESIpos): m/z=449 (M+H)$^+$.

Example 11.1F tert-Butyl 4-{[2-(11'-chloro-2',5'-dioxo-2',5',6',8'-tetrahydro-3'H-spiro[cyclopropane-1,7'-pyrido[3,4-e][3]benzazocine]-3'-yl)-3-phenylpropanoyl]amino}benzoate (Stereoisomer Mixture)

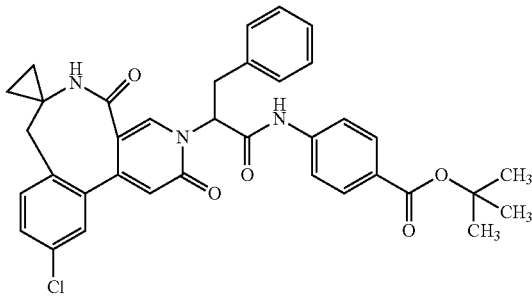 [SMILES: CC(C)(C)OC(=O)c1ccc(NC(=O)C(Cc2ccccc2)n2cc3c(cc2=O)-c2cc(Cl)ccc2CC2(CC2)NC3=O)cc1]

According to General Method 3A, 214 mg (63% purity, 0.30 mmol) of 2-(11'-chloro-2',5'-dioxo-2',5',6',8'-tetrahydro-3'H-spiro[cyclopropane-1,7'-pyrido[3,4-e][3]benzazocine]-3'-yl)-3-phenylpropanoic acid (stereoisomer mixture) were reacted with 87 mg (0.45 mmol, 1.5 eq.) of tert-butyl 4-aminobenzoate. After aqueous work-up, the crude product was purified by preparative RP-HPLC (Reprosil C18, water/acetonitrile gradient). Yield: 88 mg (47% of theory)

LC/MS [Method 1]: $R_t$=1.21 min; MS (ESIpos): m/z=624 (M+H)$^+$.

Example 12.1A

Ethyl 1-(1-tert-butoxy-4-methoxy-1-oxobutan-2-yl)-6-oxo-4-(4,4,5,5-tetramethyl-1,3,2-dioxaborolan-2-yl)-1,6-dihydropyridine-3-carboxylate (Racemate)

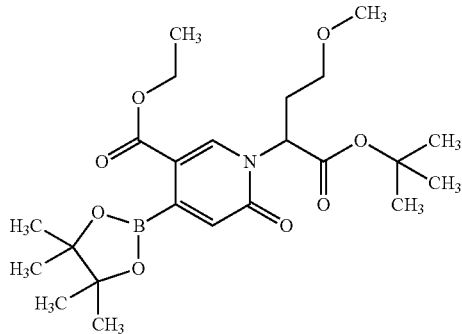 [SMILES: CCOC(=O)c1cn(C(CCOC)C(=O)OC(C)(C)C)c(=O)cc1B1OC(C)(C)C(C)(C)O1]

1.00 g (85% purity, 1.74 mmol) of ethyl 1-(1-tert-butoxy-4-methoxy-1-oxobutan-2-yl)-6-oxo-4-{[(trifluoromethyl)sulphonyl]oxy}-1,6-dihydropyridine-3-carboxylate (racemate), 487 mg (1.92 mmol, 1.1 eq.) of bis(pinacolato)diboron and 513 mg (5.23 mmol, 3 eq.) of potassium acetate were initially charged in 18 ml of dioxane under argon, 42.7 mg (0.05 mmol, 0.03 eq.) of [1,1-bis(diphenylphosphino)ferrocene]dichloropalladium monodichloromethane adduct were added and the mixture was stirred at 80° C. for 7 h. The reaction mixture was cooled to RT, filtered through kieselguhr and washed through with dioxane. The filtrate was concentrated and dried at 40° C. under high vacuum. Yield: 980 mg (80% purity, 97% of theory).

$^1$H-NMR (400 MHz, DMSO-d$_6$): δ [ppm]=8.31 (s, 1H), 6.39 (s, 1H), 5.12 (dd, 1H), 4.34-4.20 (m, 2H), 3.38-3.33 (m, 1H), 3.16-3.04 (m, 4H), 2.34-2.17 (m, 2H), 1.36 (s, 9H), 1.33-1.25 (m, 15H).

Example 12.1B

Ethyl 4-(2-{2-[(tert-butoxycarbonyl)amino]-3-fluoropropyl}-5-chlorophenyl)-1-(1-tert-butoxy-4-methoxy-1-oxobutan-2-yl)-6-oxo-1,6-dihydropyridine-3-carboxylate (Stereoisomer Mixture)

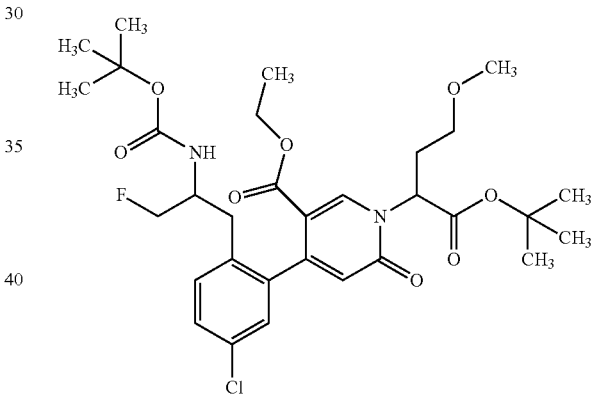

A mixture of 399 mg (75% purity, 0.82 mmol) of tert-butyl [1-(2-bromo-4-chlorophenyl)-3-fluoropropan-2-yl]carbamate (racemate), 950 mg (80% purity, 1.63 mmol, 2 eq.) of ethyl 1-(1-tert-butoxy-4-methoxy-1-oxobutan-2-yl)-6-oxo-4-(4,4,5,5-tetramethyl-1,3,2-dioxaborolan-2-yl)-1,6-dihydropyridine-3-carboxylate (racemate) and 677 mg (4.90 mmol, 6 eq.) of potassium carbonate were dried under high vacuum, the mixture was placed under argon, 18 ml of dioxane were added and argon was passed through the mixture for 5 min. Subsequently, 133 mg (0.16 mmol, 0.2 eq.) of [1,1-bis(diphenylphosphino)ferrocene]dichloropalladium monodichloromethane adduct were added to the reaction mixture, which was stirred at oil bath temperature 80° C. for 6 h. The reaction mixture was filtered through kieselguhr, washed with dichloromethane/acetonitrile, and the filtrate was concentrated. The crude product was purified by flash chromatography (silica cartridge, cyclohexane/ethyl acetate mixture). Yield: 380 mg (60% purity, 44% of theory)

LC/MS [Method 12]: $R_t$=2.44 min; MS (ESIpos): m/z=625 (M+H)$^+$.

Example 12.1C

2-{4-[2-(2-Amino-3-fluoropropyl)-5-chlorophenyl]-5-(ethoxycarbonyl)-2-oxopyridin-1(2H)-yl}-4-methoxybutanoic acid (Stereoisomer Mixture)

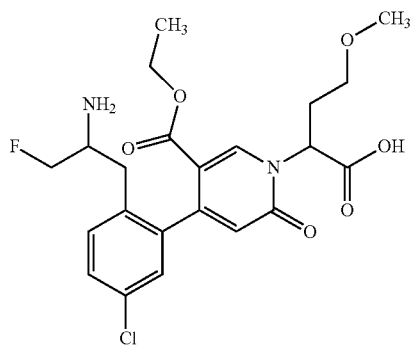 [SMILES: CCOC(=O)c1cn(C(CCOC)C(=O)O)c(=O)cc1-c1cc(Cl)ccc1CC(N)CF]

A solution of 380 mg (60% purity, 0.36 mmol) of ethyl 4-(2-{2-[(tert-butoxycarbonyl)amino]-3-fluoropropyl}-5-chlorophenyl)-1-(1-tert-butoxy-4-methoxy-1-oxobutan-2-yl)-6-oxo-1,6-dihydropyridine-3-carboxylate (stereoisomer mixture) in 10 ml of a solution of hydrogen chloride in dioxane (4M) was stirred at RT for 6 h. Subsequently, the reaction mixture was concentrated under reduced pressure. The crude product was purified by preparative HPLC (water/acetonitrile/0.1% formic acid gradient). Yield: 161 mg (90% purity, 85% of theory)

LC/MS [Method 11]: $R_t$=1.25 min; MS (ESIpos): m/z=469 (M+H)$^+$.

Example 12.1D

2-[11-Chloro-7-(fluoromethyl)-2,5-dioxo-5,6,7,8-tetrahydropyrido[3,4-e][3]benzazocin-3(2H)-yl]-4-methoxybutanoic acid (Stereoisomer Mixture)

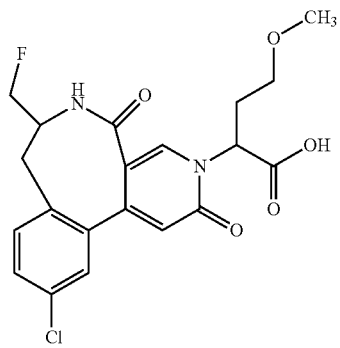 [SMILES: COCCC(C(=O)O)n1cc2c(cc1=O)-c1cc(Cl)ccc1CC(CF)NC2=O]

To a solution of 161 mg (90% purity, 0.31 mmol) of 2-{4-[2-(2-amino-3-fluoropropyl)-5-chlorophenyl]-5-(ethoxycarbonyl)-2-oxopyridin-1(2H)-yl}-4-methoxybutanoic acid (stereoisomer mixture) in 4.3 ml of tetrahydrofuran were added 600 mg of 4 Å molecular sieve, and the mixture was stirred at RT for 2 h. Subsequently, the reaction mixture was admixed at RT with 2.3 ml (6.18 mmol, 20 eq.) of a sodium ethoxide solution (21% in ethanol, dried beforehand over 4 Å molecular sieve for 2 h) and stirred at RT for 90 min. The reaction mixture was admixed with about 0.7 ml of an aqueous hydrochloric acid solution (6 N) to pH 5-6 and concentrated under reduced pressure. The residue was purified by means of preparative HPLC (water/acetonitrile/0.1% formic acid gradient). Yield: 40 mg (71% purity, 22% of theory)

LC/MS [Method 1]: $R_t$=0.66 min; MS (ESIpos): m/z=423 (M+H)$^+$.

Example 12.1E

Methyl 4-({2-[11-chloro-7-(fluoromethyl)-2,5-dioxo-5,6,7,8-tetrahydropyrido[3,4-e][3]benzazocin-3(2H)-yl]-4-methoxybutanoyl}amino)benzoate (Stereoisomer Mixture)

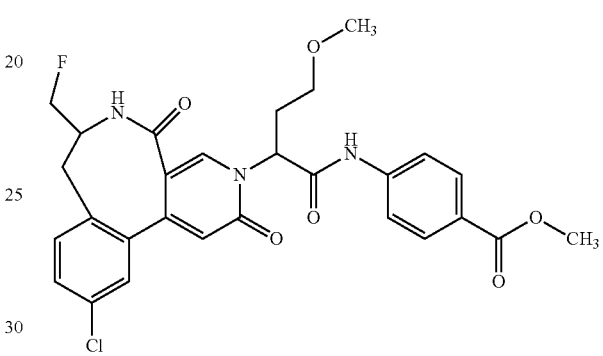

According to General Method 3A, 28 mg (66 μmol) of 2-[11-chloro-7-(fluoromethyl)-2,5-dioxo-5,6,7,8-tetrahydropyrido[3,4-e][3]benzazocin-3(2H)-yl]-4-methoxybutanoic acid (stereoisomer mixture) were reacted with 15 mg (99 μmol, 1.5 eq.) of methyl 4-aminobenzoate. The crude product was purified by preparative HPLC (water/acetonitrile/0.1% formic acid gradient). Yield: 19 mg (52% of theory)

LC/MS [Method 1]: $R_t$=0.88 min; MS (ESIpos): m/z=556 (M+H)$^+$.

Working Examples

General Method 1: Hydrolysis of a Tert-Butyl Ester or a Boc-Protected Amine Using TFA At 0° C. to RT, TFA (10-20 eq.) was added to a solution of the appropriate tert-butyl ester derivative or a Boc-protected amine (1.0 eq.) in dichloromethane (about 25 ml/mmol), and the mixture was stirred at RT for 1 to 8 h. Subsequently, the reaction mixture was concentrated under reduced pressure. The residue was co-evaporated repeatedly with dichloromethane and/or toluene. The crude product was then purified by means of preparative RP-HPLC (acetonitrile/water gradient or water/methanol gradient).

General Method 2: Hydrolysis of a Methyl or Ethyl Ester with Lithium Hydroxide

At RT, lithium hydroxide (2-4 eq.) was added to a solution of the appropriate ester (1.0 eq.) in a mixture of tetrahydrofuran/water (3:1, about 7-15 ml/mmol), and the mixture was stirred at RT. The reaction mixture was then adjusted to pH 1 using aqueous hydrochloric acid solution (1N). After addition of water/ethyl acetate, the aqueous phase was extracted three times with ethyl acetate. The combined organic phases were dried (sodium sulphate or magnesium sulphate), filtered and concentrated under reduced pressure.

The crude product was then purified either by means of normal phase chromatography (cyclohexane/ethyl acetate mixtures or dichloromethane/methanol mixtures) or preparative RP-HPLC (water/acetonitrile gradient or water/methanol gradient).

General Method 3: Amide Coupling Using HATU/DIEA

Under argon and at RT, the appropriate amine (1.1-1.2 eq.), N,N-diisopropylethylamine (DIEA) (2.2-3.0 eq.) and a solution of HATU (1.2 eq.) in a little dimethylformamide were added to a solution of the appropriate carboxylic acid (1.0 eq.) in dimethylformamide (about 7-70 ml/mmol). The reaction mixture was stirred at RT. After addition of water/ethyl acetate and phase separation, the organic phase was washed with water and with saturated aqueous sodium chloride solution, dried (sodium sulphate or magnesium sulphate), filtered and concentrated under reduced pressure. The crude product was then purified either by means of normal phase chromatography (cyclohexane/ethyl acetate mixtures or dichloromethane/methanol mixtures) or preparative RP-HPLC (water/acetonitrile gradient or water/methanol gradient).

General Method 4: Amide Coupling Using T3P/DIEA

Under argon and at 0° C. or RT, N,N-diisopropylethylamine (3 eq.) and propylphosphonic anhydride (T3P, 50% in dimethylformamide or in ethyl acetate, 3 eq.) were added dropwise to a solution of the carboxylic acid and the appropriate amine (1.1-1.5 eq.) in dimethylformamide (0.15-0.05 mmol). The reaction mixture was stirred at RT and then concentrated under reduced pressure. After addition of water/ethyl acetate and phase separation, the aqueous phase was extracted twice with ethyl acetate. The combined organic phases were dried (sodium sulphate or magnesium sulphate), filtered and concentrated under reduced pressure. The crude product was then purified either by flash chromatography (cyclohexane/ethyl acetate mixtures or dichloromethane/methanol mixtures) or preparative HPLC (Reprosil C18, water/acetonitrile gradient or water/methanol gradient).

General Method 5: Amide Coupling Using T3P/Pyridine

A solution of the appropriate carboxylic acid (1 eq.) and the appropriate amine (1.1-1.5 eq.) in pyridine (about 0.1M) was heated to 60 to 90° C., and T3P (50% in dimethylformamide or in ethyl acetate, 1.5-4 eq.) was added dropwise. Alternatively, T3P (50% in dimethylformamide or ethyl acetate, 1.5-4 eq.) was added at RT and the mixture was then stirred at RT or heated to 50 to 90° C. After 1 to 20 h, the reaction mixture was cooled to RT, and water and ethyl acetate were added. The aqueous phase was extracted with ethyl acetate. The combined organic phases were washed with aqueous buffer solution (pH=5), with saturated aqueous sodium hydrogencarbonate solution and with saturated aqueous sodium chloride solution, dried over sodium sulphate and concentrated under reduced pressure. The crude product was then optionally purified either by normal phase chromatography (cyclohexane/ethyl acetate mixtures or dichloromethane/methanol mixtures) or preparative RP-HPLC (water/acetonitrile gradient or water/methanol gradient).

General Method 6: Hydrolysis of a Methyl or Ethyl Ester with Caesium Carbonate

Caesium carbonate (2 eq.) was added to a solution of the appropriate methyl or ethyl ester (1 eq.) in a mixture of methanol/water (4/1, 0.05-0.2M), and the resulting suspension was stirred at RT to 60° C. for 3 h to 8 h. The reaction mixture was then optionally cooled to RT if required and adjusted to pH 3 using aqueous hydrochloric acid (1N). Methanol was removed at 30° C. under reduced pressure. The aqueous phase was extracted with ethyl acetate. The combined organic phases were dried (sodium sulphate or magnesium sulphate), filtered and concentrated under reduced pressure. The residue was purified by means of preparative HPLC.

General Method 7: Amide Coupling with OXIMA/DIC

N,N'-Diisopropylcarbodiimide (DIC) (1 eq.) was added dropwise to a degassed solution of the appropriate carboxylic acid (1 eq.), aniline (1 eq.) and ethyl hydroxyiminocyanoacetate (Oxima) (0.7 eq.) in dimethylformamide (0.06-0.1M), and the resulting reaction solution was stirred at RT to 40° C. for 8 h to 24 h. The solvent was removed under reduced pressure. The residue was either admixed with water and the desired product was filtered off or purified by normal phase chromatography (cyclohexane/ethyl acetate gradient) or preparative RP-HPLC (water/acetonitrile gradient or water/methanol gradient).

Example 1

4-{[2-(10-Chloro-2,5-dioxo-2,5,6,7-tetrahydro-3H-pyrido[3,4-d][2]benzazepin-3-yl)butanoyl]amino}benzoic acid (Stereoisomer Mixture)

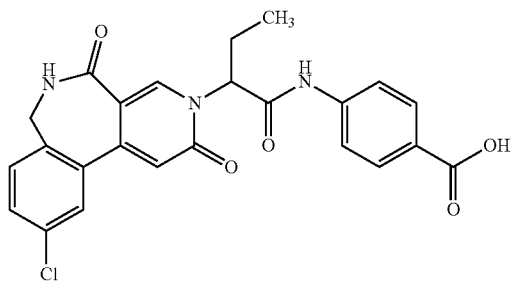 [SMILES: CCC(C(=O)Nc1ccc(C(=O)O)cc1)n1cc2c(cc1=O)-c1cc(Cl)ccc1CNC2=O]

According to General Method 1, 42 mg (80 µmol) of tert-butyl 4-{[2-(10-chloro-2,5-dioxo-2,5,6,7-tetrahydro-3H-pyrido[3,4-d][2]benzazepin-3-yl)butanoyl]amino}benzoate (stereoisomer mixture) were hydrolysed with trifluoroacetic acid. The solvent was removed under reduced pressure, the residue was co-evaporated three times with dichloromethane and three times with toluene, and the residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 31 mg (80% of theory)

LC/MS [Method 1]: $R_t$=0.77 min; MS (ESIpos): m/z=466 (M+H)$^+$, $^1$H-NMR (400 MHz, DMSO-d$_6$): δ [ppm]=12.8 (br. s, 1H), 10.9 (br. s, 1H), 8.54 (br. s, 1H), 8.28 (s, 1H), 7.91 (d, 2H), 7.77-7.71 (m, 3H), 7.54 (dd, 1H), 7.43 (d, 1H), 6.65 (s, 1H), 5.67-5.60 (m, 1H), 4.23-3.89 (2×br. m, 2H), 2.27-2.14 (m, 1H), 2.11-1.98 (m, 1H), 0.93 (t, 3H).

Example 2

2-(10-Chloro-2,5-dioxo-2,5,6,7-tetrahydro-3H-pyrido[3,4-d][2]benzazepin-3-yl)-N-[4-(5-oxo-4,5-dihydro-1,2,4-oxadiazol-3-yl)phenyl]butanamide (Stereoisomer Mixture)

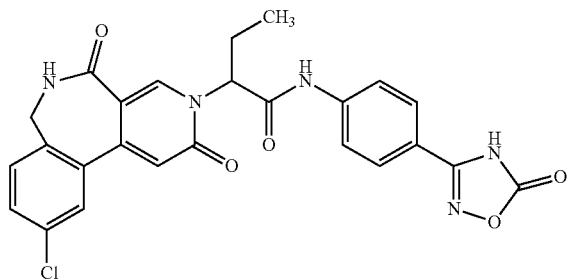 [SMILES: CCC(C(=O)Nc1ccc(-c2noc(=O)[nH]2)cc1)n1cc2c(cc1=O)-c1cc(Cl)ccc1CNC2=O]

75.0 mg (216 μmol) of 2-(10-chloro-2,5-dioxo-2,5,6,7-tetrahydro-3H-pyrido[3,4-d][2]benzazepin-3-yl)butanoic acid (stereoisomer mixture) and 57.5 mg (324 μmol) of 3-(4-aminophenyl)-1,2,4-oxadiazol-5(4H)-one [Zerban, G. et al., WO 2007/071742, Example 1] were initially charged in 5 ml of pyridine. Subsequently, 631 μl (1.30 mmol) of propylphosphonic anhydride (T3P, 50% in ethyl acetate, 4 eq.) were added dropwise in portions and the reaction mixture was stirred at 60° C. for 6 days. The reaction was cooled to room temperature and 50 ml of water were added. The mixture was extracted three times with 30 ml of ethyl acetate. The combined organic phases were washed three times with pH 5 buffer, and the solvent was removed under reduced pressure. The residue was purified by means of preparative HPLC [column: Chromatorex C18, 10 μm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 11.4 mg (10% of theory)

LC/MS [Method 1]: $R_t$=0.08 min; MS (ESIpos): m/z=506 (M+H)$^+$, $^1$H-NMR (400 MHz, DMSO-$d_6$): δ [ppm]=12.9 (br. s, 1H), 10.9 (s, 1H), 8.55 (br. s, 1H), 8.28 (s, 1H), 7.83-7.73 (m, 5H), 7.54 (dd, 1H), 7.43 (d, 1H), 6.66 (s, 1H), 5.68-5.60 (m, 1H), 4.29-3.90 (2×br. m, 2H), 2.26-2.16 (m, 1H), 2.12-1.98 (m, 1H), 0.93 (t, 3H).

Example 3

4-{[2-(10'-Chloro-2',5'-dioxo-5',6'-dihydrospiro[cyclopropane-1,7'-pyrido[3,4-d][2]benzazepine]-3'(2'H)-yl)butanoyl]amino}benzoic acid (Stereoisomer Mixture)

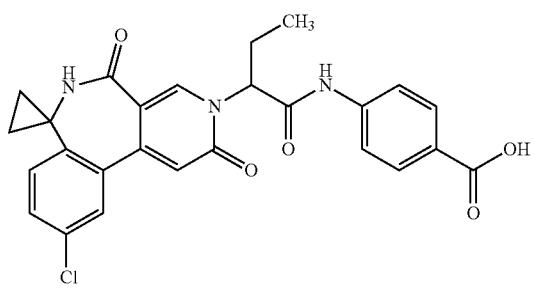 [SMILES: CCC(C(=O)Nc1ccc(C(=O)O)cc1)n1cc2c(cc1=O)-c1cc(Cl)ccc1C1(CC1)NC2=O]

According to General Method 1, 45 mg (82 μmol) of tert-butyl 4-{[2-(10'-chloro-2',5'-dioxo-5',6'-dihydrospiro[cyclopropane-1,7'-pyrido[3,4-d][2]benzazepine]-3'(2'H)-yl)butanoyl]amino}benzoate (stereoisomer mixture) were hydrolysed with trifluoroacetic acid. The solvent was removed under reduced pressure and the residue was purified by means of preparative HPLC [column: Chromatorex C18, 10 μm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 32 mg (78% of theory)

LC/MS [Method 1]: $R_t$=0.82 min; MS (ESIpos): m/z=492 (M+H)$^+$, $^1$H-NMR (400 MHz, DMSO-$d_6$): δ [ppm]=12.8 (br. s, 1H), 10.9 (2×s, 1H), 8.88/8.84 (2×s, 1H), 8.21 (s, 1H), 7.94-7.89 (m, 2H), 7.77-7.71 (m, 3H), 7.52 (dd, 1H), 7.39 (d, 1H), 6.66/6.65 (2×s, 1H), 5.68-5.61 (m, 1H), 2.27-2.16 (m, 1H), 2.12-1.99 (m, 1H), 1.53-1.45 (m, 1H), 1.21-1.11 (m, 1H), 0.98-0.81 (m, 4H), 0.63-0.53 (m, 1H).

Example 4

4-{[(11-Chloro-2,5-dioxo-5,6,7,8-tetrahydropyrido[3,4-e][3]benzazocin-3(2H)-yl)acetyl]amino}benzoic acid

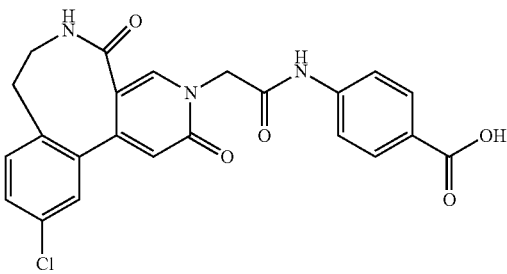 [SMILES: O=C(Cn1cc2c(cc1=O)-c1cc(Cl)ccc1CCNC2=O)Nc1ccc(C(=O)O)cc1]

According to General Method 1, 5.7 mg (11 μmol) of tert-butyl 4-{[(11-chloro-2,5-dioxo-5,6,7,8-tetrahydropyrido[3,4-e][3]benzazocin-3(2H)-yl)acetyl]amino}benzoate were hydrolysed with trifluoroacetic acid. The crude product was purified by means of preparative HPLC (Method 10). Yield: 0.9 mg (17% of theory)

LC/MS [Method 10]: $R_t$=0.85 min; MS (ESIpos): m/z=452 (M+H)$^+$, $^1$H-NMR (400 MHz, DMSO-$d_6$): δ [ppm]=12.7 (br. s, 1H), 10.7 (s, 1H), 7.94-7.89 (m, 3H), 7.76-7.69 (m, 3H), 7.46 (dd, 1H), 7.32 (d, 1H), 7.24 (d, 1H), 6.31 (s, 1H), 4.87 (s, 2H), 3.49-3.42 (m, 1H), 2.99-2.92 (m, 2H).

Example 5

2-(11-Chloro-2,5-dioxo-5,6,7,8-tetrahydropyrido[3,4-e][3]benzazocin-3(2H)-yl)-N-[4-(5-oxo-4,5-dihydro-1,2,4-oxadiazol-3-yl)phenyl]acetamide

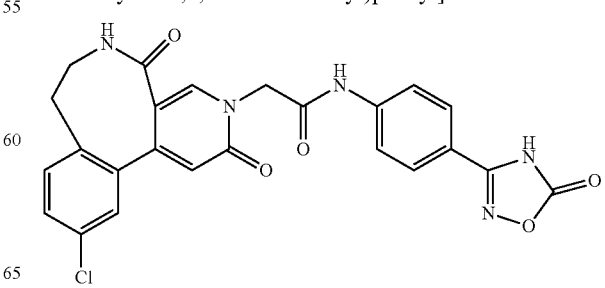

According to General Method 3, 10 mg (30 µmol) of (11-chloro-2,5-dioxo-5,6,7,8-tetrahydropyrido[3,4-e][3]benzazocin-3(2H)-yl)acetic acid were reacted with 6.4 mg (36 µmol, 1.2 eq.) of 3-(4-aminophenyl)-1,2,4-oxadiazol-5(4H)-one [Zerban, G. et al., WO 2007/071742, Example 1]. The crude product was purified by means of preparative HPLC (Method 10). Yield: 2.4 mg (15% of theory)

LC/MS [Method 10]: $R_t$=0.87 min; MS (ESIpos): m/z=492 (M+H)$^+$, $^1$H-NMR (400 MHz, DMSO-d$_6$): δ [ppm]=12.9 (br. s, 1H), 10.7 (s, 1H), 7.91 (s, 1H), 7.78 (s, 4H), 7.73 (t, 1H), 7.46 (dd, 1H), 7.32 (d, 1H), 7.24 (d, 1H), 6.31 (s, 1H), 4.87 (s, 2H), 3.49-3.42 (m, 1H), 3.01-2.91 (m, 2H).

Example 6

4-{[2-(11-Chloro-2,5-dioxo-5,6,7,8-tetrahydropyrido[3,4-e][3]benzazocin-3(2H)-yl)butanoyl]amino}benzoic acid (Stereoisomer Mixture)

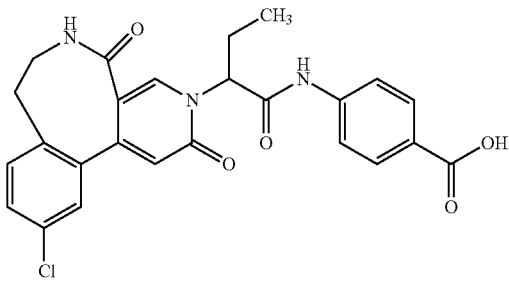 [SMILES: CCC(C(=O)Nc1ccc(C(=O)O)cc1)n1cc2c(cc1=O)-c1cc(Cl)ccc1CCNC2=O]

According to General Method 1, 155 mg (289 µmol) of tert-butyl 4-{[2-(11-chloro-2,5-dioxo-5,6,7,8-tetrahydropyrido[3,4-e][3]benzazocin-3(2H)-yl)butanoyl]amino}benzoate (stereoisomer mixture) were hydrolysed with trifluoroacetic acid, and 11.6 mg of the crude product were purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 9.5 mg (7% of theory)

LC/MS [Method 1]: $R_t$=0.78 min; MS (ESIpos): m/z=480 (M+H)$^+$, $^1$H-NMR (400 MHz, DMSO-d$_6$): δ [ppm]=12.8 (br. s, 1H), 10.8 (s, 1H), 7.93-7.89 (m, 2H), 7.85/7.79 (2×s, 1H), 7.80-7.71 (m, 3H), 7.47-7.43 (m, 1H), 7.31 (d, 1H), 7.28-7.26 (m, 1H), 6.33 (2×s, 1H), 5.63-5.56 (m, 1H), 3.51-3.24 (m, 2H), 2.99-2.90 (m, 2H), 2.23-2.01 (m, 2H), 0.92/0.90 (2×t, 3H).

Example 7

2-(11-Chloro-2,5-dioxo-5,6,7,8-tetrahydropyrido[3,4-e][3]benzazocin-3(2H)-yl)-N-[4-(5-oxo-4,5-dihydro-1,2,4-oxadiazol-3-yl)phenyl]butanamide (Stereoisomer Mixture)

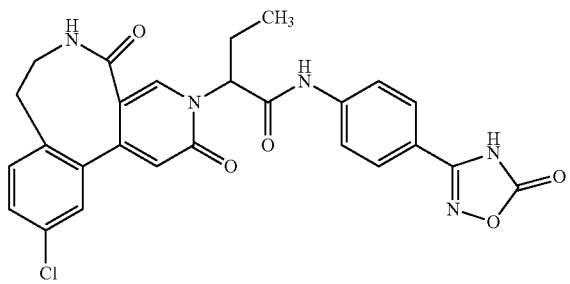 [SMILES: CCC(C(=O)Nc1ccc(-c2noc(=O)[nH]2)cc1)n1cc2c(cc1=O)-c1cc(Cl)ccc1CCNC2=O]

14 mg (39 µmol) of 2-(11-chloro-2,5-dioxo-5,6,7,8-tetrahydropyrido[3,4-e][3]benzazocin-3(2H)-yl)butanoic acid (stereoisomer mixture) were dissolved in 0.7 ml of dimethylformamide, and 6.9 mg (39 µmol) of 3-(4-aminophenyl)-1,2,4-oxadiazol-5(4H)-one [Zerban, G. et al., WO 2007/071742, Example 1] and 5.5 mg (39 µmol) of Oxyma were added. Subsequently, 6.2 µl (39 µmol) of di-iso-propylcarbodiimide were added dropwise and the reaction solution was agitated at 40° C. overnight. The solvent was removed under reduced pressure and the residue was purified by means of preparative HPLC (Method 10). Yield: 3.3 mg (16% of theory)

LC/MS [Method 1]: $R_t$=0.81 min; MS (ESIpos): m/z=520 (M+H)$^+$, $^1$H-NMR (400 MHz, DMSO-d$_6$): δ [ppm]=12.8 (br. s, 1H), 10.9 (s, 1H), 7.87-7.75 (m, 6H), 7.48-7.44 (m, 1H), 7.32 (d, 1H), 7.29-7.26 (m, 1H), 6.34 (2×s, 1H), 5.63-5.56 (m, 1H), 3.51-3.23 (m, 2H), 3.00-2.90 (m, 2H), 2.25-2.03 (m, 2H), 0.92/0.91 (2×t, 3H).

Example 8

4-{[2-(11-Chloro-2,5-dioxo-5,6,7,8-tetrahydropyrido[3,4-e][3]benzazocin-3(2H)-yl)-4-methylpentanoyl]amino}benzoic acid (Stereoisomer Mixture)

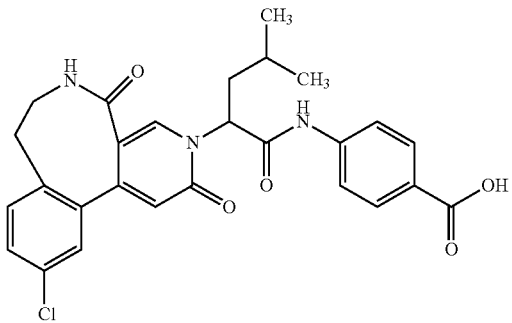 [SMILES: CC(C)CC(C(=O)Nc1ccc(C(=O)O)cc1)n1cc2c(cc1=O)-c1cc(Cl)ccc1CCNC2=O]

According to General Method 1, 12 mg (21 µmol) of tert-butyl 4-{[2-(11-chloro-2,5-dioxo-5,6,7,8-tetrahydropyrido[3,4-e][3]benzazocin-3(2H)-yl)-4-methylpentanoyl]amino}benzoate (stereoisomer mixture) were hydrolysed with trifluoroacetic acid. The solvent was removed under reduced pressure, and the residue was co-evaporated three times dichloromethane and three times with toluene and finally lyophilized from acetonitrile/water. Yield: 8.6 mg (79% of theory)

LC/MS [Method 1]: $R_t$=0.88 min; MS (ESIpos): m/z=508 (M+H)$^+$, $^1$H-NMR (400 MHz, DMSO-d$_6$): δ [ppm]=12.8 (br. s, 1H), 10.9 (s, 1H), 7.94-7.70 (m, 6H), 7.47-7.42 (m, 1H), 7.33-7.26 (m, 2H), 6.34/6.33 (2×s, 1H), 5.87-5.80 (m, 1H), 3.47-3.23 (m, 2H), 3.00-2.87 (m, 2H), 2.17-2.06 (m, 1H), 1.94-1.84 (m, 1H), 1.51-1.39 (m, 1H), 0.97-0.91 (m, 6H).

Example 9

2-(11-Chloro-2,5-dioxo-5,6,7,8-tetrahydropyrido[3,4-e][3]benzazocin-3(2H)-yl)-4-methyl-N-[4-(5-oxo-4,5-dihydro-1,2,4-oxadiazol-3-yl)phenyl]pentanamide (Stereoisomer Mixture)

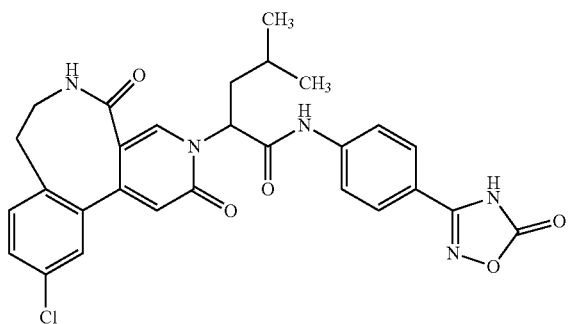 [SMILES: CC(C)CC(C(=O)Nc1ccc(-c2noc(=O)[nH]2)cc1)n1cc2c(cc1=O)-c1cc(Cl)ccc1CCNC2=O]

15 mg (39 µmol) of 2-(11-chloro-2,5-dioxo-5,6,7,8-tetrahydropyrido[3,4-e][3]benzazocin-3(2H)-yl)-4-methylpentanoic acid (stereoisomer mixture) were dissolved in 0.4 ml of dimethylformamide, and 6.8 mg (39 µmol) of 3-(4-aminophenyl)-1,2,4-oxadiazol-5(4H)-one [Zerban, G. et al., WO 2007/071742, Example 1] and 5.5 mg (39 µmol) of Oxyma were added. Subsequently, 6.0 µl (39 µmol) of di-iso-propylcarbodiimide were added dropwise and the reaction solution was agitated at 40° C. overnight. A further 14 mg (78 µmol) of 3-(4-aminophenyl)-1,2,4-oxadiazol-5(4H)-one and 12 µl (78 µmol) of di-iso-propylcarbodiimide were added and the mixture was agitated at 40° C. until conversion was complete. The solvent was removed under reduced pressure and the residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 6.6 mg (31% of theory)

LC/MS [Method 1]: $R_t$=0.91 min; MS (ESIpos): m/z=548 (M+H)$^+$, $^1$H-NMR (400 MHz, DMSO-d$_6$): δ [ppm]=12.9 (br. s, 1H), 10.9 (2×s, 1H), 7.90-7.74 (m, 6H), 7.48-7.43 (m, 1H), 7.33-7.26 (m, 2H), 6.35/6.34 (2×s, 1H), 5.87-5.80 (m, 1H), 3.46-3.23 (m, 2H), 2.99-2.87 (m, 2H), 2.18-2.08 (m, 1H), 1.94-1.84 (m, 1H), 1.51-1.39 (m, 1H), 0.97-0.91 (m, 6H).

Example 10

4-{[2-(11'-Chloro-2',5'-dioxo-2',5',6',8'-tetrahydro-3'H-spiro[cyclopropane-1,7'-pyrido[3,4-e][3]benzazocine]-3'-yl)butanoyl]amino}benzoic acid (Stereoisomer Mixture)

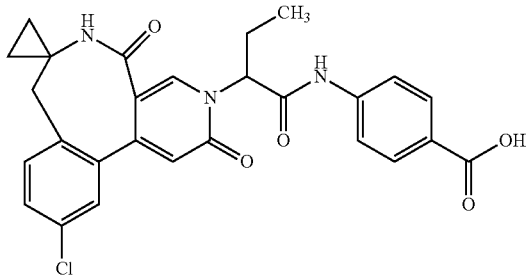 [SMILES: CCC(C(=O)Nc1ccc(C(=O)O)cc1)n1cc2c(cc1=O)-c1cc(Cl)ccc1CC1(CC1)NC2=O]

According to General Method 1, 87.0 mg (155 µmol) of tert-butyl 4-{[2-(11'-chloro-2',5'-dioxo-2',5',6',8'-tetrahydro-3'H-spiro[cyclopropane-1,7'-pyrido[3,4-e][3]benzazocine]-3'-yl)butanoyl]amino}benzoate (stereoisomer mixture) were hydrolysed with trifluoroacetic acid. The solvent was removed under reduced pressure and the residue was co-evaporated repeatedly with dichloromethane and purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 61.5 mg (79% of theory)

LC/MS [Method 1]: $R_t$=0.82/0.83 min; MS (ESIpos): m/z=506 (M+H)$^+$, $^1$H-NMR (400 MHz, DMSO-d$_6$): δ [ppm]=12.8 (br. s, 1H), 10.8 (2×s, 1H), 8.15-8.09 (2×s, 1H), 7.94-7.69 (m, 5H), 7.45 (dd, 1H), 7.33-7.28 (m, 2H), 6.33/6.32 (2×s, 1H), 5.72/5.62 (2×dd, 1H), 3.28-3.17 (m, 1H), 2.74-2.63 (m, 1H), 2.23-2.03 (m, 2H), 1.03-0.87 (m, 4H), 0.80-0.64 (m, 3H).

Example 11

2-(11'-Chloro-2',5'-dioxo-2',5',6',8'-tetrahydro-3'H-spiro[cyclopropane-1,7'-pyrido[3,4-e][3]benzazocine]-3'-yl)-N-[4-(5-oxo-4,5-dihydro-1,2,4-oxadiazol-3-yl)phenyl]butanamide (Stereoisomer Mixture)

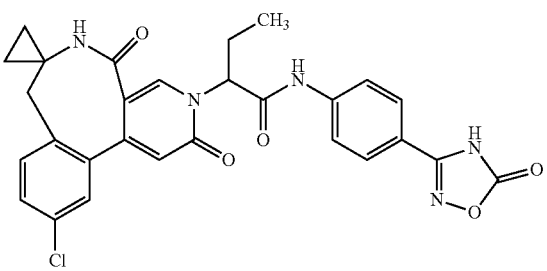 [SMILES: CCC(C(=O)Nc1ccc(-c2noc(=O)[nH]2)cc1)n1cc2c(cc1=O)-c1cc(Cl)ccc1CC1(CC1)NC2=O]

8.0 mg (19 µmol) of 2-(11'-chloro-2',5'-dioxo-2',5',6',8'-tetrahydro-3'H-spiro[cyclopropane-1,7'-pyrido[3,4-e][3]benzazocine]-3'-yl)butanoic acid (stereoisomer mixture) were dissolved in 0.4 ml of dimethylformamide, and 3.3 mg (19 µmol) of 3-(4-aminophenyl)-1,2,4-oxadiazol-5(4H)-one [Zerban, G. et al., WO 2007/071742, Example 1] and 0.3 mg (2 µmol) of Oxyma were added. Subsequently, 2.9 µl (19 µmol) of di-iso-propylcarbodiimide were added dropwise and the reaction solution was agitated at 40° C. overnight. The solvent was removed under reduced pressure and the residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)] and finally purified by means of preparative HPLC (Method 10). Yield: 1.1 mg (11% of theory)

LC/MS [Method 10]: $R_t$=0.96/0.98 min; MS (ESIpos): m/z=546 (M+H)$^+$, $^1$H-NMR (400 MHz, DMSO-d$_6$): δ [ppm]=12.9 (br. s, 1H), 10.8 (2×s, 1H), 8.15/8.09 (2×s, 1H), 7.86-7.70 (m, 5H), 7.45 (dd, 1H), 7.33-7.27 (m, 2H), 6.33/6.32 (2×s, 1H), 5.72/5.62 (2×dd, 1H), 3.27-3.17 (m, 1H), 2.73-2.64 (m, 1H), 2.24-2.04 (m, 2H), 1.03-0.87 (m, 4H), 0.80-0.65 (m, 3H).

Example 12

4-{[2-(11'-Chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}benzoic acid (Stereoisomer Mixture)

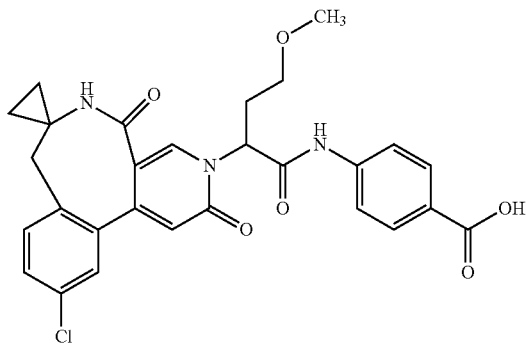 [SMILES: COCCC(C(=O)Nc1ccc(C(=O)O)cc1)n1cc2c(cc1=O)-c1cc(Cl)ccc1CC1(CC1)NC2=O]

According to General Method 1, 27 mg (45 µmol) of tert-butyl 4-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}benzoate (stereoisomer mixture) were hydrolysed with trifluoroacetic acid. The crude product was purified by preparative RP-HPLC (Reprosil C18, water/acetonitrile gradient). Yield: 13 mg (55% of theory)

LC/MS [Method 2]: $R_t$=2.27 min/2.31 min; MS (ESIpos): m/z=536 (M+H)$^+$, $^1$H-NMR (400 MHz, DMSO-d$_6$): δ [ppm]=12.75 (br. s, 1H), 10.82/10.75 (2×s, 1H), 8.14/8.07 (2×s, 1H), 7.94-7.71 (2×m, 5H), 7.45 (dd, 1H), 7.31 (d, 1H), 7.30-7.26 (m, 1H), 6.31 (s, 1H), 5.86/5.76 (t/dd, 1H), 3.45-3.36 (m, 1H), 3.3-3.14 (m, 2H), 3.23/3.20 (2×s, 3H), 2.75-2.65 (m, 1H), 2.44-2.30 (m, 2H), 1.04-0.93 (m, 1H), 0.82-0.72 (m, 2H), 0.72-0.64 (m, 1H).

Example 13

4-{[2-(11'-Chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}-2-fluorobenzamide (Stereoisomer Mixture)

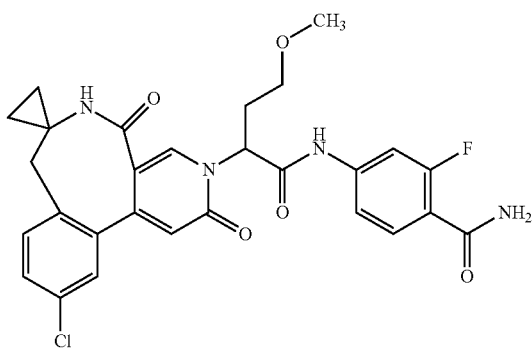 [SMILES: COCCC(C(=O)Nc1ccc(C(N)=O)c(F)c1)n1cc2c(cc1=O)-c1cc(Cl)ccc1CC1(CC1)NC2=O]

According to General Method 5, 63 mg (0.15 mmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 35 mg (0.23 mmol, 1.5 eq.) of 4-amino-2-fluorobenzamide. After aqueous workup, the crude product was purified by means of preparative RP-HPLC (Reprosil C18, water/acetonitrile gradient). Yield: 21 mg (24% of theory)

LC/MS [Method 2]: $R_t$=2.15 min/2.18 min; MS (ESIpos): m/z=553 (M+H)$^+$, $^1$H-NMR (400 MHz, DMSO-d$_6$): δ [ppm]=10.90/10.80 (2×s, 1H), 8.14/8.08 (2×s, 1H), 7.87/7.72 (2×s, 1H), 7.71-7.59 (m, 2H), 7.57-7.50 (m, 2H), 7.45 (dd, 1H), 7.42 (dd, 1H), 7.31 (d, 1H), 7.29-7.25 (m, 1H), 6.32 (s, 1H), 5.84/5.73 (t/dd, 1H), 3.45-3.36 (m, 1H), 3.3-3.25 (m, 2H), 3.23/3.20 (2×s, 3H), 2.69 (dd, 1H), 2.45-2.27 (m, 2H), 1.04-0.92 (m, 1H), 0.82-0.63 (m, 3H).

Example 14

2-(11'-Chloro-2',5'-dioxo-2',5',6',8'-tetrahydro-3'H-spiro[cyclopropane-1,7'-pyrido[3,4-e][3]benzazocine]-3'-yl)-4-methoxy-N-(2-oxo-2,3-dihydro-1H-benzimidazol-5-yl)butanamide (Stereoisomer Mixture)

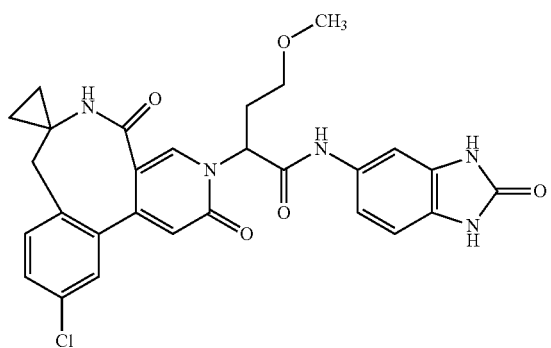 [SMILES: COCCC(C(=O)Nc1ccc2[nH]c(=O)[nH]c2c1)n1cc2c(cc1=O)-c1cc(Cl)ccc1CC1(CC1)NC2=O]

According to General Method 3, 30 mg (72 µmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 12 mg (79 µmol, 1.1 eq.) of 5-amino-1,3-dihydro-2H-benzimidazol-2-one. The crude product was purified by preparative RP-HPLC (Reprosil C18, water/acetonitrile gradient). Yield: 21 mg (53% of theory)

LC/MS [Method 1]: $R_t$=0.68 min/0.70 min; MS (ESIpos): m/z=548 (M+H)$^+$, $^1$H-NMR (400 MHz, DMSO-d$_6$): δ [ppm]=10.59/10.55/10.51 (3×s, 2H), 10.37/10.33 (2×s, 1H), 8.13/8.06 (2×s, 1H), 7.89/7.71 (2×s, 1H), 7.48-7.40 (m, 2H), 7.34-7.25 (m, 2H), 7.10/7.07 (2×dd, 1H), 6.85 (d, 1H), 6.30 (s, 1H), 5.82/5.76 (t/dd, 1H), 3.43-3.35 (m, 1H), 3.3-3.15 (m, 2H), 3.23/3.21 (2×s, 3H), 2.69 (dd, 1H), 2.43-2.22 (m, 2H), 1.01-0.92 (m, 1H), 0.80-0.61 (m, 3H).

Example 15

2-(11'-Chloro-2',5'-dioxo-2',5',6',8'-tetrahydro-3'H-spiro[cyclopropane-1,7'-pyrido[3,4-e][3]benzazocine]-3'-yl)-4-methoxy-N-(2-methyl-2H-indazol-5-yl)butanamide (Stereoisomer Mixture)

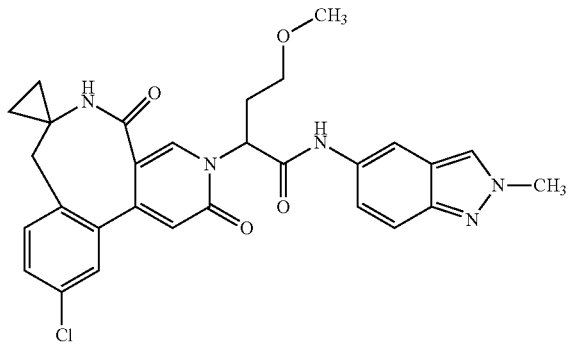 [SMILES: COCCC(C(=O)Nc1ccc2nn(C)cc2c1)n1cc2c(cc1=O)-c1cc(Cl)ccc1CC1(CC1)NC2=O]

According to General Method 3, 30 mg (72 µmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 12 mg (79 µmol, 1.1 eq.) of 2-methyl-2H-indazol-5-amine. The crude product was purified by means of preparative RP-HPLC (Reprosil C18, water/acetonitrile gradient). Yield: 26 mg (66% of theory)

LC/MS [Method 1]: $R_t$=0.82 min/0.83 min; MS (ESIpos): m/z=546 (M+H)$^+$, $^1$H-NMR (400 MHz, DMSO-d$_6$): δ [ppm]=10.45/10.41 (2×s, 1H), 8.26 (d, 1H), 8.14 (s, 1H), 8.08 (d, 1H), 7.91/7.74 (2×s, 1H), 7.55 (d, 1H), 7.45 (dt, 1H), 7.34-7.26 (m, 3H), 6.31 (s, 1H), 5.88/5.80 (t/dd, 1H), 4.13 (s, 3H), 3.45-3.36 (m, 1H), 3.3-3.16 (m, 2H), 3.24/3.21 (2×s, 3H), 2.69 (dd, 1H), 2.45-2.25 (m, 2H), 1.04-0.92 (m, 1H), 0.82-0.62 (m, 3H).

Example 16

2-(11'-Chloro-2',5'-dioxo-2',5',6',8'-tetrahydro-3'H-spiro[cyclopropane-1,7'-pyrido[3,4-e][3]benzazocine]-3'-yl)-4-methoxy-N-(pyrazolo[1,5-a]pyridin-5-yl)butanamide (Stereoisomer Mixture)

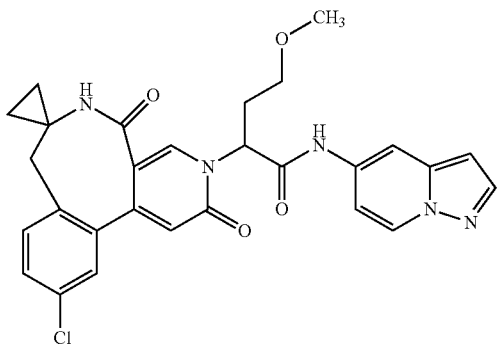 [SMILES: COCCC(C(=O)Nc1ccn2nccc2c1)n1cc2c(cc1=O)-c1cc(Cl)ccc1CC1(CC1)NC2=O]

According to General Method 4, 83 mg (0.2 mmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 35 mg (0.26 mmol, 1.3 eq.) of pyrazolo[1,5-a]pyridin-5-amine [B. C. Baguley et al. *Bioorganic and Medicinal Chemistry*, 2012, 20, 69-85]. After aqueous workup, the crude product was purified by means of preparative RP-HPLC (Reprosil C18, water/acetonitrile gradient). Yield: 82 mg (77% of theory)

LC/MS [Method 1]: $R_t$=0.80 min; MS (ESIpos): m/z=532 (M+H)$^+$, $^1$H-NMR (400 MHz, DMSO-d$_6$): δ [ppm]=10.78/10.70 (2×s, 1H), 8.62 (d, 1H), 8.17-8.05 (m, 2H), 7.94-7.88 (m, 1H), 7.74 (s, 1H), 7.45 (dd, 1H), 7.34-7.25 (m, 2H), 6.99 (dd, 1H), 6.51 (dd, 1H), 6.32 (s, 1H), 5.87/5.76 (t/dd, 1H), 3.46-3.77 (m, 1H), 3.3-3.15 (m, 2H), 3.24/3.21 (2×s, 3H), 2.69 (dd, 1H), 2.45-2.28 (m, 2H), 1.02-0.93 (m, 1H), 0.82-0.63 (m, 3H).

Example 17

2-(11'-Chloro-2',5'-dioxo-2',5',6',8'-tetrahydro-3'H-spiro[cyclopropane-1,7'-pyrido[3,4-e][3]benzazocine]-3'-yl)-N-(imidazo[1,2-a]pyridin-6-yl)-4-methoxybutanamide (Stereoisomer Mixture)

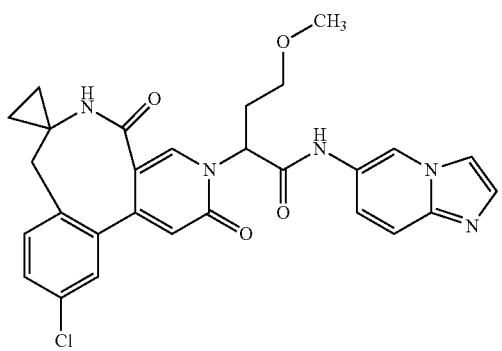 [SMILES: COCCC(C(=O)Nc1ccc2nccn2c1)n1cc2c(cc1=O)-c1cc(Cl)ccc1CC1(CC1)NC2=O]

According to General Method 3, 30 mg (72 µmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 11 mg (79 µmol, 1.1 eq.) of imidazo[1,2-a]pyridin-6-amine. The crude product was purified by means of preparative RP-HPLC (Reprosil C18, water/acetonitrile gradient). Yield: 21 mg (54% of theory)

LC/MS [Method 1]: $R_t$=0.63 min/0.64 min; MS (ESIpos): m/z=532 (M+H)$^+$, $^1$H-NMR (400 MHz, DMSO-d$_6$): δ [ppm]=11.11/10.95 (2×s, 1H), 9.60/9.51 (2×s, 1H), 8.40 (d, 1H), 8.18-8.06 (m, 2H), 7.98-7.89 (m, 1.5H), 7.89-7.82 (m, 1H), 7.76 (s, 0.5H), 7.49-7.43 (m, 1H), 7.32 (d, 1H), 7.26 (dd, 1H), 6.33 (s, 1H), 5.91/5.71 (t/dd, 1H), 3.49-3.40 (m, 2H), 3.3-3.14 (m, 1H), 3.24/3.21 (2×s, 3H), 2.70 (dd, 1H), 2.47-2.37 (m, 2H), 1.04-0.92 (m, 1H), 0.83-0.65 (m, 3H).

Example 18

2-(11'-Chloro-2',5'-dioxo-2',5',6',8'-tetrahydro-3'H-spiro[cyclopropane-1,7'-pyrido[3,4-e][3]benzazocine]-3'-yl)-N-(1H-indazol-5-yl)-4-methoxybutanamide (Stereoisomer Mixture)

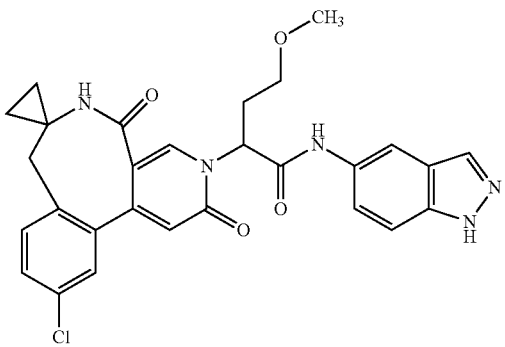 [SMILES: COCCC(C(=O)Nc1ccc2[nH]ncc2c1)n1cc2c(cc1=O)-c1cc(Cl)ccc1CC1(CC1)NC2=O]

According to General Method 3, 30 mg (72 μmol) of 2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoic acid (stereoisomer mixture) were reacted with 11 mg (79 μmol, 1.1 eq.) of 1H-indazol-5-amine. The crude product was purified by means of preparative RP-HPLC (Reprosil C18, water/acetonitrile gradient). Yield: 26 mg (68% of theory)

LC/MS [Method 1]: $R_t$=0.77 min/0.78 min; MS (ESIpos): m/z=532 (M+H)$^+$, $^1$H-NMR (400 MHz, DMSO-d$_6$): δ [ppm]=13.00 (s, 1H), 10.52/10.47 (2×s, 1H), 8.14/8.10/8.07 (3×s, 2H), 8.02 (d, 1H), 7.91/7.74 (2×s, 1H), 7.53-7.42 (m, 3H), 7.31 (d, 1H), 7.29-7.26 (m, 1H), 6.32 (s, 1H), 5.89/5.81 (t/dd, 1H), 3.45-3.37 (m, 1H), 3.3-3.15 (m, 2H), 3.25/3.22 (2×s, 3H), 2.69 (dd, 1H), 2.46-2.25 (m, 2H), 1.04-0.93 (m, 1H), 0.82-0.61 (m, 3H).

Example 19

2-(11'-Chloro-2',5'-dioxo-2',5',6',8'-tetrahydro-3'H-spiro[cyclopropane-1,7'-pyrido[3,4-e][3]benzazocine]-3'-yl)-4-methoxy-N-(2-methyl-3-oxo-2,3-dihydro-1H-indazol-6-yl)butanamide (Stereoisomer Mixture)

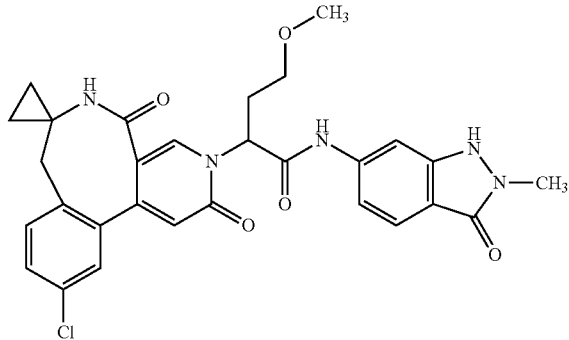 [SMILES: COCCC(C(=O)Nc1ccc2c(=O)n(C)[nH]c2c1)n1cc2c(cc1=O)-c1cc(Cl)ccc1CC1(CC1)NC2=O]

According to General Method 1, 81 mg (122 μmol) of tert-butyl 6-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}-2-methyl-3-oxo-2,3-dihydro-1H-indazole-1-carboxylate (stereoisomer mixture) were reacted with trifluoroacetic acid. The crude product was purified by means of preparative RP-HPLC (Reprosil C18, water/acetonitrile gradient). Yield: 35 mg (51% of theory)

LC/MS [Method 1]: $R_t$=0.70 min/0.72 min; MS (ESIpos): m/z=562 (M+H)$^+$, $^1$H-NMR (400 MHz, DMSO-d$_6$): δ [ppm]=10.74/10.70 (2×s, 1H), 10.23/10.21 (2×s, 1H), 8.15/8.09 (2×s, 1H), 7.89/7.73 (2×s, 1H), 7.76 (d, 1H), 7.56 (d, 1H), 7.45 (dd, 1H), 7.31 (d, 1H), 7.30-7.26 (m, 1H), 7.20-7.15 (m, 1H), 6.31 (s, 1H), 5.87/5.79 (t/dd, 1H), 3.45-3.37 (m, 1H), 3.3-3.15 (m, 2H), 3.23/3.21 (m, 3H), 2.69 (dd, 1H), 2.46-2.29 (m, 2H), 1.05-0.93 (m, 1H), 0.82-0.63 (m, 3H).

Example 20

5-{[2-(11'-Chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}pyridine-2-carboxylic acid (Stereoisomer Mixture)

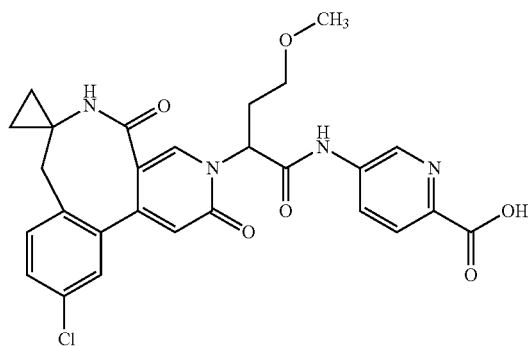 [SMILES: COCCC(C(=O)Nc1ccc(C(=O)O)nc1)n1cc2c(cc1=O)-c1cc(Cl)ccc1CC1(CC1)NC2=O]

According to General Method 2, 135 mg (89% purity, 218 μmol) of methyl 5-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}pyridine-2-carboxylate (stereoisomer mixture) were hydrolysed in the presence of lithium hydroxide. After aqueous work-up, the crude product was purified by preparative RP-HPLC (Reprosil C18, water/acetonitrile gradient). Yield: 41 mg (35% of theory)

LC/MS [Method 1]: $R_t$=0.70 min; MS (ESIpos): m/z=537 (M+H)$^+$, $^1$H-NMR (400 MHz, DMSO-d$_6$): δ [ppm]=13.0 (br. s, 1H), 11.06/10.94 (2×s, 1H), 8.92/8.86 (2×d, 1H), 8.27-8.20 (m, 1H), 8.14/8.09 (2×s, 1H), 8.05 (d, 1H), 7.88/7.74 (2×s, 1H), 7.45 (dd, 1H), 7.34- 7.25 (m, 2H), 6.32 (s, 1H), 5.88/5.74 (t/dd, 1H), 3.45-3.38 (m, 1H), 3.3-3.15 (m, 2H), 3.24/3.21 (2×s, 3H), 2.69 (dd, 1H), 2.47-2.31 (m, 2H), 1.03-0.92 (m, 1H), 0.82-0.64 (m, 3H).

Example 21

5-{[2-(11'-Chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}pyridine-2-carboxamide (Stereoisomer Mixture)

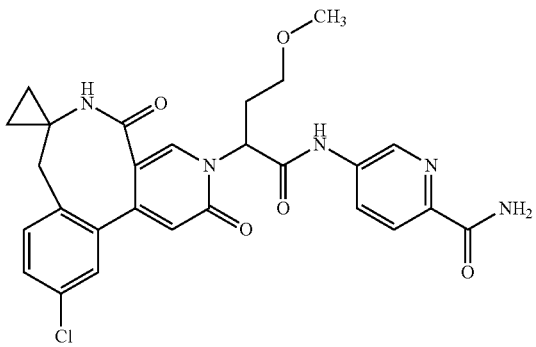 [SMILES: COCCC(C(=O)Nc1ccc(C(N)=O)nc1)n1cc2c(cc1=O)-c1cc(Cl)ccc1CC1(CC1)NC2=O]

According to General Method 4, 41 mg (76 µmol) of 5-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]-amino}pyridine-2-carboxylic acid (stereoisomer mixture) were reacted with 7 mg (89 µmol, 1.2 eq.) of ammonium acetate. The crude product was purified by means of preparative RP-HPLC (Reprosil C18, water/acetonitrile gradient). Yield: 2 mg (6% of theory)

LC/MS [Method 2]: $R_t$=2.03 min/2.07 min; MS (ESIpos): m/z=536 (M+H)$^+$, $^1$H-NMR (400 MHz, DMSO-d$_6$): δ [ppm]=11.08-10.85 (m, 1H), 8.94-8.79 (m, 1H), 8.28-8.17 (m 1H), 8.11 (d, 1H), 8.07-7.97 (m, 2H), 7.89/7.73 (2×s, 1H), 7.53 (s, 1H), 7.46 (d, 1H), 7.37-7.24 (m, 2H), 6.32 (s, 1H), 5.93-5.70 (2×m, 1H), 3.47-3.38 (m, 1H), 3.3-3.13 (m, 2H), 3.24/3.21 (2×s, 3H), 2.69 (dd, 1H), 2.46-2.29 (m, 2H), 1.04-0.93 (m, 1H), 0.83-0.63 (m, 3H).

Example 22

5-{[2-(11'-Chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}thiophene-2-carboxylic acid (Stereoisomer Mixture)

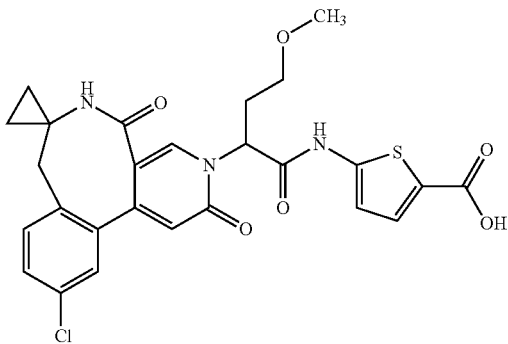 [SMILES: COCCC(C(=O)Nc1ccc(C(=O)O)s1)n1cc2c(cc1=O)-c1cc(Cl)ccc1CC1(CC1)NC2=O]

According to General Method 2, 66 mg (0.12 mmol) of methyl 5-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}thiophene-2-carboxylate (stereoisomer mixture) were hydrolysed with lithium hydroxide. After aqueous work-up, the crude product was purified by preparative RP-HPLC (Reprosil C18, water/acetonitrile gradient). Yield: 10 mg (15% of theory)

LC/MS [Method 2]: $R_t$=2.31 min/2.35 min; MS (ESIpos): m/z=542 (M+H)$^+$, $^1$H-NMR (400 MHz, DMSO-d$_6$): δ [ppm]=12.6 (br. s, 1H), 12.13/11.96 (2×s, 1H), 8.14/8.09 (2×s, 1H), 7.89/7.74 (2×s, 1H), 7.56-7.49 (m, 1H), 7.49-7.41 (m, 1H), 7.35-7.24 (m, 2H), 6.84-6.76 (m, 1H), 6.31 (s, 1H), 5.86/5.68 (2×dd, 1H), 3.45-3.35 (m, 1H), 3.3-3.14 (m, 2H), 3.23/3.20 (2×s, 3H), 2.70 (dd, 1H), 2.47-2.29 (m, 2H), 1.04-0.93 (m, 1H), 0.82-0.64 (m, 3H).

Example 23

5-{[2-(11'-Chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}thiophene-3-carboxylic acid (Stereoisomer Mixture)

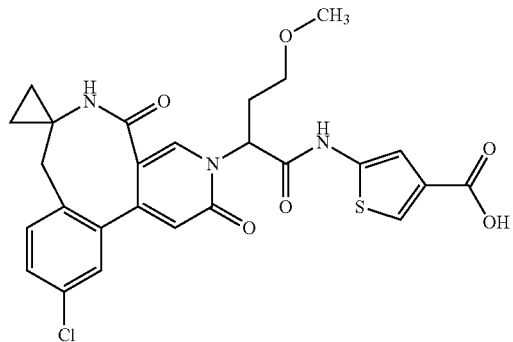 [SMILES: COCCC(C(=O)Nc1cc(C(=O)O)cs1)n1cc2c(cc1=O)-c1cc(Cl)ccc1CC1(CC1)NC2=O]

According to General Method 2, 116 mg (0.21 mmol) of methyl 5-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}thiophene-3-carboxylate (stereoisomer mixture) were hydrolysed with lithium hydroxide (stirring at oil bath temperature 80° C. for 50 h). After aqueous work-up, the crude product was purified by preparative RP-HPLC (Reprosil C18, water/acetonitrile gradient). Yield: 9 mg (8% of theory)

LC/MS [Method 1]: $R_t$=0.81 min; MS (ESIpos): m/z=542 (M+H)$^+$, $^1$H-NMR (400 MHz, DMSO-d$_6$): δ [ppm]=12.5 (br. s, 1H), 11.87/11.68 (2×s, 1H), 8.13/8.09 (2×s, 1H), 7.88/7.73 (2×s, 1H), 7.70 (d, 1H), 7.49-7.41 (m, 1H), 7.35-7.25 (m, 2H), 7.04 (s, 1H), 6.31 (s, 1H), 5.85/5.66 (2×dd, 1H), 3.45-3.35 (m, 1H), 3.3-3.14 (m, 2H), 3.24/3.21 (2×s, 3H), 2.70 (dd, 1H), 2.46-2.28 (m, 2H), 1.04-0.92 (m, 1H), 0.82-0.64 (m, 3H).

Example 24

4-{[2-(11'-Chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}thiophene-2-carboxylic acid (Stereoisomer Mixture)

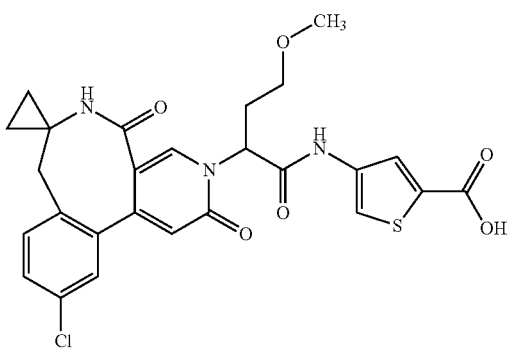 [SMILES: COCCC(C(=O)Nc1csc(C(=O)O)c1)n1cc2c(cc1=O)-c1cc(Cl)ccc1CC1(CC1)NC2=O]

According to General Method 2, 83 mg (0.15 mmol) of methyl 4-{[2-(11'-chloro-2',5'-dioxo-2',5',6',8'-tetrahydro-3'H-spiro[cyclopropane-1,7'-pyrido[3,4-e][3]benzazocine]-3'-yl)-4-methoxybutanoyl]amino}thiophene-2-carboxylate (stereoisomer mixture) were hydrolysed with lithium hydroxide (stirring at oil bath temperature 80° C. for 3 h). After aqueous work-up, the crude product was purified by preparative RP-HPLC (Reprosil C18, water/acetonitrile gradient). Yield: 55 mg (68% of theory)

LC/MS [Method 2]: $R_t$=2.33/2.36 min; MS (ESIpos): m/z=542 (M+H)$^+$, $^1$H-NMR (400 MHz, DMSO-$d_6$): δ [ppm]=13.2 (br. s, 1H), 11.00/10.88 (2×s, 1H), 8.13/8.09 (2×s, 1H), 7.87/7.72 (2×s, 1H), 7.85-7.77 (2×dd, 2H), 7.45 (dt, 1H), 7.31 (d, 1H), 7.28 (t, 1H), 6.31 (s, 1H), 5.80/5.66 (2×dd, 1H), 3.43-3.35 (m, 1H), 3.3-3.16 (m, 2H), 3.24/3.21 (2×s, 3H), 2.69 (dd, 1H), 2.46-2.25 (m, 2H), 1.02-0.92 (m, 1H), 0.81-0.63 (m, 3H).

Example 25

4-{[2-(11'-Chloro-2',5'-dioxo-2',5',6',8'-tetrahydro-3'H-spiro[cyclopropane-1,7'-pyrido[3,4-e][3]benzazocine]-3'-yl)-3-(trans-4-methoxycyclohexyl)propanoyl]amino}benzoic acid (Stereoisomer Mixture)

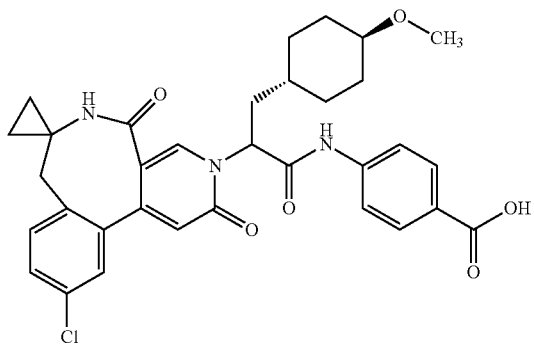 [SMILES: CO[C@H]1CC[C@H](CC(C(=O)Nc2ccc(C(=O)O)cc2)n2cc3c(cc2=O)-c2cc(Cl)ccc2CC2(CC2)NC3=O)CC1]

According to General Method 6, 41 mg (65 µmol) of ethyl 4-{[2-(11'-chloro-2',5'-dioxo-2',5',6',8'-tetrahydro-3'H-spiro[cyclopropane-1,7'-pyrido[3,4-e][3]benzazocine]-3'-yl)-3-(trans-4-methoxycyclohexyl)propanoyl]amino}benzoate (stereoisomer mixture) were hydrolysed with 42.3 mg (130 µmol, 2 eq.) of caesium carbonate. The crude product was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 6.1 mg (15% of theory)

LC/MS [Method 2]: $R_t$=2.69 min/2.76 min; MS (ESIpos): m/z=604 (M+H)$^+$, $^1$H-NMR (400 MHz, DMSO-$d_6$): δ [ppm]=10.80/10.75 (2×s, 1H), 8.16/8.09 (2×s, 1H), 7.92-7.62 (m, 5H), 7.48-7.43 (m, 1H), 7.33-7.27 (m, 2H), 6.33/6.32 (2×s, 1H), 5.93/5.83 (2×dd, 1H), 3.22/3.20 (2×s, 3H), 3.09-3.00 (m, 1H), 2.68 (dd, 1H), 2.34-1.70 (m, 6H), 1.16-0.61 (m, 9H).

Example 26

4-{[2-(11'-Chloro-2',5'-dioxo-2',5',6',8'-tetrahydro-3'H-spiro[cyclopropane-1,7'-pyrido[3,4-e][3]benzazocine]-3'-yl)-3-(trans-4-methoxycyclohexyl)propanoyl]amino}-2-fluorobenzamide (Stereoisomer Mixture)

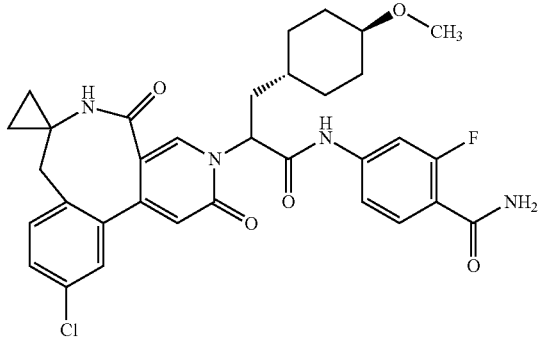 [SMILES: CO[C@H]1CC[C@H](CC(C(=O)Nc2ccc(C(N)=O)c(F)c2)n2cc3c(cc2=O)-c2cc(Cl)ccc2CC2(CC2)NC3=O)CC1]

According to General Method 7, 50.0 mg (103 µmol) of 2-(11'-chloro-2',5'-dioxo-2',5',6',8'-tetrahydro-3'H-spiro[cyclopropane-1,7'-pyrido[3,4-e][3]benzazocine]-3'-yl)-3-(trans-4-methoxycyclohexyl)propanoic acid (stereoisomer mixture), 15.9 mg (103 µmol) of 4-amino-2-fluorobenzamide, 10 mg (72 µmol) of Oxima and 16.0 µl (103 µmol) of DIC in 1 ml of dimethylformamide were reacted. The solvent was removed under reduced pressure and the residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 30.4 mg (47% of theory)

LC/MS [Method 1]: $R_t$=0.87 min, 0.88 min; MS (ESIpos): m/z=621 (M+H)$^+$ $^1$H-NMR (400 MHz, DMSO-$d_6$): δ [ppm]=10.92/10.85 (2×s, 1H), 8.17/8.10 (2×s, 1H), 7.87-7.27 (m, 9H), 6.34/6.33 (2×s, 1H), 5.91/5.79 (2×dd, 1H), 3.26-3.16 (m, 1H), 3.22/3.20 (2×s, 3H), 3.10-3.00 (m, 1H), 2.67 (dd, 1H), 2.34-1.71 (m, 6H), 1.16-0.60 (m, 9H).

Example 27

2-(11'-Chloro-2',5'-dioxo-2',5',6',8'-tetrahydro-3'H-spiro[cyclopropane-1,7'-pyrido[3,4-e][3]benzazocine]-3'-yl)-3-(trans-4-methoxycyclohexyl)-N-(2-oxo-2,3-dihydro-1H-benzimidazol-5-yl)propanamide (Stereoisomer Mixture)

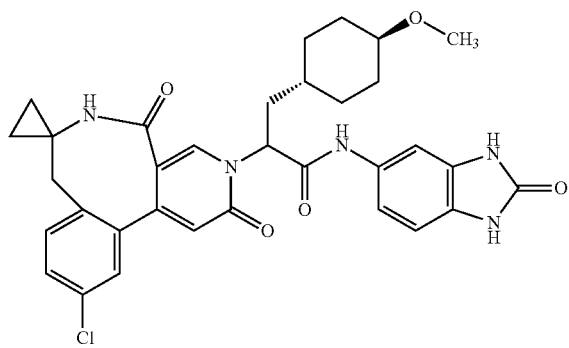 [SMILES: CO[C@H]1CC[C@H](CC(C(=O)Nc2ccc3[nH]c(=O)[nH]c3c2)n2cc3c(cc2=O)-c2cc(Cl)ccc2CC2(CC2)NC3=O)CC1]

According to General Method 7, 30 mg (62 µmol) of 2-(11'-chloro-2',5'-dioxo-2',5',6',8'-tetrahydro-3'H-spiro[cyclopropane-1,7'-pyrido[3,4-e][3]benzazocine]-3'-yl)-3-(trans-4-methoxycyclohexyl)propanoic acid (stereoisomer mixture), 9.2 mg (62 µmol) of 5-amino-1,3-dihydro-2H-benzimidazol-2-one, 6.2 mg (43 µmol) of Oxima and 9.6 µl (62 µmol) of DIC in 1 ml of dimethylformamide were reacted. The solvent was removed under reduced pressure and the residue was purified by means of preparative HPLC [column: Chromatorex C18, 10 µm, 125 mm×30 mm, eluent: acetonitrile/0.1% formic acid gradient (0 to 3 min 10% acetonitrile, to 35 min 90% acetonitrile and for a further 3 min 90% acetonitrile)]. Yield: 30.0 mg (78% of theory)

LC/MS [Method 1]: $R_t$=0.81 min, 0.84 min; MS (ESIpos): m/z=616 (M+H)$^+$ $^1$H-NMR (400 MHz, DMSO-d$_6$): δ [ppm]=10.60/10.55 (2×s, 1H), 10.51 (s, 1H), 10.39/10.37 (2×s, 1H), 8.15/8.8.08 (2×s, 1H), 7.88/7.68 (2×s, 1H), 7.47-7.26 (m, 4H), 7.10-7.02 (m, 1H), 6.88-6.81 (m, 1H), 6.32/6.31 (2×s, 1H), 5.87/5.81 (2×dd, 1H), 3.25-3.15 (m, 1H), 3.22/3.20 (2×s, 3H), 3.10-2.99 (m, 1H), 2.74-2.60 (m, 1H), 2.25-1.71 (m, 6H), 1.16-0.58 (m, 9H).

Example 28

4-{[2-(11'-Chloro-2',5'-dioxo-2',5',6',8'-tetrahydro-3'H-spiro[cyclopropane-1,7'-pyrido[3,4-e][3]benzazocine]-3'-yl)-3-phenylpropanoyl]amino}benzoic acid (Stereoisomer Mixture)

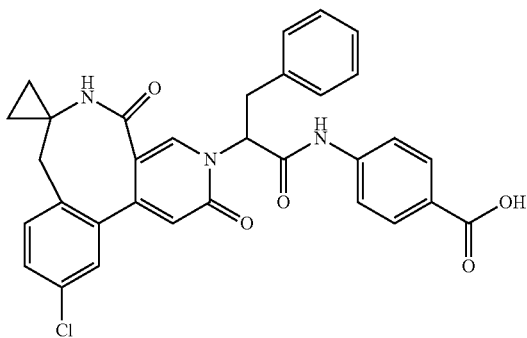 [SMILES: O=C(O)c1ccc(NC(=O)C(Cc2ccccc2)n2cc3c(cc2=O)-c2cc(Cl)ccc2CC2(CC2)NC3=O)cc1]

According to General Method 1, 88 mg (14 µmol) of tert-butyl 4-{[2-(11'-chloro-2',5'-dioxo-2',5',6',8'-tetrahydro-3'H-spiro[cyclopropane-1,7'-pyrido[3,4-e][3]benzazocine]-3'-yl)-3-phenylpropanoyl]amino}benzoate (stereoisomer mixture) were hydrolysed with trifluoroacetic acid. The crude product was purified by means of preparative RP-HPLC (Reprosil C18, water/acetonitrile gradient). Yield: 27 mg (33% of theory)

LC/MS [Method 2]: $R_t$=2.83 min/2.90 min; MS (ESIpos): m/z=568 (M+H)$^+$, $^1$H-NMR (400 MHz, DMSO-d$_6$): δ [ppm]=12.75 (br. s, 1H), 10.96/10.78 (2×s, 1H), 8.09/8.00 (2×s, 1H), 7.98-7.83 (m, 3H), 7.80-7.70 (m, 2H), 7.46-7.39 (m, 1H), 7.37-7.10 (m, 7H), 6.28/6.03 (2×dd, 1H), 6.22/6.18 (2×s, 1H), 3.64-3.46 (m, 2H), 3.20/3.03 (2×d, 1H), 2.62 (d, 0.4H), 0.97-0.83 (m, 1H), 0.76-0.56 (m, 2H), 0.36-0.21 (m, 1H).

Example 29

2-(11'-Chloro-2',5'-dioxo-2',5',6',8'-tetrahydro-3'H-spiro[cyclopropane-1,7'-pyrido[3,4-e][3]benzazocine]-3'-yl)-N-(2-oxo-2,3-dihydro-1H-benzimidazol-5-yl)-3-phenylpropanamide (Stereoisomer Mixture)

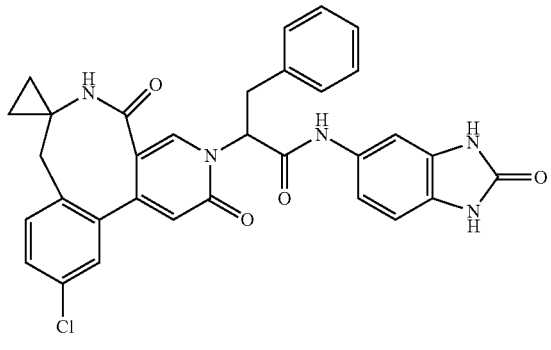 [SMILES: O=C1NC2(CC2)Cc2ccc(Cl)cc2-c2cc(=O)n(C(Cc3ccccc3)C(=O)Nc3ccc4[nH]c(=O)[nH]c4c3)cc21]

According to General Method 5, 30 mg (63% purity, 42 µmol) of 2-(11'-chloro-2',5'-dioxo-2',5',6',8'-tetrahydro-3'H-spiro[cyclopropane-1,7'-pyrido[3,4-e][3]benzazocine]-3'-yl)-3-phenylpropanoic acid (stereoisomer mixture) were reacted with 9 mg (63 µmol, 1.5 eq.) of 5-amino-1,3-dihydro-2H-benzimidazol-2-one. The crude product was purified by preparative RP-HPLC (Reprosil C18, water/acetonitrile gradient). Yield: 16 mg (64% of theory)

LC/MS [Method 11]: $R_t$=1.49 min/1.53 min; MS (ESIpos): m/z=580 (M+H)$^+$, $^1$H-NMR (400 MHz, DMSO-d$_6$): δ [ppm]=10.62/10.57/10.53/10.50/10.36 (6×s, 3H), 8.10/8.00/7.95/7.84 (4×s, 2H), 7.47-7.39 (m, 2H), 7.36-7.15 (m, 7H), 7.10/7.05 (2×dd, 1H), 6.88/6.87 (2×d, 1H), 6.22/6.02 (2×dd, 1H), 6.21/6.17 (2×s, 1H), 3.55-3.43 (m 2H), 3.20/3.03 (2×d, 1H), 2.62/2.54 (2×d, 1H), 0.96-0.84 (m, 1H), 0.75-0.56 (m, 1.5H), 0.38-0.22 (m, 1.5H).

Example 30

2-(11'-Chloro-2',5'-dioxo-2',5',6',8'-tetrahydro-3'H-spiro[cyclopropane-1,7'-pyrido[3,4-e][3]benzazocine]-3'-yl)-N-(2-methyl-2H-indazol-5-yl)-3-phenyl-propanamide (Stereoisomer Mixture)

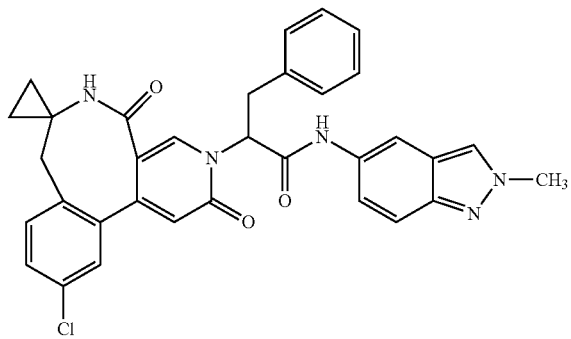 [SMILES: Cn1cc2cc(NC(=O)C(Cc3ccccc3)n3cc4c(cc3=O)-c3cc(Cl)ccc3CC3(CC3)NC4=O)ccc2n1]

According to General Method 5, 118 mg (63% purity, 0.17 mmol) of 2-(11'-chloro-2',5'-dioxo-2',5',6',8'-tetrahydro-3'H-spiro[cyclopropane-1,7'-pyrido[3,4-e][3]benzazocine]-3'-yl)-3-phenylpropanoic acid (stereoisomer mixture) were reacted with 37 mg (25 mmol, 1.5 eq.) of 2-methyl-2H-indazol-5-amine. The crude product was purified by means of preparative RP-HPLC (Reprosil C18, water/acetonitrile gradient). Yield: 33 mg (35% of theory)

LC/MS [Method 1]: $R_t$=0.93 min/0.95 min; MS (ESIpos): m/z=578 (M+H)$^+$, $^1$H-NMR (400 MHz, DMSO-d$_6$): δ [ppm]=10.59/10.43 (2×s, 1H), 8.28 (s, 1H), 8.17/8.09/8.02/7.95/7.86 (5×s, 3H), 7.61-7.55 (m, 1H), 7.46-7.40 (m, 1H), 7.38-7.10 (m, 8H), 6.28/6.06 (2×dd, 1H), 6.22/6.18 (2×s, 1H), 4.14 (s, 3H), 3.59-3.45 (m, 2H), 3.20/3.04 (2×d, 1H), 2.62/2.54 (2×d, 1H), 0.97-0.85 (m, 1H), 0.77-0.57 (m, 2H), 0.39-0.23 (m, 1H).

Example 31

2-[11-Chloro-7-(fluoromethyl)-2,5-dioxo-5,6,7,8-tetrahydropyrido[3,4-e][3]benzazocin-3(2H)-yl]-4-methoxy-N-(2-methyl-2H-indazol-5-yl)butanamide (Stereoisomer Mixture)

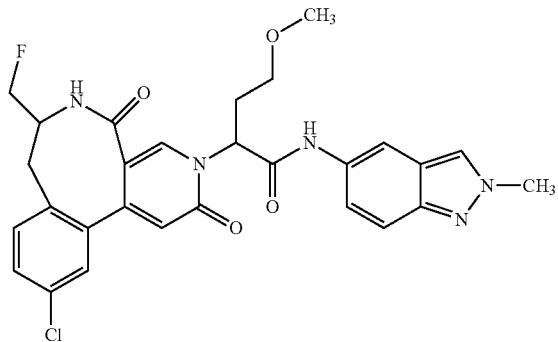 [SMILES: COCCC(C(=O)Nc1ccc2nn(C)cc2c1)n1cc2c(cc1=O)-c1cc(Cl)ccc1CC(CF)NC2=O]

According to General Method 5, 10 mg (24 µmol) of 2-[11-chloro-7-(fluoromethyl)-2,5-dioxo-5,6,7,8-tetrahydropyrido[3,4-e][3]benzazocin-3(2H)-yl]-4-methoxybutanoic acid (stereoisomer mixture) were reacted with 6.3 mg (43 µmol, 1.8 eq.) of 2-methyl-2H-indazol-5-amine. The crude product was purified by preparative HPLC (water/acetonitrile/0.1% formic acid gradient). Yield: 5 mg (38% of theory)

LC/MS [Method 1]: $R_t$=0.76 min; MS (ESIpos): m/z=552 (M+H)$^+$, $^1$H-NMR (400 MHz, DMSO-d$_6$): δ [ppm]=10.50-10.31 (m, 1H), 8.28-8.21 (m, 1H), 8.15-8.06 (m, 1H), 8.01-7.70 (m, 2H), 7.59-7.39 (m, 3H), 7.33-7.21 (m, 2H), 6.40-6.21 (m, 1H), 5.82-5.66 (m, 1H), 4.57-4.28 (m, 2H), 4.13 (s, 3H), 4.12-3.98 and 3.68-3.50 (2×m, 1H), 3.46-3.37 (m, 1H), 3.24-3.16 (m, 4H), 3.13-2.94 (m, 1H), 2.73-2.57 (m, 1H), 2.44-2.24 (m, 3H).

Example 32

4-({2-[11-Chloro-7-(fluoromethyl)-2,5-dioxo-5,6,7,8-tetrahydropyrido[3,4-e][3]benzazocin-3(2H)-yl]-4-methoxybutanoyl}amino)-2-fluorobenzamide (Stereoisomer Mixture)

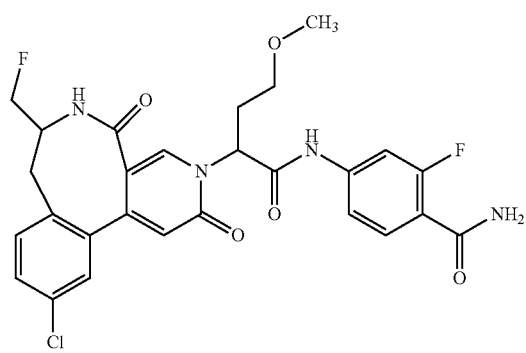 [SMILES: COCCC(C(=O)Nc1ccc(C(N)=O)c(F)c1)n1cc2c(cc1=O)-c1cc(Cl)ccc1CC(CF)NC2=O]

According to General Method 5, 15 mg (35 µmol) of 2-[11-chloro-7-(fluoromethyl)-2,5-dioxo-5,6,7,8-tetrahydropyrido[3,4-e][3]benzazocin-3(2H)-yl]-4-methoxybutanoic acid (stereoisomer mixture) were reacted with 8.5 mg (53 µmol, 1.5 eq.) of 4-amino-2-fluorobenzamide. The crude product was purified by preparative HPLC (water/acetonitrile/0.1% formic acid gradient). Yield: 7 mg (35% of theory)

LC/MS [Method 1]: $R_t$=0.73 min; MS (ESIpos): m/z=559 (M+H)$^+$, $^1$H-NMR (400 MHz, DMSO-d$_6$): δ [ppm]=10.79-10.69 (m, 1H), 8.02-7.22 (m, 10H), 6.39-6.23 (m, 1H), 5.77-5.58 (m, 1H), 4.56-4.27 (m, 2H), 4.14-3.96 and 3.69-3.52 (2×m, 1H), 3.45-3.36 (m, 1H), 3.23-3.15 (m, 3H), 3.14-2.95 (m, 1H), 2.72-2.57 (m, 1H), 2.46-2.26 (m, 2H).

Example 33

4-({2-[11-Chloro-7-(fluoromethyl)-2,5-dioxo-5,6,7,8-tetrahydropyrido[3,4-e][3]benzazocin-3(2H)-yl]-4-methoxybutanoyl}amino)benzoic acid (Stereoisomer Mixture)

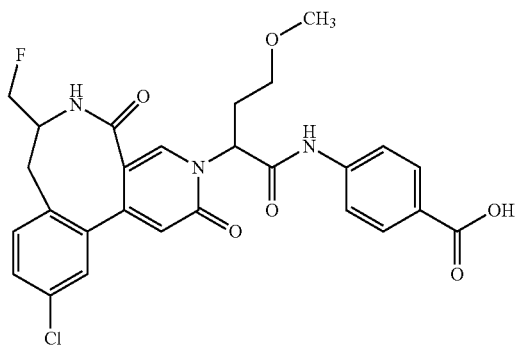 [SMILES: COCCC(C(=O)Nc1ccc(C(=O)O)cc1)n1cc2c(cc1=O)-c1cc(Cl)ccc1CC(CF)NC2=O]

According to General Method 2, 19 mg (34 μmol) of methyl 4-({2-[11-chloro-7-(fluoromethyl)-2,5-dioxo-5,6,7,8-tetrahydropyrido[3,4-e][3]benzazocin-3(2H)-yl]-4-methoxybutanoyl}amino)benzoate (stereoisomer mixture) were reacted. The crude product was purified by preparative HPLC (water/acetonitrile/0.1% formic acid gradient). Yield: 8 mg (43% of theory)

LC/MS [Method 1]: $R_t$=0.76 min; MS (ESIpos): m/z=542 $(M+H)^+$, $^1$H-NMR (400 MHz, DMSO-$d_6$): δ [ppm]=12.77 (br. s., 1H), 10.78-10.62 (m, 1H), 8.00-7.69 (m, 6H), 7.53-7.41 (m, 2H), 7.34-7.19 (m, 1H), 6.39-6.21 (m, 1H), 5.81-5.69 (m, 1H), 4.56-4.28 (m, 2H), 4.13-3.96 and 3.72-3.50 (2×m, 1H), 3.53-3.37 (m, 2H), 3.23-2.94 (m, 5H), 2.72-2.57 (m, 1H), 2.44- 2.24 (m, 2H).

B) ASSESSMENT OF PHYSIOLOGICAL EFFICACY

The suitability of the compounds according to the invention for treating thromboembolic disorders can be demonstrated in the following assay systems:

a) Test Descriptions (In Vitro)

a.1) Measurement of FXIa Inhibition

The factor XIa inhibition of the substances according to the invention is determined using a biochemical test system which utilizes the reaction of a peptidic factor XIa substrate to determine the enzymatic activity of human factor XIa. Here, factor XIa cleaves from the peptic factor XIa substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 μM to 0.0078 μM; resulting final concentrations in the test: 50 μM to 0.00013 μM). 1 μl of the diluted substance solutions is placed into each of the wells of white microtitre plates from Greiner (384 wells). 20 μl of assay buffer (50 mM of Tris/HCl pH 7.4; 100 mM of sodium chloride; 5 mM of calcium chloride; 0.1% of bovine serum albumin) and 20 μl of factor XIa from Kordia (0.45 nM in assay buffer) are then added successively. After 15 min of incubation, the enzyme reaction is started by addition of 20 μl of the factor XIa substrate Boc-Glu(OBzl)-Ala-Arg-AMC dissolved in assay buffer (10 μM in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and $IC_{50}$ values are calculated from the concentration/activity relationships. Activity data from this test are listed in Table A below:

TABLE A

| Example No. | $IC_{50}$ [nM] | Example No. | $IC_{50}$ [nM] |
|---|---|---|---|
| 1 | 420 | 2 | 280 |
| 3 | 180 | 4 | 720 |
| 5 | 350 | 6 | 28 |
| 7 | 44 | 8 | 36 |
| 9 | 140 | 10 | 7.7 |
| 11 | 16 | 12 | 1.9 |
| 13 | 27 | 14 | 18 |
| 15 | 8.2 | 16 | 11 |
| 17 | 44 | 18 | 21 |
| 19 | 8.4 | 20 | 47 |
| 21 | 34 | 22 | 4.0 |
| 23 | 100 | 24 | 35 |
| 25 | 2.5 | 26 | 34 |
| 27 | 18 | 28 | 1.8 |
| 29 | 4.5 | 30 | 4.5 |
| 31 | 2.8 | 32 | 5.3 |
| 33 | 1.2 | | | a.2) Determination of the Selectivity

To demonstrate the selectivity of the substances with respect to FXIa inhibition, the test substances are examined for their inhibition of other human serine proteases, such as factor Xa, trypsin and plasmin. To determine the enzymatic activity of factor Xa (1.3 nmol/l from Kordia), trypsin (83 mU/ml from Sigma) and plasmin (0.1 μg/ml from Kordia), these enzymes are dissolved (50 mmol/l of Tris buffer [C,C,C-tris(hydroxymethyl)aminomethane], 100 mmol/l of NaCl, 0.1% BSA [bovine serum albumin], 5 mmol/l of calcium chloride, pH 7.4) and incubated for 15 min with test substance in various concentrations in dimethyl sulphoxide and also with dimethyl sulphoxide without test substance. The enzymatic reaction is then started by addition of the appropriate substrates (5 μmol/l of Boc-Ile-Glu-Gly-Arg-AMC from Bachem for factor Xa and trypsin, 5 50 μmol/l of MeOSuc-Ala-Phe-Lys-AMC from Bachem for plasmin). After an incubation time of 30 min at 22° C., fluorescence is measured (excitation: 360 nm, emission: 460 nm). The measured emissions of the test mixtures with test substance are compared to the control mixtures without test substance (only dimethyl sulphoxide instead of test substance in dimethyl sulphoxide) and $IC_{50}$ values are calculated from the concentration/activity relationships.

a.3) Thrombin Generation Assay (Thrombogram)

The effect of the test substances on the thrombogram (thrombin generation assay according to Hemker) is determined in vitro in human plasma (Octaplas® from Octapharma).

In the thrombin generation assay according to Hemker, the activity of thrombin in coagulating plasma is determined by measuring the fluorescent cleavage products of the substrate I-1140 (Z-Gly-Gly-Arg-AMC, Bachem). The reactions are carried out in the presence of varying concentrations of test substance or the corresponding solvent. To start the reaction, reagents from Thrombinoscope (30 pM or 0.1 pM recombinant tissue factor, 24 μM phospholipids in HEPES) are used. In addition, a thrombin calibrator from Thrombinoscope is used whose amidolytic activity is required for calculating the thrombin activity in a sample containing an unknown amount of thrombin. The test is carried out according to the manufacturer's instructions (Thrombinoscope BV): 4 µl of test substance or of the solvent, 76 µl of plasma and 20 µl of PPP reagent or thrombin calibrator are incubated at 37° C. for 5 min. After addition of 20 µl of 2.5 mM thrombin substrate in 20 mM Hepes, 60 mg/ml of BSA, 102 mM of calcium chloride, the thrombin generation is measured every 20 s over a period of 120 min. Measurement is carried out using a fluorometer (Fluoroskan Ascent) from Thermo Electron fitted with a 390/460 nm filter pair and a dispenser.

Using the Thrombinoscope software, the thrombogram is calculated and represented graphically. The following parameters are calculated: lag time, time to peak, peak, ETP (endogenous thrombin potential) and start tail.

a.4) Determination of Anticoagulatory Activity

The anticoagulatory activity of the test substances is determined in vitro in human plasma and rat plasma. To this end, blood is drawn off in a mixing ratio of sodium citrate/blood of 1:9 using a 0.11 molar sodium citrate solution as receiver. Immediately after the blood has been drawn off, it is mixed thoroughly and centrifuged at about 4000 g for 15 minutes. The supernatant is pipetted off.

The prothrombin time (PT, synonyms: thromboplastin time, quick test) is determined in the presence of varying concentrations of test substance or the corresponding solvent using a commercial test kit (Neoplastin® from Boehringer Mannheim or Hemoliance® RecombiPlastin from Instrumentation Laboratory). The test compounds are incubated with the plasma at 37° C. for 3 minutes. Coagulation is then started by addition of thromboplastin, and the time when coagulation occurs is determined. The concentration of test substance which effects a doubling of the prothrombin time is determined.

The activated partial thromboplastin time (APTT) is determined in the presence of varying concentrations of test substance or the corresponding solvent using a commercial test kit (PTT reagent from Roche). The test compounds are incubated with the plasma and the PTT reagent (cephalin, kaolin) at 37° C. for 3 minutes. Coagulation is then started by addition of 25 mM calcium chloride, and the time when coagulation occurs is determined. The concentration of test substance which effects an extension by 50% or a doubling of the APTT is determined.

a.5) Determination of the Plasma Kallikrein Activity

To determine the plasma kallikrein inhibition of the substances according to the invention, a biochemical test system is used which utilizes the reaction of a peptidic plasma kallikrein substrate to determine the enzymatic activity of human plasma kallikrein. Here, plasma kallikrein cleaves from the peptic plasma kallikrein substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 µM to 0.0078 µM; resulting final concentrations in the test: 50 µM to 0.00013 µM). 1 µl of the diluted substance solutions is placed into each of the wells of white microtitre plates from Greiner (384 wells). 20 µl of assay buffer (50 mM Tris/HCl pH 7.4; 100 mM sodium chloride solution; 5 mM of calcium chloride solution; 0.1% of bovine serum albumin) and 20 µl of plasma kallikrein from Kordia (0.6 nM in assay buffer) are then added successively. After 15 min of incubation, the enzyme reaction is started by addition of 20 µl of the substrate H-Pro-Phe-Arg-AMC dissolved in assay buffer (10 µM in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and $IC_{50}$ values are calculated from the concentration/activity relationships.

TABLE B

| Example No. | $IC_{50}$ [nM] | Example No. | $IC_{50}$ [nM] |
|---|---|---|---|
| 1 | >10000 | 2 | 4900 |
| 3 | >50000 | 4 | 18000 |
| 5 | 8300 | 6 | 1900 |
| 7 | 3300 | 8 | 680 |
| 9 | 3800 | 10 | 2100 |
| 11 | 1700 | 12 | 390 |
| 13 | 780 | 14 | 230 |
| 15 | 240 | 16 | 210 |
| 17 | 1200 | 18 | 330 |
| 19 | 230 | 20 | 4500 |
| 21 | 910 | 22 | 340 |
| 23 | 3900 | 24 | 800 |
| 25 | 370 | 26 | 740 |
| 27 | 250 | 28 | 55 |
| 29 | 42 | 30 | 45 |
| 31 | 42 | 32 | 100 |
| 33 | 97 | | | a.6) Determination of Endothelium Integrity

The activity of the compounds according to the invention is characterized by means of an in vitro permeability assay on "human umbilical venous cells" (HUVEC). Using the EOS apparatus (EC IS: Electric Cell-substrate Impedance Sensing; Applied Biophysics Inc; Troy, N.Y.), it is possible to measure continuously variations in the transendothelial electrical resistance (TEER) across an endothelial cell monolayer plated over gold electrodes. HUVECs are sown on a 96-well sensor electrode plate (96W1 E, Ibidi GmbH, Martinsried, Germany). Hyperpermeability of the confluent cell monolayer formed is induced by stimulation with kininogen, prekallikrein and factor XII (100 nM each). The compounds according to the invention are added prior to the addition of the substances indicated above. The customary concentrations of the compounds are $1\times10^{-10}$ to $1\times10^{-6}$ M.

a.7) Determination of the In Vitro Permeability of Endothelial Cells

In a further hyperpermeability model, the activity of the substances on the modulation of macromolecular permeability is determined. HUVECs are sown on a fibronectin-coated Transwell filter membrane (24-well plates, 6.5 mm insert with 0.4 µM polycarbonate membrane; Costar #3413). The filter membrane separates the upper from the lower cell culture space, with the confluent endothelial cell layer on the floor of the upper cell culture space. 250 g/ml of 40 kDa FITC dextan (Invitrogen, D1844) are added to the medium of the upper chamber. Hyperpermeability of the monolayer is induced by stimulation with kininogen, prekallikrein and factor XII (100 nM each). Every 30 min, medium samples are removed from the lower chamber and relative fluorescence as a parameter for changes in macromolecular permeability as a function of time is determined using a fluorimeter. The compounds according to the invention are added prior to the addition of the substances indicated above. The customary concentrations of the compounds are $1\times10^{-10}$ to $1\times10^{-6}$ M.

b) Determination of Antithrombotic Activity (In Vivo)
b.1) Arterial Thrombosis Model (Iron(II) Chloride-Induced Thrombosis) in Combination with Ear Bleeding Time in Rabbits The antithrombotic activity of the FXIa inhibitors is tested in an arterial thrombosis model. Thrombus formation is triggered here by causing chemical injury to a region in the carotid artery in rabbits. Simultaneously, the ear bleeding time is determined.

Male rabbits (Crl:KBL (NZW)BR, Charles River) receiving a normal diet and having a body weight of 2.2-2.5 kg are anaesthetized by intramuscular administration of xylazine and ketamine (Rompun, Bayer, 5 mg/kg and Ketavet, Pharmacia & Upjohn GmbH, 40 mg/kg body weight). Anaesthesia is furthermore maintained by intravenous administration of the same preparations (bolus: continuous infusion) via the right auricular vein.

The right carotid artery is exposed and the vessel injury is then caused by wrapping a piece of filter paper (10 mm×10 mm) on a Parafilm® strip (25 mm×12 mm) around the carotid artery without disturbing the blood flow. The filter paper contains 100 μL of a 13% strength solution of iron(II) chloride (Sigma) in water. After 5 min, the filter paper is removed and the vessel is rinsed twice with aqueous 0.9% strength sodium chloride solution. 30 min after the injury the injured region of the carotid artery is extracted surgically and any thrombotic material is removed and weighed.

The test substances are administered either intravenously to the anaesthetized animals via the femoral vein or orally to the awake animals via gavage, in each case 5 min and 2 h, respectively, before the injury.

Ear bleeding time is determined 2 min after injury to the carotid artery. To this end, the left ear is shaved and a defined 3-mm-long incision (blade Art. Number 10-150-10, Martin, Tuttlingen, Germany) is made parallel to the longitudinal axis of the ear. Care is taken here not to damage any visible vessels. Any blood that extravasates is taken up in 15 second intervals using accurately weighed filter paper pieces, without touching the wound directly. Bleeding time is calculated as the time from making the incision to the point in time where no more blood can be detected on the filter paper. The volume of the extravasated blood is calculated after weighing of the filter paper pieces.

c) Determination of the Effect on Extravasation/Oedema Formation and/or Neovascularization in the Eye (In Vivo)
c.1) Test of the Efficacy of Substances in the Laser-Induced Choroidal Neovascularization Model This study serves to investigate the efficacy of a test substance on reduction of extravasation/oedema formation and/or choroidal neovascularization in the rat model of laser-induced choroidal neovascularization.

To this end, pigmented rats of the Brown-Norway strain not showing any signs of ophthalmic disorders are selected and randomized into treatment groups. On day 0, the animals are anaesthetized by intraperitoneal injection (15 mg/kg xylazine and 80 mg/kg ketamine). Following instillation of a drop of a 0.5% strength tropicamide solution to dilate the pupils, choroidal neovascularization is triggered on six defined locations around the optical nerve using a 532 nm argon laser photocoagulator (diameter 50-75 μm, intensity 150 mW, duration 100 ms). The test substance and the appropriate vehicle (e.g. PBS, isotonic saline) are administered either systemically by the oral or intraperitonal route, or topically to the eye by repeated administration as eye drops or intravitreal injection. The body weight of all the animals is determined before the start of the study, and then daily during the study.

On day 21, an angiography is carried out using a fluorescence fundus camera (e.g. Kowe, HRA). Under anaesthesia and after another pupil dilation, a 10% strength sodium fluorescein dye is injected subcutaneously (s.c.). 2-10 min later, pictures of the eye background are taken. The degree of extravasation/the oedema, represented by the leakage of fluorescein, is assessed by two to three blinded observers and classified into degrees of severity from 0 (no extravasation) to 3 (strong colouration exceeding the actual lesion).

The animals are sacrificed on day 23, after which the eyes are removed and fixated in 4% strength paraformaldehyde solution for one hour at room temperature. After one washing, the retina is carefully peeled off and the sclera-choroidea complex is stained using an FITC isolectin B4 antibody and then applied flat to a microscope slide. The preparations obtained in this manner are evaluated using a fluorescence microscope (Apotom, Zeiss) at an excitation wavelength of 488 nm. The area or volume of the choroidal neovascularization (in $\mu m^2$ and $\mu m^3$, respectively) is calculated by morphometric analysis using Axiovision 4.6 software.

c.2) Test of the Efficacy of Substances in the Oxygen-Induced Retinopathy Model

It has been shown that oxygen-induced retinopathy is a useful animal model for the study of pathological retinal angiogenesis. This model is based on the observation that hyperoxia during early postnatal development in the retina causes arrest or delay of the growth of normal retinal blood vessels. When, after a 7-day hyperoxia phase, the animals are returned to normoxic room air, this is equivalent to relative hypoxia since the retina is missing the normal vessels which are required to ensure adequate supply of the neural tissue under normoxic conditions. The ischaemic situation caused in this manner results in an abnormal neovascularization which has some similarities with pathophysiological neovascularization in eye disorders such as wet AMD. In addition, the neovascularization caused is highly reproducible, quantifiable and an important parameter for examining the disease mechanisms and possible treatments for various forms of retinal disorders.

The aim of this study is to examine the efficacy of daily systemically administered doses of the test compound on the growth of retinal vessels in the oxygen-induced retinopathy model. Neonates of C57Bl/6 mice and their mothers are exposed to hyperoxia (70% oxygen) on postnatal day 7 (PD7) for 5 days. From PD12, the mice are kept under normoxic conditions (room air, 21% oxygen) until PD17. From day 12 to day 17, the mice are treated daily with the test substance or the corresponding vehicle. On day 17, all mice are anaesthetized with isoflurane and then sacrificed by cervical fracture. The eyes are removed and fixated in 4% formalin. After washing in phosphate-buffered saline, the retina is excised, a flat preparation thereof is produced and this is stained with isolectin B4 antibody. Quantification of neovascularization is carried out using a Zeiss ApoTome.

C) WORKING EXAMPLES FOR PHARMACEUTICAL COMPOSITIONS

The substances according to the invention can be converted to pharmaceutical preparations as follows:
Tablet:
Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.

Production:

The mixture of the compound of Example 1, lactose and starch is granulated with a 5% strength solution (m/m) of the PVP in water. After drying, the granules are mixed with the magnesium stearate for 5 min. This mixture is compressed using a conventional tableting press (see above for format of the tablet).

Oral Suspension:

Composition:

1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the compound of the invention.

Production:

The Rhodigel is suspended in ethanol, and the compound of Example 1 is added to the suspension. The water is added while stirring. The mixture is stirred for about 6 h until swelling of the Rhodigel is complete.

Solution or Suspension for Topical Administration to the Eye (Eye Drops):

A sterile pharmaceutical preparation for topical administration to the eye can be prepared by reconstituting a lyophilisate of the inventive compound in sterile saline. Suitable preservatives for such a solution or suspension are, for example, benzalkonium chloride, thiomersal or phenylmercury nitrate in a concentration range of from 0.001 to 1 percent by weight.

Solution or Suspension for Topical Administration to the Eye (Eye Drops):

A sterile pharmaceutical preparation for topical administration to the eye can be prepared by reconstituting a lyophilisate of the inventive compound in sterile saline. Suitable preservatives for such a solution or suspension are, for example, benzalkonium chloride, thiomersal or phenylmercury nitrate in a concentration range of from 0.001 to 1 percent by weight.

The invention claimed is:

1. A compound of formula (I)

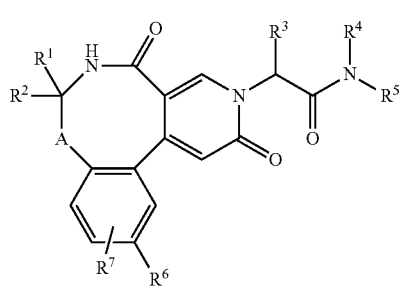

(I)

in which

A is a bond or —$CH_2$—, $R^1$ is hydrogen or methyl,
where methyl may be substituted by a fluorine substituent, $R^2$ is hydrogen or methyl,
or $R^1$ and $R^2$ together with the carbon atom to which they are bonded form a cyclopropyl ring, $R^3$ is hydrogen, $C_1$-$C_5$-alkyl, $C_1$-$C_4$-alkoxy, difluoromethyl, trifluoromethyl, 1,1-difluoroethyl, 3,3,3-trifluoro-2-hydroxyprop-1-yl, 3,3,3-trifluoro-2-methoxyprop-1-yl, 3,3,3-trifluoro-2-ethoxyprop-1-yl, prop-2-yn-1-yl, cyclopropyloxy or cyclobutyloxy, where alkyl may be substituted by a substituent selected from the group consisting of fluorine, cyano, hydroxyl, difluoromethyl, trifluoromethyl, methoxy, ethoxy, difluoromethoxy, trifluoromethoxy, $C_3$-$C_6$-cycloalkyl, 4- to 6-membered oxoheterocyclyl, 1,4-dioxanyl, oxazolyl, phenyl and pyridyl, in which cycloalkyl may be substituted by 1 to 2 substituents selected independently from the group consisting of fluorine, hydroxyl, methyl, ethyl, methoxy, ethoxy, difluoromethyl, trifluoromethyl, difluoromethoxy and trifluoromethoxy, and in which the 4- to 6-membered oxoheterocyclyl is a monocyclic saturated ring having 3-5 carbons and an oxygen, $R^4$ is hydrogen, $R^5$ is a group of the formula

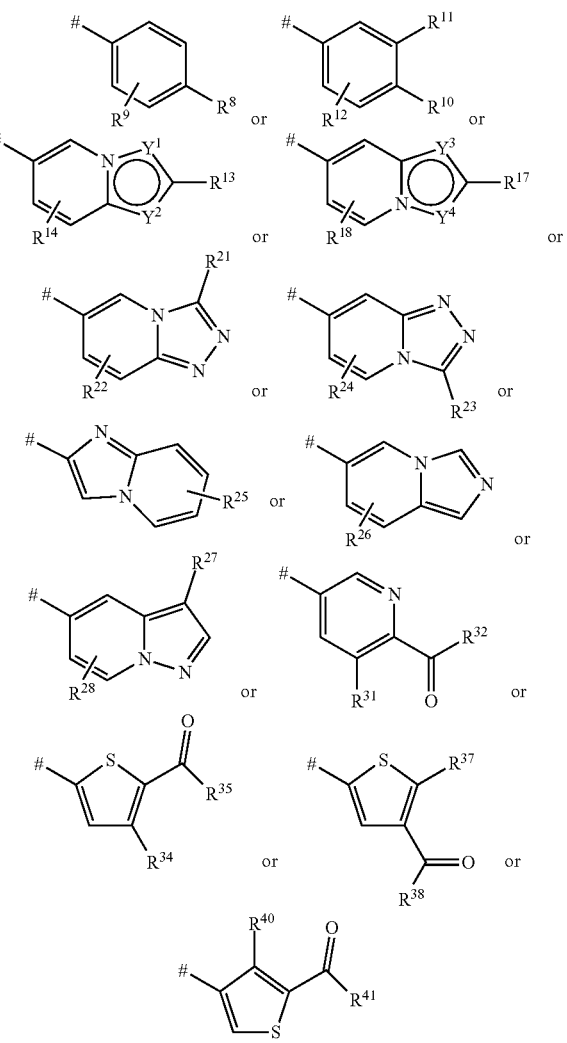

where # is the attachment point to the nitrogen atom, $R^8$ is carboxyl, aminocarbonyl or 5-membered heterocyclyl,
where the heterocyclyl is a monocyclic saturated, partly saturated or aromatic ring having 1, 2, 3 or 4 heteroatoms selected independently from the group consisting of sulfur, oxygen and nitrogen, and where the heterocyclyl may be substituted by 1 to 2 substituents selected independently from the group consisting of oxo, hydroxyl, thioxo, sulphanyl, methyl, difluoromethyl, trifluoromethyl, 2-carboxyl-1,1,2,2-tetrafluoroethyl and 2-methoxycarbonyl-1,1,2,2-tetrafluoroethyl, in which methyl may be substituted by a methoxy substituent, $R^9$ is hydrogen, chlorine, fluorine or methyl, $R^{10}$ and $R^{11}$ together with the carbon atoms to which they are bonded form a 5-membered heterocycle, where the heterocycle is a monocyclic saturated, partly saturated or aromatic ring having 1 or 2 heteroatoms selected independently from the group consisting of sulfur, oxygen and nitrogen, and where the heterocycle may be substituted by 1 to 2 substituents selected independently from the group consisting of oxo, chlorine, hydroxyl, carboxyl, methyl, difluoromethyl, trifluoromethyl, 1,1,2,2,2-pentafluoroethyl, 2-carboxyl-1,1,2,2-tetrafluoroethyl and 2-methoxycarbonyl-1,1,2,2-tetrafluoroethyl, $R^{12}$ is hydrogen, chlorine, fluorine, methyl or methoxy, $Y^1$ is a nitrogen atom or $C—R^{15}$ in which $R^{15}$ is hydrogen, chlorine, hydroxyl, methoxy or $C_1$-$C_3$ alkoxycarbonyl, $Y^2$ is a nitrogen atom or $C—R^{16}$ in which $R^{16}$ is hydrogen, chlorine, hydroxyl or methoxy, $R^{13}$ is hydrogen, carboxyl, carboxylmethyl or phenyl, where phenyl may be substituted by 1 to 2 fluorine substituents, $R^{14}$ is hydrogen, chlorine, fluorine or methyl, $Y^3$ is a nitrogen atom or $C—R^{19}$ in which $R^{19}$ is hydrogen, chlorine, hydroxyl or methoxy, $Y^4$ is a nitrogen atom or $C—R^{20}$ in which $R^{20}$ is hydrogen, chlorine, hydroxyl or methoxy, $R^{17}$ is hydrogen, carboxyl, carboxylmethyl, $C_1$-$C_3$-alkoxycarbonyl or aminocarbonyl, $R^{18}$ is hydrogen, chlorine, fluorine or methyl, $R^{21}$ is hydrogen, chlorine, hydroxy, $C_1$-$C_4$-alkyl, methoxy, $C_1$-$C_3$-alkylaminomethyl or morpholinylmethyl, $R^{22}$ is hydrogen, chlorine, fluorine or methyl, $R^{23}$ is hydrogen, chlorine, hydroxyl or methoxy, $R^{24}$ is hydrogen, chlorine, fluorine or methyl, $R^{25}$ is hydrogen, carboxyl or carboxylmethyl, $R^{26}$ is hydrogen, chlorine, fluorine or methyl, $R^{27}$ is carboxyl, aminocarbonyl, $C_1$-$C_3$-alkoxycarbonyl or $C_1$-$C_3$-alkylaminocarbonyl, where alkylaminocarbonyl may be substituted by a substituent selected from the group consisting of hydroxyl, trifluoromethyl, methoxy and trifluoromethoxy, $R^{28}$ is hydrogen, chlorine, fluorine or methyl, $R^{31}$ is hydrogen or fluorine, $R^{32}$ is hydroxyl or $—NHR^{33}$, in which $R^{33}$ is hydrogen, methyl or ethyl, $R^{34}$ is hydrogen or fluorine, $R^{35}$ is hydroxyl or $—NHR^{36}$, in which $R^{36}$ is hydrogen, methyl or ethyl, $R^{37}$ is hydrogen or fluorine, $R^{38}$ is hydroxyl or $—NHR^{39}$, in which $R^{39}$ is hydrogen, methyl or ethyl, $R^{40}$ is hydrogen or fluorine, $R^{41}$ is hydroxyl or $—NHR^{42}$, in which $R^{42}$ is hydrogen, methyl or ethyl, $R^6$ is bromine, chlorine, fluorine, methyl, difluoromethyl, trifluoromethyl, methoxy, difluoromethoxy or trifluoromethoxy, $R^7$ is hydrogen, chlorine or fluorine, or a pharmaceutically acceptable salt thereof.

2. The compound according to claim 1, wherein

A is a bond or $—CH_2—$, $R^1$ is hydrogen or methyl, $R^2$ is hydrogen or methyl, or $R^1$ and $R^2$ together with the carbon atom to which they are bonded form a cyclopropyl ring, $R^3$ is hydrogen, methyl, ethyl, n-propyl, 2-methylprop-1-yl, n-butyl or ethoxy, where methyl may be substituted by a substituent selected from the group consisting of difluoromethyl, trifluoromethyl, cyclopropyl, cyclobutyl, cyclohexyl, oxetanyl, tetrahydrofuranyl, tetrahydro-2H-pyranyl and 1,4-dioxanyl, where cyclopropyl, cyclobutyl, cyclohexyl and oxetanyl may be substituted by 1 to 2 substituents selected independently from the group consisting of fluorine, hydroxyl, methyl, ethyl and methoxy, and where ethyl, n-propyl and n-butyl may be substituted by a substituent selected from the group consisting of fluorine, methoxy and trifluoromethoxy, $R^4$ is hydrogen, $R^5$ is a group of the formula

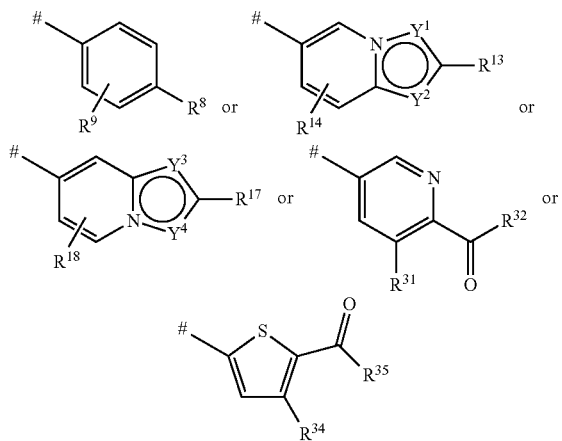

where # is the attachment point to the nitrogen atom, $R^8$ is carboxyl, aminocarbonyl, oxazolyl, oxadiazolyl, thiadiazolyl, pyrazolyl, imidazolyl, triazolyl, tetrazolyl or dihydrooxazolyl, where oxazolyl, oxadiazolyl, thiadiazolyl, pyrazolyl, imidazolyl, triazolyl and dihydrooxazolyl may be substituted by 1 to 2 substituents selected independently from the group consisting of oxo, hydroxyl, thioxo, sulphanyl, methyl, trifluoromethyl and 2-carboxyl-1,1,2,2-tetrafluoroethyl,
in which methyl may be substituted by a methoxy substituent,
$R^9$ is hydrogen, chlorine, fluorine or methyl,
$Y^1$ is a nitrogen atom or C—$R^{15}$
in which
$R^{15}$ is hydrogen, chlorine, hydroxyl or methoxy,
$Y^2$ is a nitrogen atom or C—$R^{16}$
in which
$R^{16}$ is hydrogen, chlorine, hydroxyl or methoxy,
$R^{13}$ is hydrogen or carboxyl,
$R^{14}$ is hydrogen or fluorine,
$Y^3$ is a nitrogen atom or C—$R^{19}$
in which
$R^{19}$ is hydrogen, chlorine, hydroxyl or methoxy,
$Y^4$ is a nitrogen atom or C—$R^{20}$
in which
$R^{20}$ is hydrogen, chlorine, hydroxyl or methoxy,
$R^{17}$ is hydrogen or carboxyl,
$R^{18}$ is hydrogen or fluorine,
$R^{31}$ is hydrogen,
$R^{32}$ is hydroxyl or —$NHR^{33}$,
in which
$R^{33}$ is hydrogen,
$R^{34}$ is hydrogen,
$R^{35}$ is hydroxyl,
or
$R^5$ is 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl, 1H-indazol-5-yl or 2H-indazol-5-yl,
where the 5-membered heterocycle in 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl, 1H-indazol-5-yl and 2H-indazol-5-yl may be substituted by 1 to 2 substituents independently selected from the group consisting of oxo, chlorine, carboxyl, methyl and trifluoromethyl,
and
where the benzyl ring in 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl and 1H-indazol-5-yl may be substituted by a substituent selected from the group consisting of fluorine and methoxy,
$R^6$ is chlorine,
$R^7$ is hydrogen,
or a pharmaceutically acceptable salt thereof.

3. The compound according to claim 1, wherein
A is a bond or —$CH_2$—,
$R^1$ is hydrogen,
$R^2$ is hydrogen,
or
$R^1$ and $R^2$ together with the carbon atom to which they are bonded form a cyclopropyl ring,
$R^3$ is hydrogen, ethyl or 2-methylprop-1-yl,
where ethyl may be substituted by a methoxy substituent,
$R^4$ is hydrogen,
$R^5$ is a group of the formula

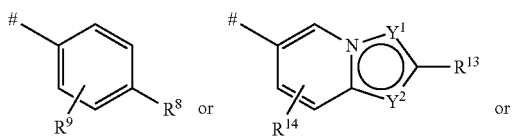

or

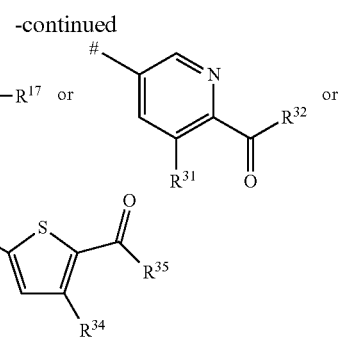

where # is the attachment point to the nitrogen atom,
$R^8$ is carboxyl, aminocarbonyl or oxadiazolyl,
where oxadiazolyl may be substituted by an oxo substituent,
$R^9$ is hydrogen or fluorine,
$Y^1$ is C—$R^{15}$,
in which
$R^{15}$ is hydrogen,
$Y^2$ is a nitrogen atom,
$R^{13}$ is hydrogen,
$R^{14}$ is hydrogen,
$Y^3$ is C—$R^{19}$,
in which
$R^{19}$ is hydrogen,
$Y^4$ is a nitrogen atom,
$R^{17}$ is hydrogen,
$R^{18}$ is hydrogen,
$R^{31}$ is hydrogen,
$R^{32}$ is hydroxyl or —$NHR^{33}$,
in which
$R^{33}$ is hydrogen,
$R^{34}$ is hydrogen,
$R^{35}$ is hydroxyl,
or
$R^5$ is 2,3-dihydro-1H-indazol-6-yl, 2,3-dihydro-1H-benzimidazol-5-yl, 1H-indazol-5-yl or 2H-indazol-5-yl,
where the 5-membered heterocycle in 2,3-dihydro-1H-indazol-6-yl, 2,3-dihydro-1H-benzimidazol-5-yl, 1H-indazol-5-yl and 2H-indazol-5-yl may be substituted by 1 to 2 substituents selected independently from the group consisting of oxo and methyl,
$R^6$ is chlorine,
$R^7$ is hydrogen,
or a pharmaceutically acceptable salt thereof.

4. A process for preparing a compound of the formula (I) according to claim 1 or a pharmaceutically acceptable salt thereof, wherein either
[A] a compound of the formula

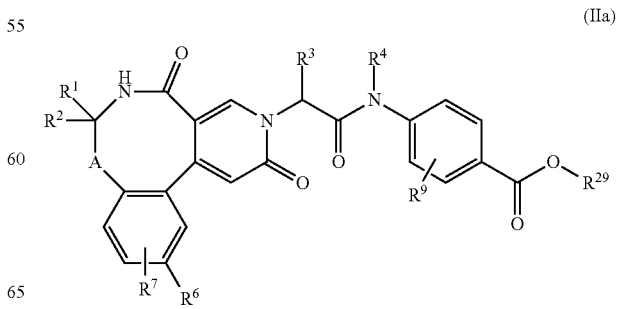

(IIa)

in which
R²⁹ is tert-butyl,
is reacted with an acid to give a compound of the formula

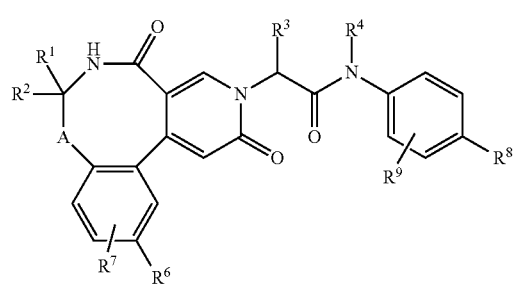
(Ib)

in which
R⁸ is carboxyl, or

[B] a compound of the formula

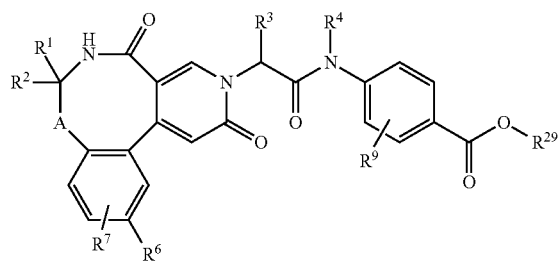
(IIb)

in which
R²⁹ is methyl or ethyl,
is reacted with a base to give a compound of the formula

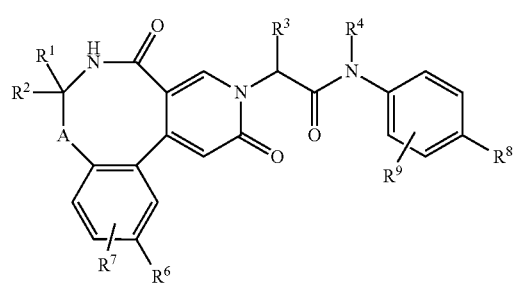
(Ib)

in which
R⁸ is carboxyl,
or
[C] a compound of the formula

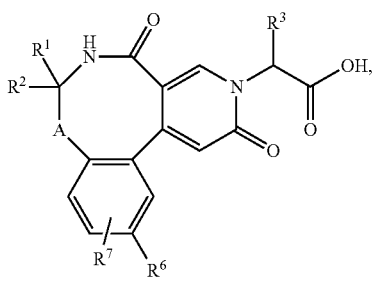
(III)

is reacted with a compound of the formula

(IV)

in the presence of a dehydrating reagent to give a compound of the formula (I).

5. A method of using a compound according to claim 1 for treatment and/or prophylaxis of a thrombotic or thromboembolic disorder, wherein the method comprises administering a therapeutically effective amount of the compound to a patient in need thereof.

6. A method of using a compound according to claim 1 for treatment and/or prophylaxis of an ophthalmic disorder, wherein the method comprises administering a therapeutically effective amount of the compound to a patient in need thereof.

7. A method of using a compound according to claim 1 for treatment and/or prophylaxis of hereditary angiooedema or an inflammatory disorder of the intestine, wherein the method comprises administering a therapeutically effective amount of the compound to a patient in need thereof.

8. A medicament comprising a compound according to claim 1 in combination with an inert, nontoxic, pharmaceutically suitable excipient.

9. A method of using a medicament according to claim 8 for treatment and/or prophylaxis of a thrombotic or thromboembolic disorder, wherein the method comprises administering a therapeutically effective amount of the medicament to a patient in need thereof.

10. A method of using a medicament according to claim 8 for treatment and/or prophylaxis of an ophthalmic disorder, wherein the method comprises administering a therapeutically effective amount of the medicament to a patient in need thereof.

11. A method of using a medicament according to claim 8 for treatment and/or prophylaxis of hereditary angiooedema or an inflammatory disorder of the intestine, wherein the method comprises administering a therapeutically effective amount of the medicament to a patient in need thereof.

12. A method for treating a thrombotic or thromboembolic disorder or an ophthalmic disorder or hereditary angiooedema or an inflammatory disorder of the intestine in a man or animal by administration of a therapeutically effective amount of at least one compound according to claim 1; a medicament comprising the compound in combination with an inert, nontoxic, pharmaceutically suitable excipient.

13. The method according to claim 7, wherein the inflammatory disorder of the intestine is Crohn's disease or ulcerative colitis.

14. The method according to claim 11, wherein the inflammatory disorder of the intestine is Crohn's disease or ulcerative colitis.

15. The method according to claim 12, wherein the inflammatory disorder of the intestine is Crohn's disease or ulcerative colitis.

* * * * *